(12) United States Patent
Nair et al.

(10) Patent No.: US 12,286,428 B2
(45) Date of Patent: Apr. 29, 2025

(54) TRICYCLIC HETEROARYL COMPOUNDS USEFUL AS IRAK4 INHIBITORS

(71) Applicant: BRISTOL-MYERS SQUIBB COMPANY, Princeton, NJ (US)

(72) Inventors: Satheesh Kesavan Nair, Bangalore (IN); Venkatram Reddy Paidi, Bangalore (IN); Kandhasamy Sarkunam, Hosur (IN); Ramesh Kumar Sistla, Bangalore (IN); John Hynes, Washington Crossing, PA (US); Natesan Murugesan, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 774 days.

(21) Appl. No.: 17/627,915

(22) PCT Filed: Jul. 16, 2020

(86) PCT No.: PCT/US2020/042241
§ 371 (c)(1),
(2) Date: Jan. 18, 2022

(87) PCT Pub. No.: WO2021/011724
PCT Pub. Date: Jan. 21, 2021

(65) Prior Publication Data
US 2022/0259205 A1 Aug. 18, 2022

Related U.S. Application Data

(60) Provisional application No. 62/875,563, filed on Jul. 18, 2019.

(51) Int. Cl.
C07D 471/04 (2006.01)
C07D 471/14 (2006.01)
C07D 491/048 (2006.01)

(52) U.S. Cl.
CPC ......... C07D 471/04 (2013.01); C07D 471/14 (2013.01); C07D 491/048 (2013.01)

(58) Field of Classification Search
CPC . C07D 471/04; C07D 471/14; C07D 491/048
USPC ....................................................... 514/292
See application file for complete search history.

(56) References Cited

U.S. PATENT DOCUMENTS

| | | | |
|---|---|---|---|
| 7,919,621 B2 | 4/2011 | Hutchinson et al. |
| 8,575,153 B2 | 11/2013 | Kitamura et al. |
| 8,586,751 B2 | 11/2013 | De Lucca et al. |
| 9,663,467 B2 | 5/2017 | Moslin et al. |
| 2005/0272753 A1 | 12/2005 | Nagashima et al. |

(Continued)

FOREIGN PATENT DOCUMENTS

| EP | 2532656 A1 | 12/2012 |
|---|---|---|
| GB | 2388596 A1 | 11/2003 |

(Continued)

OTHER PUBLICATIONS

Buckley et al., "IRAK-4 inhibitors. Part 1: A series of amides:", Bioorganic & Medicinal Chemistry Letters, vol. 18 pp. 3211-3214 (2008).

(Continued)

Primary Examiner — Kristin A Vajda
(74) Attorney, Agent, or Firm — Gary Greenblatt

(57) ABSTRACT

Disclosed are compounds of Formula (I) or a salt or prodrug thereof, wherein: $X_1$ and $X_2$ are independently C or N, provided that zero or one of $X_1$ and $X_2$ is N; Ring A represented by the structure is: or; and Q, $R_1$, $R_2$, $R_3$, $R_4$, $R_6$, and p are define herein. Also disclosed are methods of using such compounds as modulators of IRAK4, and pharmaceutical compositions comprising such compounds. These compounds are useful in treating, preventing, or slowing inflammatory and autoimmune diseases, or in the treatment of cancer.

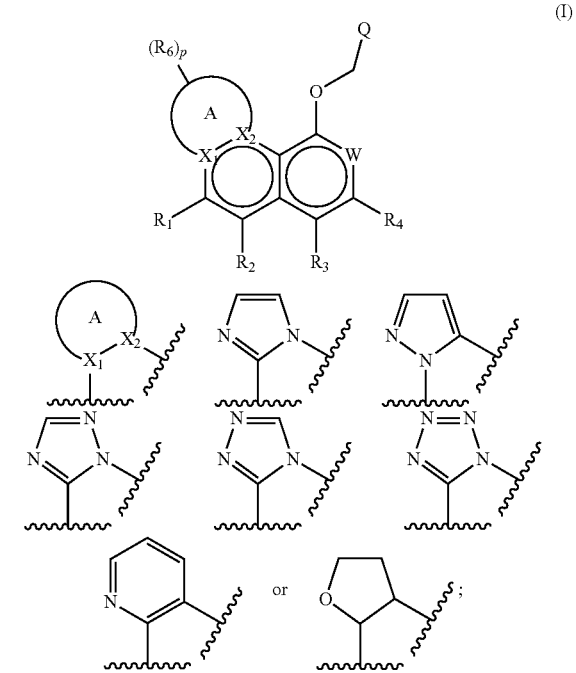

12 Claims, No Drawings
Specification includes a Sequence Listing.

(56) References Cited

U.S. PATENT DOCUMENTS

| | | |
|---|---|---|
| 2006/0148800 A1 | 7/2006 | Stadtmueller et al. |
| 2007/0021456 A1 | 1/2007 | Mitjans et al. |
| 2009/0082329 A1 | 3/2009 | Halley et al. |
| 2011/0230467 A1 | 9/2011 | Shirakami et al. |

FOREIGN PATENT DOCUMENTS

| | | |
|---|---|---|
| WO | 2002102800 A1 | 12/2002 |
| WO | 2003013523 A1 | 2/2003 |
| WO | 2004065378 A1 | 8/2004 |
| WO | 2005007646 A1 | 1/2005 |
| WO | 2005075468 A2 | 8/2005 |
| WO | 2008148889 A1 | 12/2008 |
| WO | 2009046416 A1 | 4/2009 |
| WO | 2011/014817 A1 | 2/2011 |
| WO | 2011053701 A1 | 5/2011 |
| WO | 2012125893 A1 | 9/2012 |
| WO | 2012129258 A2 | 9/2012 |
| WO | 2012149567 A1 | 11/2012 |
| WO | 2012162254 A1 | 11/2012 |
| WO | 2013106612 A1 | 7/2013 |
| WO | 2013106614 A1 | 7/2013 |
| WO | 2013106641 A1 | 7/2013 |
| WO | 2014074657 A1 | 5/2014 |
| WO | 2014074660 A1 | 5/2014 |
| WO | 2014074675 A1 | 5/2014 |
| WO | 2015/104688 A1 | 7/2015 |
| WO | 2015/150995 A1 | 10/2015 |
| WO | 2018/209012 A1 | 11/2015 |
| WO | 2016144844 A1 | 9/2016 |
| WO | 2016144849 A1 | 9/2016 |
| WO | 2016210034 A1 | 12/2016 |
| WO | 2016210037 A1 | 12/2016 |
| WO | 2017033093 A1 | 3/2017 |
| WO | 2019089422 A1 | 5/2019 |

OTHER PUBLICATIONS

Buckley et al., "IRAK-4 inhibitors. Part II: A structure-based assessment of imidazo[1,2-a]pyridine binding", Bioorganic Medicinal Chem Letters, vol. 18(11) pp. 3291-3295 (2008).

Buckley, et al., "IRAK-4 inhibitors. Part III: A series of imidazo[1,2-a]pyridines", Bioorganic Medicinal Chem Letters, vol. 18(11) pp. 36-56 (2008).

Degorce et al., "Discovery of Novel 3-Quinoline Carboxamides as Potent, Selective, and Orally Bioavailable Inhibitors of Ataxia Telangiectasia Mutated (ATM) Kinase", J. Med. Chem. , vol. 59, 6281-6292 (2016).

Fahim et al., "Regioselective synthesis and DFT study of novel fused heterocyclic utilizing Thermal heating and Microwave Irradiation", Afinidad 75, vol. 582, p. 148-159 (2018).

Garofolo et al., "Novel cinnoline-based inhibitors of LRRK2 kinase activity", Bioorg. Med. Chem. Lett. vol. 23 pp. 71-74 (2013).

Genung et al., "Small Molecule Inhibition of Interleukin-1 Receptor-Associated Kinase 4 (IRAK4)", Progress in Medici al Chemistry, vol. 56, pp. 117-163 (2017).

Hynes et al., Annual Reports in Medicinal Chemistry, vol. 49, pp. 117-133, 2014.

Kategaonkar et al., Synthesis and antimicrobial activity of tetrazolofl,5-rt ]-quinoline-4-carbonitrile derivatives, Monatsh Chem , vol. 1 , pp. 787-791 (2010).

Pike et al., "The Identification of Potent, Selective, and Orally Available Inhibitors of Ataxia Telangiectasia Mutated (ATM) Kinase: The Discovery of AZD0156 (8-{6-[3-(Dimethylamino)propoxy]pyridin-3-yl}-3-methyl-1-(tetrahydro-2H-pyran-4-yl)-1,3 dihydro-2H-imidazo[4,5-c]quinolin-2-one)", J. Med. Chem. vol. 61, 3823-3841 (2018).

Seganish, W. Michael, "Inhibitors of interleukin-1 receptor-associated kinase 4 (IRAK4): a patent review (2012-2015)", Expert Opinion on Therapeutic Patents, vol. 26, No. 8, pp. 917-932 (2016).

Tumey et al., "Identification and optimization of indolo[2,3-c]quinoline inhibitors of IRAK4", Bioorganic & Medicinal Chemistry Letters, vol. 24, pp. 2066-2072 (2014).

TRICYCLIC HETEROARYL COMPOUNDS USEFUL AS IRAK4 INHIBITORS

CROSS REFERENCE

This application is a 371 application of International Application No. PCT/US2020/042241, filed Jul. 16, 2020, which claims the benefit of U.S. Provisional Application Ser. No. 62/875,563, filed Jul. 18, 2019, the content of each is hereby fully incorporated herein in its entirety.

DESCRIPTION

The present invention generally relates to tricyclic heteroaryl compounds useful as kinase inhibitors, including the modulation of IRAK-4. Provided herein are tricyclic heteroaryl compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including IRAK-4 in a mammal.

Toll/IL-1 receptor family members are important regulators of inflammation and host resistance. The Toll like receptor (TLR) family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Members of the IRAK family of serine/threonine kinases are recruited to the receptor via interactions with MyD88. The family consists of four members. Several lines of evidence indicate that IRAK4 plays a critical and non-redundant role in initiating signaling via MyD88 dependent TLRs and IL-1R family members. Structural data confirms that IRAK4 directly interacts with MyD88 and subsequently recruits either IRAK1 or IRAK2 to the receptor complex to facilitate downstream signaling (Lin, S. et al., *Nature*, 465: 885-890 (2010)). IRAK4 directly phosphorylates IRAK1 to facilitate downstream signaling to the E3 ubiquitin ligase TRAF6, resulting in activation of the serine/threonine kinase TAK1 with subsequent activation of the NFκB pathway and MAPK cascade (Flannery, S. et al., Biochem. Pharmacol., 80:1981-1991 (2010)). A subset of human patients was identified who lack IRAK4 expression (Picard, C. et al., *Science*, 299:2076-2079 (2003)). Cells from these patients fail to respond to all TLR agonists with the exception of TLR3 as well as to members of the IL-1 family including IL-1β and IL-18 (Ku, C. et al., *J. Exp. Med.*, 204:2407-2422 (2007)). Deletion of IRAK4 in mice results in a severe block in IL-1, IL-18 and all TLR dependent responses with the exception of TLR3 (Suzuki, N. et al., *Nature*, 416:750-754 (2002)). In contrast, deletion of either IRAK1 (Thomas, J. A. et al., *J. Immunol.*, 163:978-984 (1999); Swantek, J. L. et al., *J. Immunol.*, 164:4301-4306 (2000) or IRAK2 (Wan, Y. et al., *J. Biol. Chem.*, 284:10367-10375 (2009)) results in partial loss of signaling. Furthermore, IRAK4 is the only member of the IRAK family whose kinase activity has been shown to be required for initiation of signaling. Replacement of wild type IRAK4 in the mouse genome with a kinase inactive mutant (KDKI) impairs signaling via all MyD88 dependent receptors including IL-1, IL-18 and all TLRs with the exception of TLR3 (Koziczak-Holbro, M. et al., *J. Biol. Chem.*, 282:13552-13560 (2007); Kawagoe, T. et al., *J. Exp. Med.*, 204:1013-1024 (2007); and Fraczek, J. et al., *J. Biol. Chem.*, 283:31697-31705 (2008)).

As compared to wild type animals, IRAK4 KDKI mice show greatly reduced disease severity in mouse models of multiple sclerosis (Staschke, K. A. et al., *J. Immunol.*, 183:568-577 (2009)), rheumatoid arthritis (Koziczak-Holbro, M. et al., *Arthritis Rheum.*, 60:1661-1671 (2009)), atherosclerosis (Kim, T. W. et al., *J. Immunol.*, 186:2871-2880 (2011) and Rekhter, M. et al., *Biochem. Biophys. Res. Comm.*, 367:642-648 (2008)), and myocardial infarction (Maekawa, Y. et al., *Circulation*, 120:1401-1414 (2009)). As described, IRAK4 inhibitors will block all MyD88 dependent signaling. MyD88 dependent TLRs have been shown to contribute to the pathogenesis of multiple sclerosis, rheumatoid arthritis, cardiovascular disease, metabolic syndrome, sepsis, systemic lupus erythematosus, inflammatory bowel diseases including Crohn's disease and ulcerative colitis, autoimmune uveitis, asthma, allergy, type I diabetes, and allograft rejection (Keogh, B. et al., *Trends Pharmacol. Sci.*, 32:435-442 (2011); Mann, D. L., *Circ. Res.*, 108:1133-1145 (2011); Horton, C. G. et al., *Mediators Inflamm.*, Article ID 498980 (2010), doi:10.1155/2010/498980; Goldstein, D. R. et al., *J. Heart Lung Transplant.*, 24:1721-1729 (2005); and Cario, E., Inflamm. Bowel Dis., 16:1583-1597 (2010)). Oncogenically active MyD88 mutations in diffuse large B cell lymphomas have been identified that are sensitive to IRAK4 inhibition (Ngo, V. N. et al., *Nature*, 470:115-121 (2011)). Whole genome sequencing also identified mutations in MyD88 associated with chronic lymphatic leukemia suggesting that IRAK4 inhibitors may also have utility in treating leukemias (Puente, X. S. et al., *Nature*, 475:101-105 (2011)).

In addition to blocking TLR signaling, IRAK4 inhibitors will also block signaling by members of the IL-1 family. Neutralization of IL-1 has been shown to be efficacious in multiple diseases including gout; gouty arthritis; type 2 diabetes; auto-inflammatory diseases including Cryopyrin-Associated Periodic Syndromes (CAPS), TNF Receptor Associated Periodic Syndrome (TRAPS), Familial Mediterranean Fever (FMF), adult onset stills; systemic onset juvenile idiopathic arthritis; stroke; Graft-versus-Host Disease (GVHD); smoldering multiple myeloma; recurrent pericarditis; osteoarthritis; emphysema (Dinarello, C. A., *Eur. J. Immunol.*, 41:1203-1217 (2011) and Couillin, I. et al., *J. Immunol.*, 183:8195-8202 (2009)). In a mouse model of Alzheimer's disease, blockade of IL-1 receptor improved cognitive defects, attenuated tau pathology and reduced oligomeric forms of amyloid-β (Kitazawa, M. et al., *J. Immunol.*, 187:6539-6549 (2011)). IL-1 has also been shown to be a critical link to adaptive immunity, driving differentiation of the TH17 effector T cell subset (Chung, Y. et al., *Immunity*, 30:576-587 (2009)). Therefore, IRAK4 inhibitors are predicted to have efficacy in TH17 associated diseases including multiple sclerosis, psoriasis, inflammatory bowel diseases, autoimmune uveitis, and rheumatoid arthritis (Wilke, C. M. et al., *Trends Immunol.*, 32:603-661 (2011)).

In view of the conditions that may benefit by treatment involving modulation of protein kinases, it is immediately apparent that new compounds capable of modulating protein kinases such as IRAK-4 and methods of using these compounds could provide substantial therapeutic benefits to a wide variety of patients.

SUMMARY OF THE INVENTION

The present invention relates to a new class of tricyclic heteroaryl tricyclic heteroaryl compounds found to be effective inhibitors of protein kinases including IRAK-4. These compounds are provided to be useful as pharmaceuticals with desirable stability, bioavailability, therapeutic index, and toxicity values that are important to their drugability.

The present invention provides to compounds of Formula (I) that are useful as inhibitors of IRAK-4, and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of IRAK-4 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

One embodiment provides a method for treating inflammatory and autoimmune diseases wherein the treatment of inflammatory diseases is even more preferred. Particular, inflammatory and autoimmune diseases include, but are not limited to, Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes (CAPS), TNF receptor associated periodic syndrome (TRAPS), familial Mediterranean fever (FMF), adult onset stills, systemic onset juvenile idiopathic arthritis, multiple sclerosis, neuropathic pain, gout, and gouty arthritis.

One embodiment provides a method for treating gout and gouty arthritis.

An alternate preferred embodiment is a method for treating metabolic diseases, including type 2 diabetes and atherosclerosis.

One embodiment provides a method for treating cancer comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancer.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

The first aspect of the present invention provides at least one compound of Formula (I):

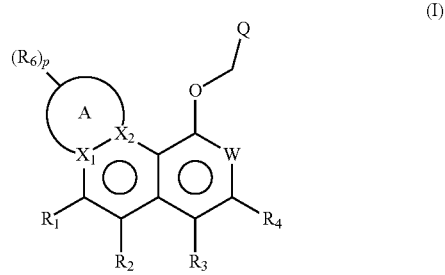

or a salt or prodrug thereof, wherein:
W is $CR_5$ or N;
$X_1$ and $X_2$ are independently C or N, provided that zero or one of $X_1$ and $X_2$ is N;
Ring A represented by the structure

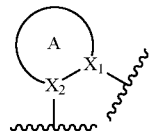

is:

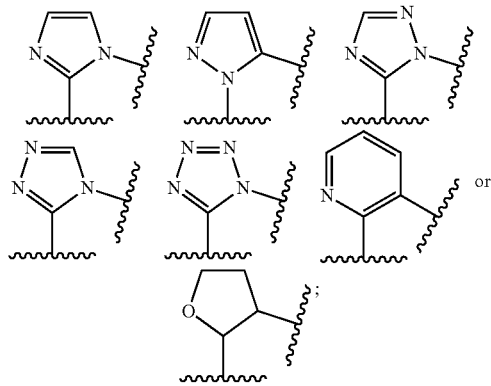

$R_1$ is —CN or —C(O)NH$_2$;
$R_2$ is hydrogen or —NH(CH$_3$);
$R_3$ is hydrogen or F
$R_4$ is hydrogen, F, or —CH$_3$;
$R_5$ is hydrogen;
each $R_6$ is independently —CH$_3$, —CF$_3$, or —C(CH$_3$)$_2$OH;

Q is

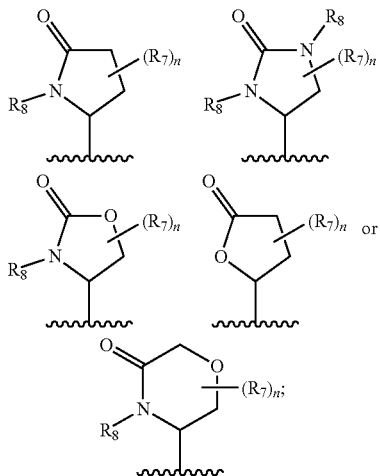

each R$_7$ is F, C$_{1-3}$ alkyl, or C$_{1-2}$ fluoroalkyl;
each R$_8$ is independently hydrogen or —CH$_2$OH;
n is zero, 1, 2, or 3; and
p is zero, 1 or 2.

In one embodiment, a compound of Formula (I) or a salt or a prodrug thereof is provided wherein W is CR$_5$. Compounds of this embodiment have the structure of Formula (IA):

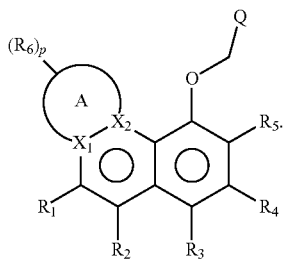

(IA)

In one embodiment, a compound of Formula (I) or a salt or a prodrug thereof is provided wherein W is N. Compounds of this embodiment have the structure of Formula (IB):

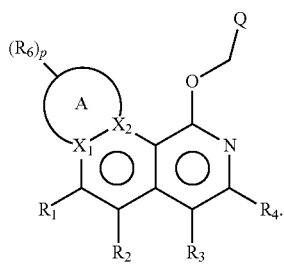

(IB)

In one embodiment, a compound of Formula (I) or a salt or a prodrug thereof is provided wherein Ring A is

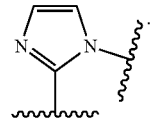

The compounds of this embodiment have the structure of Formula (II):

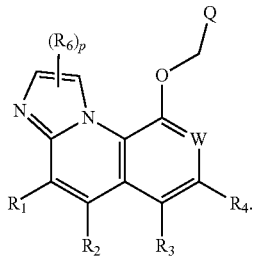

(II)

Included in this embodiment are compounds in which W is CR$_5$, having the structure of Formula (IIA). Also included in this embodiment are compounds in which W is N, having the structure of Formula (IIB).

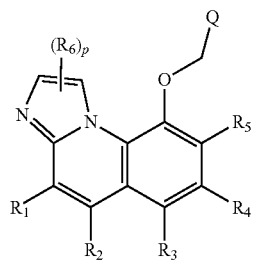

(IIA)

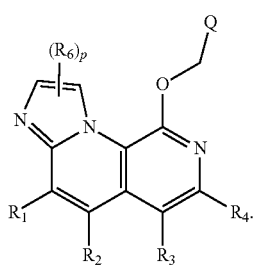

(IIB)

In one embodiment, a compound of Formula (I) or a salt or a prodrug thereof is provided wherein Ring A is

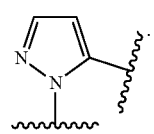

The compounds of this embodiment have the structure of Formula (III):

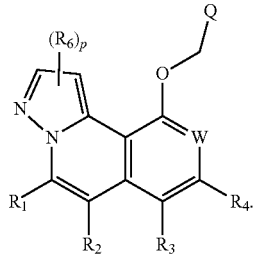

(III)

Included in this embodiment are compounds in which W is CR$_5$, having the structure of Formula (IIIA). Also included in this embodiment are compounds in which W is N, having the structure of Formula (IIIB).

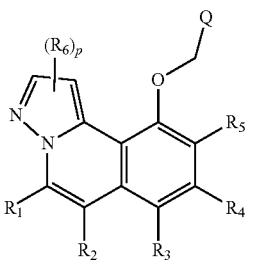

(IIIA)

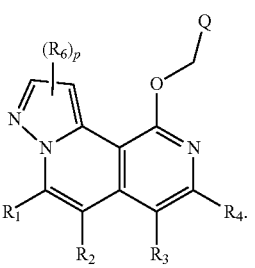

(IIIB)

In one embodiment, a compound of Formula (I) or a salt or a prodrug thereof is provided wherein Ring A is

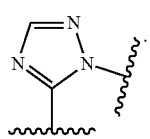

The compounds of this embodiment have the structure of Formula (IV):

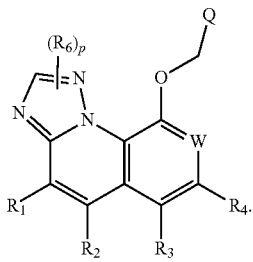

(IV)

Included in this embodiment are compounds in which W is CR$_5$, having the structure of Formula (IVA). Also included in this embodiment are compounds in which W is N, having the structure of Formula (IVB).

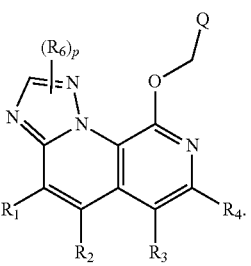

(IVA)

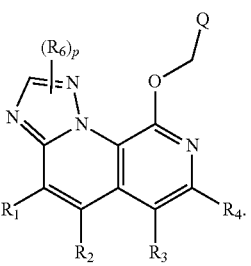

(IVB)

In one embodiment, a compound of Formula (I) or a salt or a prodrug thereof is provided wherein Ring A is

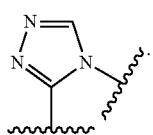

The compounds of this embodiment have the structure of Formula (V):

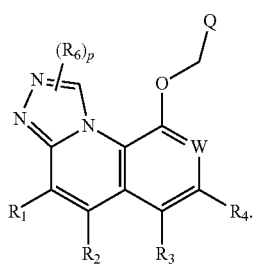
(V)

Included in this embodiment are compounds in which W is CR$_5$, having the structure of Formula (VA). Also included in this embodiment are compounds in which W is N, having the structure of Formula (VB).

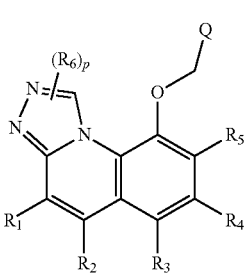
(VA)

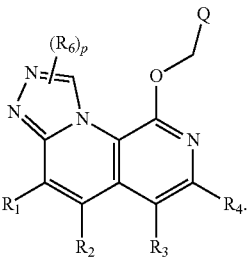
(VB)

In one embodiment, a compound of Formula (I) or a salt or a prodrug thereof is provided wherein Ring A is

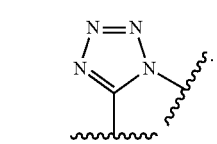

The compounds of this embodiment have the structure of Formula (VI):

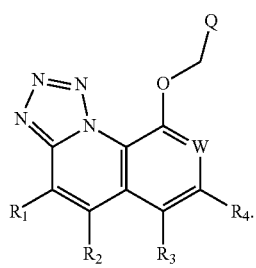
(VI)

Included in this embodiment are compounds in which W is CR$_5$, having the structure of Formula (VIA). Also included in this embodiment are compounds in which W is N, having the structure of Formula (VIB).

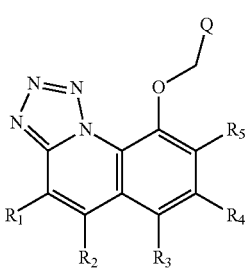
(VIA)

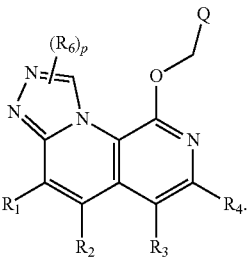
(VIB)

In one embodiment, a compound of Formula (I) or a salt or a prodrug thereof is provided wherein Ring A is

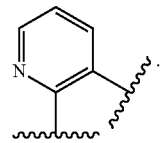 [SMILES: *c1cccnc1*]

The compounds of this embodiment have the structure of Formula (VII):

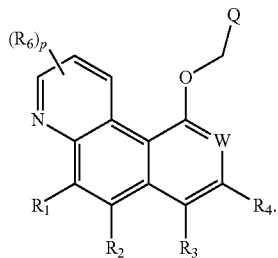
(VII)

Included in this embodiment are compounds in which W is CR₅, having the structure of Formula (VIIA). Also included in this embodiment are compounds in which W is N, having the structure of Formula (VIIB).

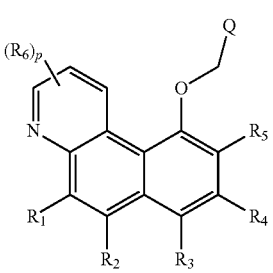
(VIIA)

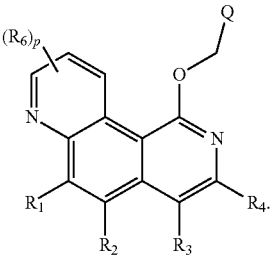
(VIIB)

In one embodiment, a compound of Formula (I) or a salt or a prodrug thereof is provided wherein Ring A is

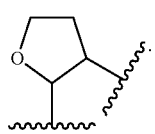 [SMILES: *C1CCOC1*]

The compounds of this embodiment have the structure of Formula (VIII):

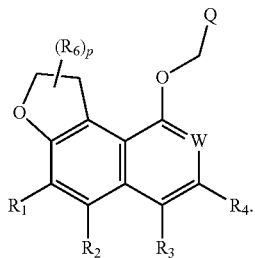
(VIII)

Included in this embodiment are compounds in which W is CR₅, having the structure of Formula (VIIIA). Also included in this embodiment are compounds in which W is N, having the structure of Formula (VIIIB).

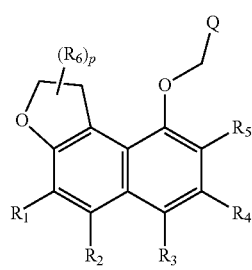
(VIIIA)

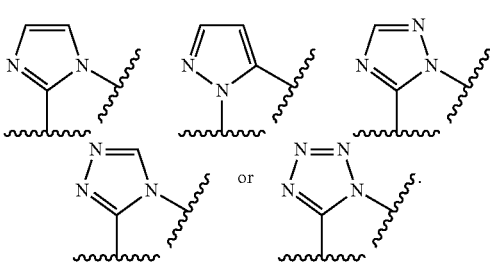
(VIIIB)

In one embodiment, a compound of Formula (I) or a salt or a prodrug thereof is provided wherein Ring A is:

Included in this embodiment are compounds in which W is CR₅. Also included in this embodiment are compound in which W is N.

In one embodiment, a compound of Formula (I) or a salt or a prodrug thereof is provided wherein Ring A is:

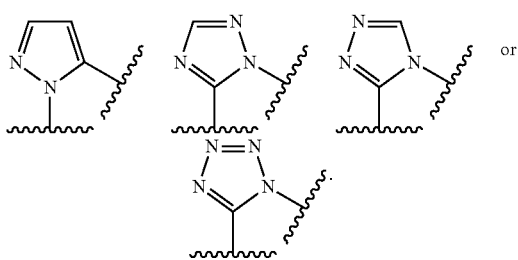

Included in this embodiment are compounds in which W is CR$_5$. Also included in this embodiment are compound in which W is N.

In one embodiment, a compound of Formula (I) or a salt or a prodrug thereof is provided wherein Q is:

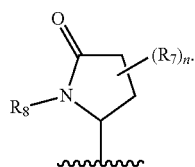

Included in this embodiment are compounds in which R$_8$ is hydrogen.

In one embodiment, a compound of Formula (I) or a salt or a prodrug thereof is provided wherein Q is:

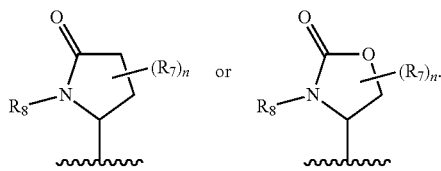

Included in this embodiment are compounds in which R$_8$ is hydrogen.

In one embodiment, a compound of Formula (I) or a salt or a prodrug thereof is provided wherein Q is:

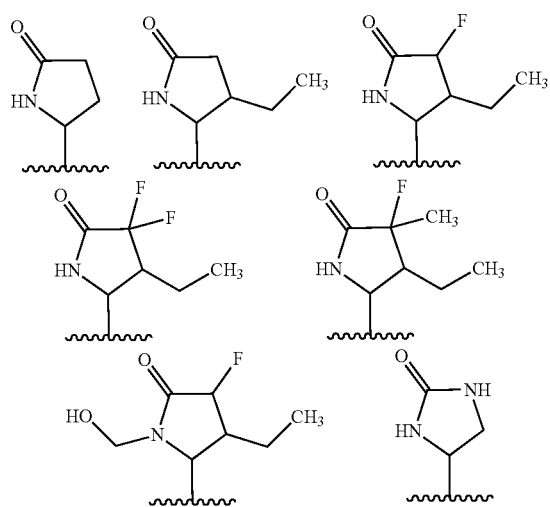

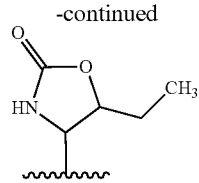

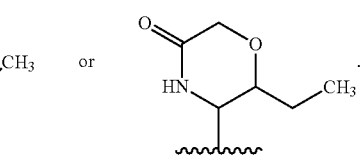

Included in this embodiment are compounds in which W is CR$_5$. Also included in this embodiment are compounds in which W is N.

In one embodiment, a compound of Formula (I) or a salt or a prodrug thereof is provided wherein Ring A is:

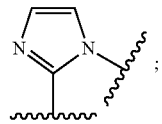 [SMILES: *c1nccn1*]

and Q is:

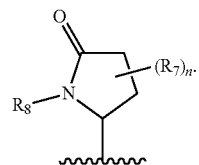

Included in this embodiment are compounds in which R$_8$ is hydrogen. Also included in this embodiment are compounds in which W is CR$_5$. Additionally, included in this embodiment are compounds in which W is N.

In one embodiment, a compound of Formula (I) or a salt or a prodrug thereof is provided wherein R$_2$ is hydrogen.

In one embodiment, a compound of Formula (I) or a salt or a prodrug thereof is provided wherein R$_5$ is hydrogen.

In one embodiment, a compound of Formula (I) or a salt or a prodrug thereof is provided wherein R$_2$ is hydrogen; R$_3$ is hydrogen, R$_4$ is hydrogen, and R$_5$, when present, is hydrogen.

One embodiment provides a compound of Formula (I) or a salt thereof, wherein said compound is selected from: (S)-9-((5-oxopyrrolidin-2-yl)methoxy)imidazo[1,2-a]quinoline-4-carboxamide (1); 9-(((2S,3R)-3-ethyl-5-oxopyrrolidin-2-yl)methoxy) imidazo[1,2-a]quinoline-4-carboxamide (2); 9-(((2S,3S)-3-ethyl-5-oxopyrrolidin-2-yl) methoxy) imidazo[1,2-a]quinoline-4-carboxamide (3); 9-(((2S,3S,4R)-3-ethyl-4-fluoro-5-oxopyrrolidin-2-yl)methoxy) imidazo[1,2-a]quinoline-4-carboxamide (4); 9-(((2S,3S,4S)-3-ethyl-4-fluoro-5-oxopyrrolidin-2-yl)methoxy) imidazo[1,2-a]quinoline-4-carboxamide (5); 9-(((2S,3S,4S)-3-ethyl-4-fluoro-4-methyl-5-oxopyrrolidin-2-yl) methoxy) imidazo[1,2-a]quinoline-4-carboxamide (6); (R)-9-((5-oxomorpholin-3-yl)methoxy) imidazo[1,2-a] quinoline-4-carboxamide (7); 9-(((2S,3S)-3-ethyl-4,4-difluoro-5-oxopyrrolidin-2-yl)methoxy)imidazo[1,2-a]

quinoline-4-carboxamide (10); 9-(((2S,3R)-3-ethyl-5-oxopyrrolidin-2-yl)methoxy)-2-methylimidazo[1,2-a]quinoline-4-carboxamide (11); 9-(((2S,3S,4S)-3-ethyl-4-fluoro-5-oxopyrrolidin-2-yl)methoxy)-2-methylimidazo[1,2-a]quinoline-4-carboxamide (12); 9-(((2S,3S,4S)-3-ethyl-4-fluoro-5-oxopyrrolidin-2-yl)methoxy)-2-(2-hydroxypropan-2-yl)imidazo[1,2-a]quinoline-4-carboxamide (13); 9-(((2S,3R)-3-ethyl-5-oxopyrrolidin-2-yl)methoxy)-6-fluoroimidazo[1,2-a]quinoline-4-carboxamide (14); 9-(((2S,3S,4S)-3-ethyl-4-fluoro-5-oxopyrrolidin-2-yl)methoxy)-6-fluoroimidazo[1,2-a]quinoline-4-carboxamide (15); 1-(((2S,3R)-3-ethyl-5-oxopyrrolidin-2-yl)methoxy)imidazo[1,2-a][1,7]naphthyridine-6-carboxamide (16); 1-(((2S,3S,4S)-3-ethyl-4-fluoro-5-oxopyrrolidin-2-yl)methoxy)imidazo[1,2-a][1,7]naphthyridine-6-carboxamide (17); 1-(((2S,3R)-3-ethyl-5-oxopyrrolidin-2-yl)methoxy)-8-methylimidazo[1,2-a][1,7]naphthyridine-6-carboxamide (18); 1-(((2S,3S,4S)-3-ethyl-4-fluoro-5-oxopyrrolidin-2-yl)methoxy)-8-methylimidazo[1,2-a][1,7]naphthyridine-6-carboxamide (19); 1-(((2S,3S)-3-ethyl-4,4-difluoro-5-oxopyrrolidin-2-yl)methoxy)imidazo[1,2-a][1,7]naphthyridine-6-carboxamide (20); 1-(((2S,3S)-3-ethyl-4,4-difluoro-5-oxopyrrolidin-2-yl)methoxy)-8-methylimidazo[1,2-a][1,7]naphthyridine-6-carboxamide (21); 1-(((4R,5S)-5-ethyl-2-oxooxazolidin-4-yl)methoxy)imidazo[1,2-a][1,7]naphthyridine-6-carboxamide (22); 1-(((4S,5R)-5-ethyl-2-oxooxazolidin-4-yl)methoxy)imidazo[1,2-a][1,7]naphthyridine-6-carboxamide (23); 1-(((4S,5S)-5-ethyl-2-oxooxazolidin-4-yl) methoxy)imidazo[1,2-a][1,7]naphthyridine-6-carboxamide (24); 1-(((2R,3S)-2-ethyl-5-oxomorpholin-3-yl)methoxy)imidazo[1,2-a][1,7]naphthyridine-6-carboxamide (25); 1-(((2S,3R)-2-ethyl-5-oxomorpholin-3-yl)methoxy)imidazo[1,2-a][1,7]naphthyridine-6-carboxamide (26); (S)-1-((2-oxoimidazolidin-4-yl)methoxy)imidazo[1,2-a][1,7]naphthyridine-6-carboxamide (27); 1-(((2S,3R)-3-ethyl-5-oxopyrrolidin-2-yl)methoxy)-3-methylimidazo[1,2-a][1,7]naphthyridine-6-carboxamide (28); 1-(((2S,3R)-3-ethyl-5-oxopyrrolidin-2-yl)methoxy)-3,8-dimethylimidazo[1,2-a][1,7]naphthyridine-6-carboxamide (29); 1-(((2S,3R)-3-ethyl-5-oxopyrrolidin-2-yl)methoxy)-8-(trifluoromethyl)imidazo[1,2-a][1,7]naphthyridine-6-carboxamide (30); 1-(((2S,3S)-3-ethyl-5-oxopyrrolidin-2-yl)methoxy)-8-(trifluoromethyl)imidazo[1,2-a][1,7]naphthyridine-6-carboxamide (31); (1-(((2S,3S,4S)-3-ethyl-4-fluoro-1-(hydroxymethyl)-5-oxopyrrolidin-2-yl)methoxy)imidazo[1,2-a][1,7]naphthyridine-6-carboxamide (32); 1-((((3R)-3-ethyl-5-oxopyrrolidin-2-yl)methyl)amino)imidazo[1,2-a][1,7]naphthyridine-6-carboxamide (33); 10-(((2S,3S,4S)-3-ethyl-4-fluoro-5-oxopyrrolidin-2-yl)methoxy) pyrazolo[5,1-a]isoquinoline-5-carboxamide (34); 10-(((2S,3R)-3-ethyl-5-oxopyrrolidin-2-yl)methoxy)pyrazolo[5,1-a]isoquinoline-5-carboxamide (35); 1-(((2S,3S,4S)-3-ethyl-4-fluoro-5-oxopyrrolidin-2-yl)methoxy)pyrazolo[5,1-a][2,7]naphthyridine-6-carboxamide (36); 9-(((2S,3R)-3-ethyl-5-oxopyrrolidin-2-yl)methoxy)-[1,2,4]triazolo[1,5-a]quinoline-4-carboxamide (37); 9-(((2S,3S,4S)-3-ethyl-4-fluoro-5-oxopyrrolidin-2-yl)methoxy)-[1,2,4]triazolo[1,5-a]quinoline-4-carboxamide (38); 9-(((2S,3S)-3-ethyl-4,4-difluoro-5-oxopyrrolidin-2-yl)methoxy)-[1,2,4]triazolo[1,5-a]quinoline-4-carboxamide (39); 9-(((2S,3S,4S)-3-ethyl-4-fluoro-5-oxopyrrolidin-2-yl)methoxy)-2-methyl-[1,2,4]triazolo [1,5-a]quinoline-4-carboxamide (40); 9-(((2S,3R)-3-ethyl-5-oxopyrrolidin-2-yl) methoxy)-[1,2,4]triazolo[4,3-a]quinoline-4-carboxamide (41); 9-(((2S,3S)-3-ethyl-5-oxopyrrolidin-2-yl)methoxy)-[1,2,4]triazolo[4,3-a]quinoline-4-carboxamide (42); 9-(((2S,3S,4S)-3-ethyl-4-fluoro-5-oxopyrrolidin-2-yl)methoxy)-[1,2,4]triazolo[4,3-a]quinoline-4-carboxamide (43); 9-(((2S,3R)-3-ethyl-5-oxopyrrolidin-2-yl)methoxy) tetrazolo[1,5-a]quinoline-4-carboxamide (44); 9-(((2S,3S,4S)-3-ethyl-4-fluoro-5-oxopyrrolidin-2-yl)methoxy)tetrazolo[1,5-a]quinoline-4-carboxamide (45); 9-(((2S,3R)-3-ethyl-5-oxopyrrolidin-2-yl)methoxy)-[1,2,4]triazolo[1,5-a][1,7]naphthyridine-4-carboxamide (46); 9-(((2S,3S,4S)-3-ethyl-4-fluoro-5-oxopyrrolidin-2-yl)methoxy)-[1,2,4]triazolo[1,5-a][1,7]naphthyridine-4-carboxamide (47); 9-(((2S,3S)-3-ethyl-4,4-difluoro-5-oxopyrrolidin-2-yl)methoxy)-[1,2,4]triazolo[1,5-a][1,7]naphthyridine-4-carboxamide (48); 9-(((2S,3R)-3-ethyl-5-oxopyrrolidin-2-yl)methoxy)-2-methyl-[1,2,4]triazolo[1,5-a][1,7]naphthyridine-4-carboxamide (49); 1-(((2S,3S,4S)-3-ethyl-4-fluoro-5-oxotetrahydrofuran-2-yl)methoxy)-8-methyl-8,9-dihydrofuro[2,3-h]isoquinoline-6-carboxamide (50-52); 1-(((2S,3R)-3-ethyl-5-oxotetrahydrofuran-2-yl) methoxy)-8-methyl-8,9-dihydrofuro[2,3-h]isoquinoline-6-carboxamide (53); 1-(((2S,3R)-3-ethyl-5-oxopyrrolidin-2-yl)methoxy)-8,9-dihydrofuro[2,3-h]isoquinoline-6-carboxamide (54); 1-(((2S,3R)-3-ethyl-5-oxopyrrolidin-2-yl)methoxy)-2,7-phenanthroline-6-carboxamide (55); 1-(((2S,3S,4S)-3-ethyl-4-fluoro-5-oxopyrrolidin-2-yl)methoxy)-2,7-phenanthroline-6-carboxamide (56); 9-(((2S,3R)-3-ethyl-5-oxopyrrolidin-2-yl)methoxy)-7-fluoro-5a,9a-dihydroimidazo[1,2-a]quinoline-4-carboxamide (57); 9-(((2S,3S,4S)-3-ethyl-4-fluoro-5-oxopyrrolidin-2-yl)methoxy)-7-fluoro-5a,9a-dihydroimidazo[1,2-a]quinoline-4-carboxamide (58); 9-(((2S,3R)-3-ethyl-5-oxopyrrolidin-2-yl)methoxy)-8-fluoro-5a,9a-dihydroimidazo[1,2-a]quinoline-4-carboxamide (59); 9-(((2S,3R)-3-ethyl-5-oxopyrrolidin-2-yl)methoxy)-5a,9a-dihydroimidazo[1,2-a]quinoline-4-carbonitrile (60); 9-(((2S,3S,4S)-3-ethyl-4-fluoro-5-oxopyrrolidin-2-yl)methoxy)-5-(methylamino)-5a,9a-dihydroimidazo[1,2-a]quinoline-4-carboxamide (61); 10-(((2S,3S,4S)-3-ethyl-4-fluoro-5-oxopyrrolidin-2-yl)methoxy)-2-methyl-6a,10a-dihydropyrazolo[5,1-a]isoquinoline-5-carboxamide (62); and 1-(((2S,3S,4S)-3-ethyl-4-fluoro-5-oxopyrrolidin-2-yl)methoxy)-8,8-dimethyl-8,9-dihydrofuro[2,3-h]isoquinoline-6-carboxamide (63).

One embodiment provides compounds of the Formula (I) having IRAK4 $IC_{50}$ values of ≤0.6 μM.

One embodiment provides compounds of the Formula (I) having IRAK4 $IC_{50}$ values of ≤0.1 μM.

One embodiment provides compounds of the Formula (I) having IRAK4 $IC_{50}$ values of ≤0.05 μM.

One embodiment provides compounds of the Formula (I) having IRAK4 $IC_{50}$ values of ≤0.025 μM.

One embodiment provides compounds of the Formula (I) having IRAK4 $IC_{50}$ values of ≤0.015 μM.

One embodiment provides compounds of the Formula (I) having IRAK4 $IC_{50}$ values of ≤0.01 μM.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to IRAK4; or effective to treat or prevent autoimmune and/or inflammatory disease states, such as multiple sclerosis and rheumatoid arthritis; or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The compounds of the invention modulate kinase activity, including the modulation of IRAK-4. Other types of kinase activity that may be modulated by the compounds of the instant invention include, but are not limited to, the Pelle/IRAK family and mutants thereof.

Accordingly, compounds of Formula (I) have utility in treating conditions associated with the modulation of kinase activity, and particularly the selective inhibition of IRAK-4 activity or the inhibition of IRAK and other Pelle family kinases. Such conditions include TLR/IL-1 family receptor associated diseases in which cytokine levels are modulated as a consequence of intracellular signaling. Moreover, the compounds of Formula (I) have advantageous selectivity for IRAK-4 activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors IRAK-4, compounds of Formula (I) are useful in treating TLR/IL-1 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional IRAK-4-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

When the terms "IRAK-4-associated condition" or "IRAK-4-associated disease or disorder" are used herein, each is intended to encompass all of the conditions identified above as if repeated at length, as well as any other condition that is affected by IRAK-4 kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit IRAK-4 and/or treat diseases.

The methods of treating IRAK-4 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit IRAK-4 and/or treat diseases associated with IRAK-4.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IRAK-4 kinase-associated conditions, including TLR and IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

EXAMPLES

Compounds of the current invention and intermediates used in the preparation of compounds of the current invention can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared.

Column chromatography was performed with pre-packed silica gel cartridges using an Isco medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

AcOH acetic acid
$Ac_2O$ acetic anhydride
aq. aqueous
BISPIN bis(pinacolato)diboron
$BOC_2O$ di-tert-butyl dicarbonate
brine saturated aqueous sodium chloride
DCE dichloroethane
DCM dichloromethane
DIBAL-H diisobutylalmuminium hydride
DIPEA diisopropylethylamine
DMA N,N-dimethylacetamide
DMAP dimethylaminopyridine
DMF N,N-dimethylformamide
DMF-DMA N,N-dimethylformamide dimethyl acetal
DMSO dimethyl sulfoxide
DPPF 1,1'-bis(diphenylphosphino)ferrocene
$Et_3N$ triethylamine
EtOAc ethyl acetate
EtOH ethanol
g gram(s)
h hour(s)
HATU O-(7-azabenzotriazol-1-yl)-N, N, N', N'-tetramethyluronium hexafluorophosphate
HPLC High Performance Liquid Chromatography
LAH lithium aluminum hydride
LCMS Liquid Chromatography-Mass Spectroscopy LDA lithium diisopropylamide
m-CPBA 3-chloroperbenzoic acid
MeCN acetonitrile
MeOH methanol
MPLC medium pressure liquid chromatography
PCC pyridinium chlorochromate
Pd(Ph₃P)₄ tetrakis(triphenylphosphine)palladium
pet ether petroleum ether
TEA triethylamine
TFA trifluoroacetic acid
TFAA trifluoroacetic anhydride
THF tetrahydrofuran Example 1

(S)-9-((5-oxopyrrolidin-2-yl)methoxy)imidazo[1,2-a]quinoline-4-carboxamide

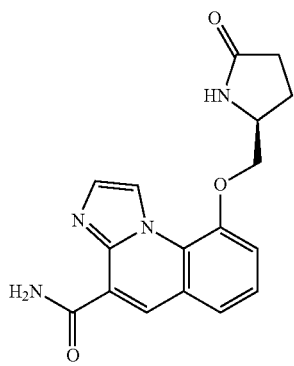
(1)

Intermediate 1A:
(3-methoxy-2-nitrophenyl)methanol

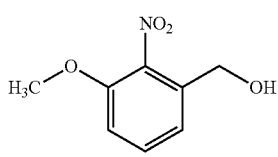
(1A)

To a solution of 3-methoxy-2-nitrobenzoic acid (5.0 g, 25.4 mmol) in THF (150 mL) was added borane dimethyl sulfide complex (2.31 g, 30.4 mmol) at 0° C. The reaction mixture was allowed to warm to room temperature and heated at reflux for 1 h. The reaction mixture was cooled to room temperature and quenched with 1.5 N HCl. The resulting solution was extracted with ethyl acetate and the combined organic extracts were washed with 10% sodium bicarbonate solution, dried over anhydrous sodium sulphate, and concentrated under reduced pressure to provide (3-methoxy-2-nitrophenyl)methanol (3.4 g, 73% yield) as a pale yellow oil which crystallized over time. ¹H NMR (400 MHz, DMSO-d₆) δ 7.56-7.48 (m, 1H), 7.23 (d, J=7.5 Hz, 1H), 7.17-7.11 (m, 1H), 5.51-5.45 (m, 1H), 4.48 (d, J=5.5 Hz, 2H), 3.87 (s, 3H).

Intermediate 1B: 3-methoxy-2-nitrobenzaldehyde

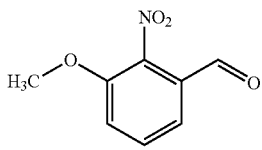
(1B)

To a stirred solution of (3-methoxy-2-nitrophenyl)methanol (3.4 g, 18.6 mmol) in DCM (25 mL) was added celite followed by PCC (6.0 g, 27.8 mmol) at room temperature. The reaction mixture was stirred at room temperature for 2 h. The reaction mixture was filtered and concentrated to afford a brown solid. The crude compound was purified by column chromatography (silica gel column, 0-20% ethyl acetate in pet-ether) to provide 3-methoxy-2-nitrobenzaldehyde (2.6 g, 77% yield) as a white crystalline solid. ¹H NMR (300 MHz, DMSO-d₆) δ 9.94 (s, 1H), 7.93-7.58 (m, 3H), 3.94 (s, 3H). LC-MS: m/z 182.1 (M+H).

Intermediate 1C: ethyl 2-cyano-3-(3-methoxy-2-nitrophenyl)acrylate

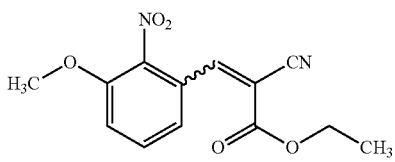
(1C)

To a stirred solution of ethyl 2-cyanoacetate (2.81 g, 24.84 mmol) in ethanol (45 mL) were added piperidine (0.212 g, 2.48 mmol) followed by 3-methoxy-2-nitrobenzaldehyde (4.5 g, 24.8 mmol) at room temperature. The reaction mixture was heated at 80° C. for 2.5 h and cooled to room temperature. The solvent was evaporated under reduced pressure and the residue was triturated with hexane. The precipitated solid was filtered and dried under reduced pressure to provide ethyl 2-cyano-3-(3-methoxy-2-nitrophenyl)acrylate (6.5 g, 95% yield) as an off-white solid. ¹H NMR (300 MHz, DMSO-d₆) δ 8.20 (s, 1H), 7.87-7.74 (m, 1H), 7.71-7.57 (m, 2H), 4.33 (q, J=7.2 Hz, 2H), 3.96 (s, 3H), 1.30 (t, J=7.2 Hz, 3H). LC-MS: m/z 277 (M+H).

Intermediate 1D: ethyl 2-amino-8-methoxyquinoline-3-carboxylate

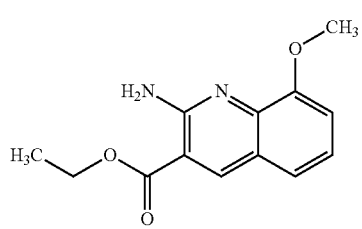
(1D)

To a stirred solution of ethyl 2-cyano-3-(3-methoxy-2-nitrophenyl)acrylate (1.05 g, 3.8 mmol) in a mixture of AcOH (2 mL, 34.9 mmol) and ethanol (10 mL) was added iron powder (0.425 g, 7.6 mmol). The suspension was cooled to 0° C. and concentrated HCl (0.1 mL, 1.100 mmol) was added. The reaction mixture was heated at 80° C. for 45 minutes and cooled to room temperature. The mixture was filtered, washed with ethanol, and concentrated under reduced pressure afford the crude compound which was diluted with ethyl acetate and neutralized using 10% sodium bicarbonate solution. The organic layer was separated and the aqueous layer was extracted with chloroform. The combined organic extracts were dried over anhydrous sodium sulphate and evaporated under reduced pressure to provide ethyl 2-amino-8-methoxyquinoline-3-carboxylate (400 mg, 43% yield) as a pale yellow solid. $^1$H NMR (400 MHz, DMSO-$d_6$) δ 7.56-7.48 (m, 1H), 7.23 (d, J=7.5 Hz, 1H), 7.17-7.11 (m, 1H), 5.51-5.45 (m, 1H), 4.48 (d, J=5.5 Hz, 2H), 3.87 (s, 3H). LC-MS: m/z 247.2 (M+H).

Intermediate 1E: ethyl 9-methoxyimidazo[1,2-a]quinoline-4-carboxylate

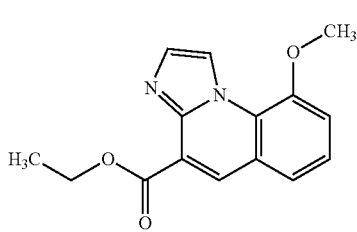

(1E)

To a stirred suspension of ethyl 2-amino-8-methoxyquinoline-3-carboxylate (400 mg, 1.62 mmol) in ethanol (15 mL) were added 2-chloroacetaldehyde (153 mg, 1.95 mmol) followed by sodium bicarbonate (273 mg, 3.25 mmol) at room temperature. The reaction mixture was heated at 85° C. for 16 h and cooled to room temperature. The reaction mixture was filtered through celite and washed with ethanol. The filtrate was evaporated under reduced pressure to afford the crude product. The crude compound was purified by column chromatography (silica gel column, 0-2% methanol in chloroform) to provide ethyl 9-methoxyimidazo[1,2-a]quinoline-4-carboxylate (350 mg, 80% yield) as a pale brown syrup. $^1$H NMR (400 MHz, DMSO-$d_6$) δ 8.98 (d, J=1.5 Hz, 1H), 8.24 (s, 1H), 7.73 (dd, J=7.5, 1.5 Hz, 1H), 7.66 (d, J=1.5 Hz, 1H), 7.58-7.47 (m, 2H), 4.41 (q, J=7.0 Hz, 2H), 4.12 (s, 3H), 1.37 (t, J=7.0 Hz, 3H). LC-MS: m/z 271.2 (M+H).

Intermediate 1F: ethyl 9-methoxyimidazo[1,2-a]quinoline-4-carboxamide

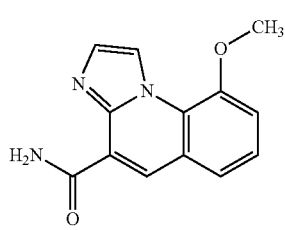

(1F)

To a methanolic solution of ammonia (15 mL, 690 mmol) was added ethyl 9-methoxyimidazo[1,2-a]quinoline-4-carboxylate (150 mg, 0.56 mmol). The reaction vessel was sealed (pressure tube). The reaction mixture stirred at 25° C. overnight. The solvent was evaporated under reduced pressure to provide 9-methoxyimidazo[1,2-a]quinoline-4-carboxamide (75 mg, 56% yield) as an off-white solid. $^1$H NMR (400 MHz, DMSO-$d_6$) δ 9.79 (br. s., 1H), 9.02 (d, J=1.5 Hz, 1H), 8.47 (s, 1H), 8.06 (br. s., 1H), 7.78 (dd, J=8.0, 1.5 Hz, 1H), 7.71 (d, J=1.5 Hz, 1H), 7.60-7.49 (m, 2H), 4.13 (s, 3H).

Intermediate 1G: 9-hydroxyimidazo[1,2-a]quinoline-4-carboxamide

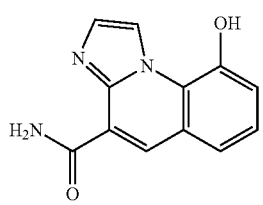

(1G)

To a stirred solution of 9-methoxyimidazo[1,2-a]quinoline-4-carboxamide (75 mg, 0.31 mmol) in DCM (2 mL) was added BBr$_3$ (5 mL, 5.0 mmol, 1.0 M in DCM) at −78° C. The resulting mixture was stirred at the same temperature for 4 h. The reaction mixture was allowed to warm to room temperature over a period of 1 h and stirred at room temperature for 16 h. The reaction mixture was cooled to −78° C. The reaction was quenched with methanol. The reaction mixture was concentrated under reduced pressure to provide crude 9-hydroxyimidazo[1,2-a]quinoline-4-carboxamide (50 mg, 71% yield) as a pale brown solid along with a minor amount of unreacted starting material. $^1$H NMR (400 MHz, DMSO-$d_6$) δ 11.93 (br. s., 1H), 9.29 (d, J=2.0 Hz, 1H), 8.93-8.86 (m, 2H), 8.76 (br. s., 1H), 8.21-8.13 (m, 1H), 7.68-7.62 (m, 2H), 7.53 (dd, J=7.0, 2.0 Hz, 1H). LC-MS: m/z 228.2 (M+H).

Example 1: (S)-9-((5-oxopyrrolidin-2-yl)methoxy)imidazo[1,2-a]quinoline-4-carboxamide To a solution of 9-hydroxyimidazo[1,2-a]quinoline-4-carboxamide (50 mg, 0.22 mmol) and (S)-(5-oxopyrrolidin-2-yl)methyl 4-methylbenzenesulfonate (59.3 mg, 0.22 mmol) in DMF (2 mL) was added Cs$_2$CO$_3$ (143 mg, 0.44 mmol) at room temperature. The reaction mixture was heated at 65° C. for 1 h and cooled to room temperature. The reaction mixture was filtered through celite and the filtrate was concentrated under reduced pressure. The crude compound was purified by preparative HPLC to provide (S)-9-((5-oxopyrrolidin-2-yl)methoxy)imidazo[1,2-a]quinoline-4-carboxamide (10 mg, 0.03 mmol, 14% yield) as an off-white solid. $^1$H NMR (400 MHz, DMSO-$d_6$) δ 9.78 (br. s., 1H), 8.95 (d, J=1.5 Hz, 1H), 8.47 (s, 1H), 8.11-8.02 (m, 2H), 7.86-7.73 (m, 1H), 7.69 (d, J=1.5 Hz, 1H), 7.60-7.48 (m, 2H), 4.33-4.13 (m, 3H), 2.40-2.15 (m, 3H), 2.05-1.90 (m, 1H). LC-MS: m/z 325.1 (M+H).

Examples 2 and 3

9-(((2S,3R)-3-ethyl-5-oxopyrrolidin-2-yl)methoxy)imidazo[1,2-a]quinoline-4-carboxamide (2) and
9-(((2S,3S)-3-ethyl-5-oxopyrrolidin-2-yl)methoxy)imidazo[1,2-a]quinoline-4-carboxamide (3)

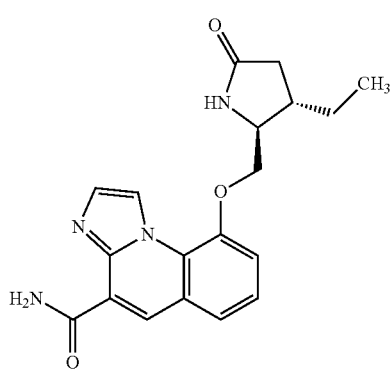

(2)

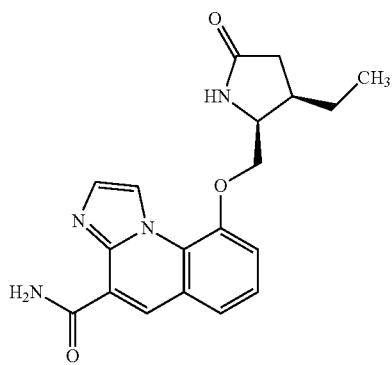

(3)

These compounds were synthesized according to the general procedure outlined in Example 1 using the appropriate intermediates.

Example 2: $^1$H NMR (400 MHz, DMSO-$d_6$) δ 9.78 (br. s., 1H), 8.96 (s, 1H), 8.46 (s, 1H), 8.13 (s, 1H), 8.04 (br. s., 1H), 7.80 (d, J=8.0 Hz, 1H), 7.68 (s, 1H), 7.55 (m, 2H), 4.36-4.30 (m, 2H), 4.20-4.12 (m, 1H), 2.31-2.21 (m, 1H), 2.17-2.04 (m, 1H), 1.70-1.57 (m, 2H), 1.45-1.28 (m, 1H), 0.92-0.83 (m, 3H). LC-MS: m/z 353.1 (M+H).

Example 3: $^1$H NMR (400 MHz, DMSO-$d_6$) δ 9.78 (br. s., 1H), 8.95 (s, 1H), 8.46 (s, 1H), 8.07 (s, 1H), 8.03 (s, 1H), 7.80 (d, J=8.1 Hz, 1H), 7.67 (s, 1H), 7.57 (dt, J=14.9, 7.6 Hz, 2H), 4.32-4.30 (m, 2H), 3.80-3.78 (m, 1H), 2.30-2.21 (m, 1H), 2.17-2.04 (m, 1H), 1.64-1.57 (m, 1H), 1.45-1.28 (m, 1H), 0.92-0.89 (m, 3H). LC-MS: m/z 353.1 (M+H).

Example 4

9-(((2S,3S,4R)-3-ethyl-4-fluoro-5-oxopyrrolidin-2-yl)methoxy)imidazo[1,2-a]quinoline-4-carboxamide

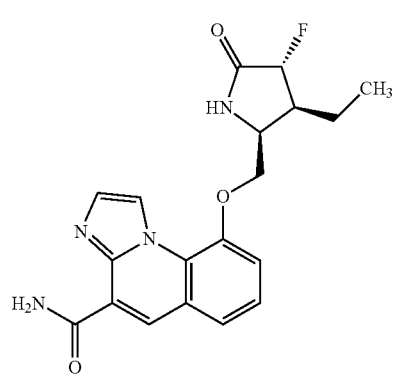

(4)

This compound was synthesized according to the general procedure outlined in Example 1 using the appropriate intermediates. $^1$H NMR (400 MHz, DMSO-$d_6$) δ 9.78 (br. s., 1H), 8.93-8.77 (m, 2H), 8.48 (br. s., 1H), 8.10-7.98 (m, 1H), 7.81 (dd, J=7.2, 1.8 Hz, 1H), 7.72-7.62 (m, 1H), 7.62-7.48 (m, 2H), 5.22-4.84 (m, 1H), 4.43-4.27 (m, 2H), 4.27-4.16 (m, 1H), 2.65 (m, 1H) 1.81-1.47 (m, 2H), 1.06-0.87 (m, 3H). $^{19}$F NMR (376.564 MHz, DMSO-$d_6$) δ −192.55. LC-MS: m/z 371.5 (M+H).

Example 5

9-(((2S,3S,4S)-3-ethyl-4-fluoro-5-oxopyrrolidin-2-yl)methoxy)imidazo[1,2-a]quinoline-4-carboxamide

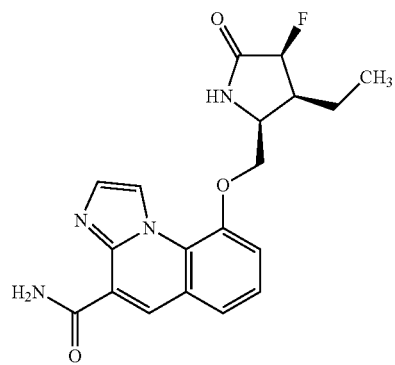

(5)

This compound was synthesized according to the general procedure outlined in Example 1 using the appropriate intermediates. $^1$H NMR (400 MHz, DMSO-$d_6$) δ 9.80 (br. s., 1H), 9.00-8.96 (m, 2H), 8.47 (s, 1H), 8.05 (s, 1H), 7.80 (d, J=8.0 Hz, 1H), 7.68 (s, 1H), 7.52 (m, 2H), 4.98-4.83 (m, 1), 4.38-4.22 (m, 3H), 2.21 (m, 1H), 1.60-1.60 (m, 2H), 0.90 (t, J=7.2 Hz, 3H). LC-MS: m/z 371.1 (M+H).

Example 6

9-(((2S,3S,4S)-3-ethyl-4-fluoro-4-methyl-5-oxopyrrolidin-2-yl)methoxy)imidazo[1,2-a]quinoline-4-carboxamide

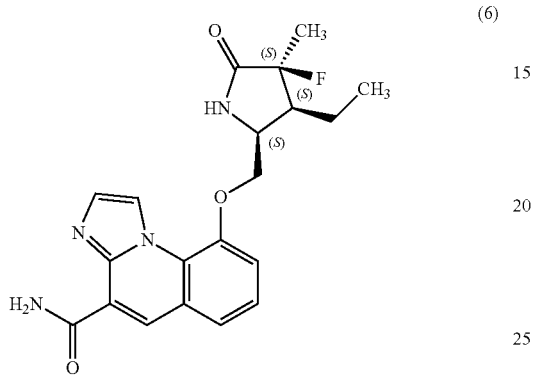

(6)

This compound was synthesized according to the general procedure outlined in Example 1 using the appropriate intermediates. $^1$H NMR (400 MHz, DMSO-$d_6$) δ 9.35 (br. s., 1H), 9.05 (d, J=1.7 Hz, 1H), 8.89 (s, 1H), 8.62 (s, 1H), 8.08 (br. s., 1H), 7.86-7.77 (m, 2H), 7.74 (d, J=8.3 Hz, 1H), 7.64 (t, J=7.9 Hz, 1H), 4.43-4.20 (m, 3H), 2.78-2.60 (m, 1H), 1.73-1.55 (m, 2H), 1.46 (d, J=24.0 Hz, 3H), 0.99 (t, J=7.3 Hz, 3H). LC-MS: m/z 385.1 (M+H).

Example 7

(R)-9-((5-oxomorpholin-3-yl)methoxy)imidazo[1,2-a]quinoline-4-carboxamide

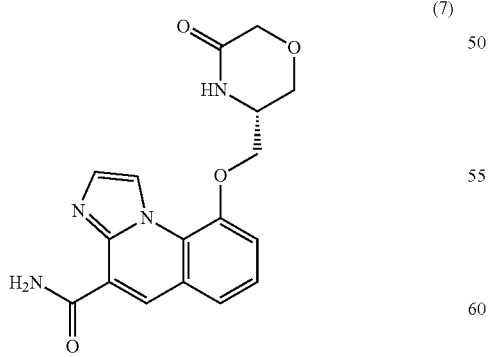

(7)

This compound was synthesized according to the general procedure outlined in Example 1 using the appropriate intermediates. $^1$H NMR (400 MHz, DMSO-$d_6$) δ 9.72-9.53 (m, 1H), 9.03 (s, 1H), 8.53 (s, 1H), 8.40 (d, J=2.4 Hz, 1H), 8.12-8.04 (m, 1H), 7.88-7.67 (m, 2H), 7.67-7.53 (m, 2H), 4.50-4.22 (m, 2H), 4.13-3.86 (m, 5H). LC-MS: m/z 341.2 (M+H).

Example 10

9-(((2S,3S)-3-ethyl-4,4-difluoro-5-oxopyrrolidin-2-yl)methoxy)imidazo[1,2-a]quinoline-4-carboxamide

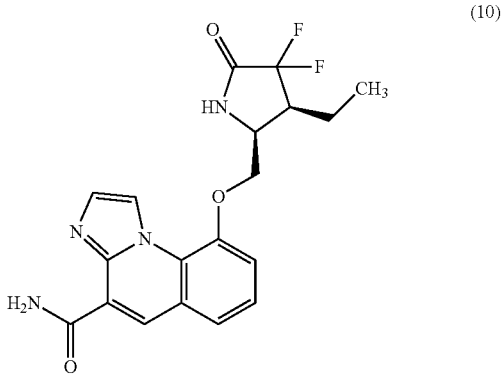 [SMILES: CC[C@H]1[C@@H](COc2cccc3cc(C(N)=O)c4nccn4c23)NC(=O)C1(F)F]

(10)

This compound was synthesized according to the general procedure outlined in Example 1 using the appropriate intermediates. $^1$H NMR (400 MHz, DMSO-$d_6$) δ 9.55 (s, 1H), 8.98 (s, 1H), 8.46 (s, 1H), 8.54 (s, 1H), 8.07 (br. s., 1H), 7.80 (d, J=7.2 Hz, 1H), 7.74 (s, 1H), 7.69-7.67 (m, 1H), 7.61-7.57 (m, 1H), 4.40-4.37 (m, 2H), 4.28-4.26 (m, 1H), 2.91-2.87 (m, 1H), 1.70-1.57 (m, 2H), 1.74-1.69 (m, 2H), 1.02 (t, J=7.2 Hz, 3H). LC-MS: m/z 389.3 (M+H).

Example 11

9-(((2S,3R)-3-ethyl-5-oxopyrrolidin-2-yl)methoxy)-2-methylimidazo[1,2-a]quinoline-4-carboxamide

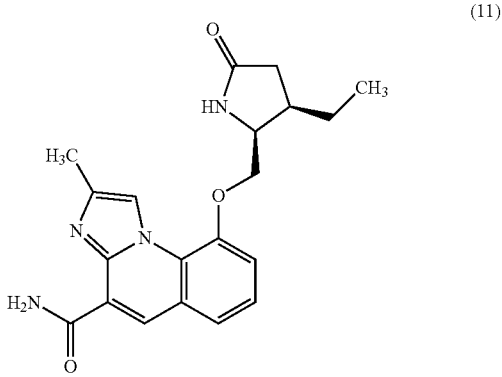

(11)

Intermediate 11A: ethyl 9-methoxy-2-methylimidazo[1,2-a]quinoline-4-carboxylate

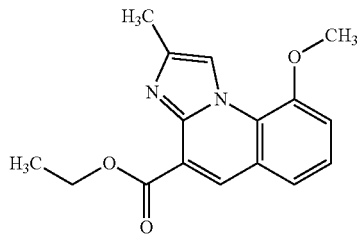

(11A)

To a solution of ethyl 2-amino-8-methoxyquinoline-3-carboxylate (0.15 g, 0.61 mmol) in ethanol (1 mL) was added chloroacetone (0.113 g, 1.22 mmol). The reaction mixture was heated at 90° C. for 12 h. The reaction mixture was cooled to room temperature and concentrated. The mixture was purified by column chromatography (Silica gel, 8% methanol in chloroform) to provide ethyl 9-methoxy-2-methylimidazo[1,2-a]quinoline-4-carboxylate (0.1 g, 58% yield) as an off-white solid. LC-MS: m/z 285.4 (M+H).

Intermediate 11B: 9-methoxy-2-methylimidazo[1,2-a]quinoline-4-carboxamide

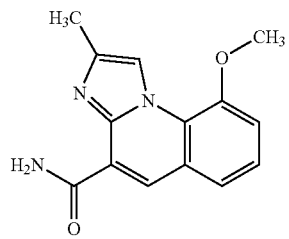

(11B)

In a sealed tube, ammonia gas (5 mL, 230 mmol) was purged in MeOH (5 mL) for 10 min and ethyl 9-methoxy-2-methylimidazo[1,2-a]quinoline-4-carboxylate (0.1 g, 0.35 mmol) was added. The pressure tube was closed. The reaction mixture was stirred at room temperature for 12 h. The reaction mixture was concentrated under reduced pressure to afford 9-methoxy-2-methylimidazo[1,2-a]quinoline-4-carboxamide (0.085 g, 95% yield) as an off-white solid. LC-MS: m/z 256.2 (M+H).

Intermediate 11C: Preparation of 9-hydroxy-2-methylimidazo[1,2-a]quinoline-4-carboxamide

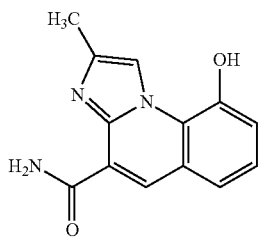

(11C)

To a stirred solution of 9-methoxy-2-methylimidazo[1,2-a]quinoline-4-carboxamide (0.085 g, 0.333 mmol) in DCM (10 mL) was added BBr$_3$ (1.67 mL, 1.67 mmol) at −78° C. The reaction mixture was allowed to come to room temperature and was stirred for 12 h. The reaction mixture was cooled to 0° C., diluted with 10 mL of methanol, and stirred for 10 min. The solvent was evaporated under reduced pressure to afford 9-hydroxy-2-methylimidazo[1,2-a]quinoline-4-carboxamide (0.08 g, 87% yield) as a pale yellow solid. $^1$H NMR (300 MHz, DMSO-d$_6$) δ 11.78 (br. s., 1H), 9.10 (s, 1H), 8.77 (s, 2H), 8.11 (br. s., 1H), 7.67-7.58 (m, 2H), 7.55-7.44 (m, 1H), 2.54 (s, 3H). LC-MS: m/z 242.2 (M+H).

Example 11: 9-(((2S,3R)-3-ethyl-5-oxopyrrolidin-2-yl)methoxy)-2-methylimidazo[1,2-a]quinoline-4-carboxamide This compound was synthesized according to the general procedure outlined in Example 1 using the appropriate intermediates. $^1$H NMR (400 MHz, DMSO-d$_6$) δ 0.88 (t, J=7.28 Hz, 3H) 1.18-1.41 (m, 2H) 1.61 (d, J=7.53 Hz, 1H) 2.09 (dd, J=16.56, 10.54 Hz, 1H) 2.24-2.35 (m, 1H) 2.45 (d, J=1.00 Hz, 3H) 4.09-4.16 (m, 1H) 4.24 (dd, J=10.04, 4.52 Hz, 1H) 4.40 (dd, J=10.04, 5.52 Hz, 1H) 7.45-7.61 (m, 2H) 7.77 (dd, J=7.53, 1.00 Hz, 1H) 8.01 (d, J=3.01 Hz, 1H) 8.16 (s, 1H) 8.40 (s, 1H) 8.66 (d, J=1.00 Hz, 1H) 9.82 (d, J=3.01 Hz, 1H). LC-MS: m/z 367.2 (M+H).

Example 12

9-(((2S,3S,4S)-3-ethyl-4-fluoro-5-oxopyrrolidin-2-yl)methoxy)-2-methylimidazo[1,2-a]quinoline-4-carboxamide

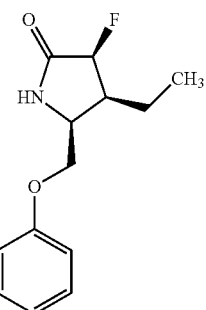

(12)

This compound was synthesized according to the general procedure outlined in Example 11 using the appropriate intermediates. $^1$H NMR (400 MHz, DMSO-d$_6$) δ 1.00 (t, J=7.28 Hz, 3H) 1.55-1.67 (m, 2H) 2.46 (d, J=1.00 Hz, 4H) 4.21-4.34 (m, 3H) 4.83-4.91 (m, 1H) 4.96-5.04 (m, 1H) 7.51 (d, J=7.53 Hz, 2H) 7.76-7.80 (m, 1H) 7.98-8.06 (m, 1H) 8.41 (s, 1H) 8.73 (s, 1H) 8.97-9.04 (m, 1H) 9.80-9.87 (m, 1H). LC-MS: m/z 385.4 (M+H).

Example 13

9-(((2S,3S,4S)-3-ethyl-4-fluoro-5-oxopyrrolidin-2-yl)methoxy)-2-(2-hydroxypropan-2-yl)imidazo[1,2-a]quinoline-4-carboxamide

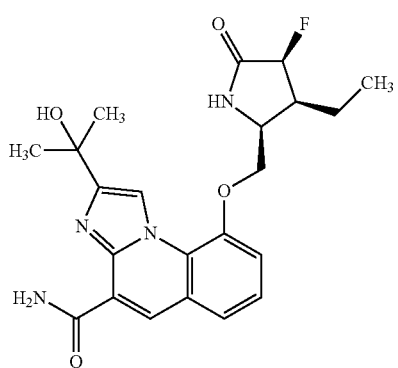
(13)

Intermediate 13A:
2-amino-8-methoxyquinoline-3-carboxamide

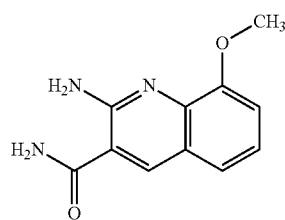
(13A)

Ammonia gas was purged into methanol (50 mL) for 15 min in a pressure tube and ethyl 2-amino-8-methoxyquinoline-3-carboxylate (1.0 g, 4.06 mmol) was added. The pressure tube was closed. The reaction mixture was stirred at room temperature for 48 h. The reaction mixture was concentrated under reduced pressure and the crude compound was purified by column chromatography (silica gel, 8% methanol in chloroform) provide 2-amino-8-methoxyquinoline-3-carboxamide (0.5 g, 53% yield) as an off-white solid. LC-MS: m/z 218.2 (M+H).

Intermediate 13B: ethyl 4-carbamoyl-9-methoxyimidazo[1,2-a]quinoline-2-carboxylate

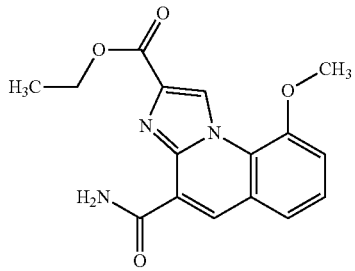
(13B)

To a solution of 2-amino-8-methoxyquinoline-3-carboxamide (0.5 g, 2.30 mmol) in ethanol (30 mL) was added ethyl 3-bromo-2-oxopropanoate (0.54 g, 2.76 mmol) followed by sodium bicarbonate (0.39 g, 4.6 mmol). The reaction mixture was heated at 85° C. for 2 h. The reaction mixture was cooled to room temperature and the solvent was evaporated under reduced pressure. The crude material was purified by column chromatography (silica gel, 8% methanol in chloroform) to provide ethyl 4-carbamoyl-9-methoxy-imidazo[1,2-a]quinoline-2-carboxylate (0.25 g, 35% yield). LC-MS: m/z 314.2 (M+H).

Intermediate 13C: 2-(2-hydroxypropan-2-yl)-9-methoxyimidazo[1,2-a]quinoline-4-carboxamide

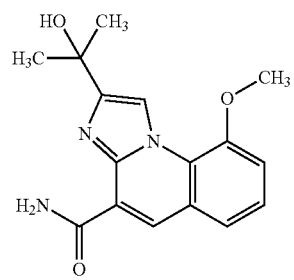
(13C)

To a solution of ethyl 4-carbamoyl-9-methoxyimidazo[1,2-a]quinoline-2-carboxylate (0.2 g, 0.638 mmol) in THF (10 mL) was added methyl magnesium bromide (2.13 mL, 6.38 mmol) at −50° C. The reaction mixture was allowed to warm to room temperature and stirred for 1 h. Dilute aqueous ammonium chloride solution was added and the mixture was extracted with ethyl acetate. The combined organic extracts were dried over anhydrous sodium sulphate and concentrated under reduced pressure. The crude compound was purified by column chromatography (silica gel, 8% methanol in chloroform) provide 2-(2-hydroxypropan-2-yl)-9-methoxyimidazo[1,2-a]quinoline-4-carboxamide (0.06 g, 31% yield) as an off-white solid. LC-MS: m/z 300.1 (M+H).

Intermediate 13D: 9-hydroxy-2-(2-hydroxypropan-2-yl)imidazo[1,2-a]quinoline-4-carboxamide

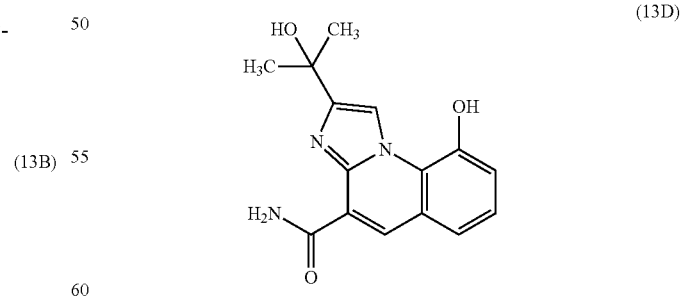
(13D)

To a stirred solution of 2-(2-hydroxypropan-2-yl)-9-methoxyimidazo[1,2-a]quinoline-4-carboxamide (0.054 g, 0.18 mmol) in DCM (5 mL) was added BBr₃ (0.36 mL, 0.36 mmol) at −78° C. The reaction mixture was allowed to come to room temperature and stirred for 12 h. The reaction mixture was diluted with sodium bicarbonate solution and extracted with dichloromethane. The combined organic extracts were dried over anhydrous sodium sulphate and concentrated to provide 9-hydroxy-2-(2-hydroxypropan-2-yl)imidazo[1,2-a]quinoline-4-carboxamide (0.037 g, 72% yield) as a pale yellow solid. LC-MS: m/z 386.2 (M+H).

Example 13: 9-(((2S,3S,4S)-3-ethyl-4-fluoro-5-oxopyrrolidin-2-yl)methoxy)-2-(2-hydroxypropan-2-yl)imidazo[1,2-a]quinoline-4-carboxamide This compound was synthesized according to the general procedure outlined in Example 11 using the appropriate intermediates. $^1$H NMR (400 MHz, DMSO-$d_6$) δ 9.87 (d, J=3.2 Hz, 1H), 8.84 (s, 1H), 8.78 (s, 1H), 8.42 (s, 1H), 8.01 (br. s., 1H), 7.77 (d, J=7.6 Hz, 1H), 7.61-7.44 (m, 2H), 5.19 (br. s., 1H), 4.99-4.86 (d, J=5.4 Hz, 1H), 4.42-4.31 (m, 1H), 4.30-4.16 (m, 2H), 2.74-2.61 (m, 1H), 1.64 (dt, J=13.3, 6.7 Hz, 2H), 1.57 (d, J=9.5 Hz, 6H), 0.99 (t, J=7.3 Hz, 3H). LC-MS: m/z 429.2 (M+H).

Example 14

9-(((2S,3R)-3-ethyl-5-oxopyrrolidin-2-yl)methoxy)-6-fluoroimidazo[1,2-a]quinoline-4-carboxamide

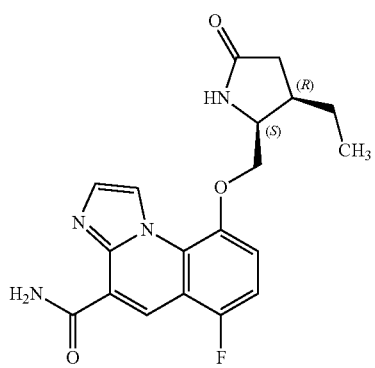

(14)

Intermediate 14A:
6-fluoro-3-methoxy-2-nitrobenzonitrile

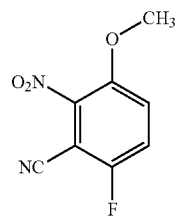

(14A)

To a stirred solution of 2-fluoro-5-methoxybenzonitrile (4 g, 26.5 mmol) in acetic anhydride (40 mL, 420 mmol) was added nitric acid (15 mL, 336 mmol) drop wise at 0° C. The resulting solution was stirred at the same temperature for 40 min. The mixture was poured into ice and stirred for 10 min. The solution was extracted with ethyl acetate. The combined organic extracts were washed with water, brine, dried over anhydrous sodium sulphate, and evaporated under reduced pressure to afford 6-fluoro-3-methoxy-2-nitrobenzonitrile (3.8 g, 73% yield) as a yellow solid. $^1$H NMR (400 MHz, DMSO-$d_6$) ppm 7.33-7.43 (m, 2H) 3.99 (s, 1H).

Intermediate 14B:
6-fluoro-3-methoxy-2-nitrobenzaldehyde

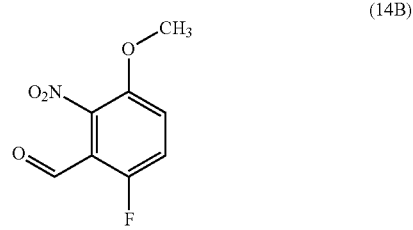

(14B)

To a stirred solution of 6-fluoro-3-methoxy-2-nitrobenzonitrile (4 g, 20.4 mmol) in toluene (120 mL) was added DIBAL-H (1 M in heptane) (40.8 mL, 40.8 mmol) at −78° C. under argon atmosphere. The reaction mixture was stirred at −78° C. for 1 h. The reaction was quenched with the addition of aqueous 1.5 N HCl solution. The reaction mixture was extracted with ethyl acetate. The combined organic extracts were washed with water, brine, dried over anhydrous sodium sulphate and, evaporated under reduced pressure to afford the crude product. The crude material was purified by column chromatography (Silica gel, 40% ethyl acetate in pet ether) to provide 6-fluoro-3-methoxy-2-nitrobenzaldehyde (3.5 g, 86% yield) as a pale yellow solid. $^1$H NMR (400 MHz, chloroform-d) δ 10.25 (s, 1H) 7.30-7.40 (m, 2H) 3.90-3.96 (m, 4H).

Intermediate 14C:
2-amino-6-fluoro-3-methoxybenzaldehyde

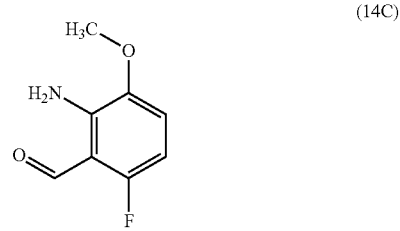

(14C)

To a stirred solution of 6-fluoro-3-methoxy-2-nitrobenzaldehyde (1.5 g, 7.53 mmol) in ethanol (20 mL) and acetic acid (6 mL) were added iron (0.841 g, 15.1 mmol) followed by HCl (2 mL, 65.8 mmol, concentrated) at room temperature. The reaction mixture was heated at 80° C. for 1 h. After cooling room temperature, the mixture was filtered through celite and washed with ethanol. The filtrate was evaporated under reduced pressure and the residue was diluted with saturated aqueous sodium bicarbonate and extracted with ethyl acetate. The combined organic extracts were washed with water, brine, dried over anhydrous sodium sulphate and evaporated under reduced pressure to provide 2-amino-6-fluoro-3-methoxybenzaldehyde (1.2 g, 31% yield). LC-MS: m/z 170.2 (M+H).

Intermediate 14D: Preparation of 2-amino-5-fluoro-8-methoxyquinoline-3-carboxamide

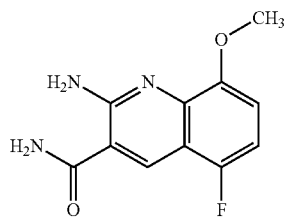

(14D)

To a solution of 2-amino-6-fluoro-3-methoxybenzaldehyde (800 mg, 4.73 mmol) in ethanol (5 mL) was added 2-cyanoacetamide (398 mg, 4.73 mmol) at room temperature. The reaction mixture was stirred for 5 min. Piperidine (0.047 mL, 0.47 mmol) was added and the reaction mixture was heated at 90° C. for 2 h. The reaction mixture was cooled to room temperature and volatiles were evaporated to dryness under reduced pressure. The residue was diluted with water and extracted with ethyl acetate. The combined organic extracts were washed with water, brine, dried over anhydrous sodium sulphate and concentrated. The crude product was purified by column chromatography (silica gel, 45% ethyl acetate in pet ether) to provide 2-amino-5-fluoro-8-methoxyquinoline-3-carboxamide (1.3 g, 61% yield) as a light brown solid. MS: m/z 236.4 (M+H).

Intermediate 14E: 6-fluoro-9-methoxyimidazo[1,2-a]quinoline-4-carboxamide

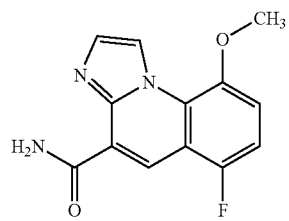

(14E)

To a stirred solution of 2-amino-5-fluoro-8-methoxyquinoline-3-carboxamide (500 mg, 2.13 mmol) and sodium bicarbonate (357 mg, 4.25 mmol) in ethanol (10 mL) was added 2-chloroacetaldehyde (50% in water, 1 g, 6.38 mmol). The reaction mixture was heated at 95° C. for 14 h. The reaction mixture was cooled to room temperature and evaporated to dryness under reduced pressure. The residue was diluted with water and extracted with ethyl acetate. The combined organic extracts were washed with water, brine, dried over anhydrous sodium sulphate and concentrated. The crude compound was purified by column chromatography (silica gel, 52% ethyl acetate in pet ether) to provide 6-fluoro-9-methoxyimidazo[1,2-a]quinoline-4-carboxamide (300 mg, 45% yield). MS: m/z 260.1 (M+H).

Intermediate 14F: 6-fluoro-9-hydroxyimidazo[1,2-a]quinoline-4-carboxamide

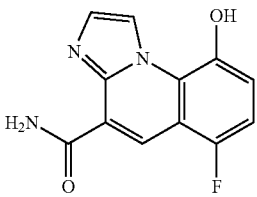

(14F)

To a stirred solution of 6-fluoro-9-methoxyimidazo[1,2-a]quinoline-4-carboxamide (300 mg, 1.16 mmol) in dichloromethane (15 mL) was added BBr$_3$ (1 M in DCM) (11.6 mL, 11.6 mmol) at −78° C. The reaction mixture was allowed to warm room temperature and stirred for 16 h. The reaction mixture was cooled to 0° C. The reaction was quenched with the slow addition of methanol. The reaction mixture was stirred for an additional 20 min. The volatiles were evaporated under reduced pressure to afford 6-fluoro-9-hydroxyimidazo[1,2-a]quinoline-4-carboxamide (400 mg, crude) as a pale yellow solid. MS: m/z 246.1 (M+H).

Example 14: 9-(((2S,3R)-3-ethyl-5-oxopyrrolidin-2-yl)methoxy)-6-fluoroimidazo[1,2-a]quinoline-4-carboxamide This compound was synthesized according to the general procedure outlined in Example 1 using the appropriate intermediates. $^1$H NMR (400 MHz, DMSO-d$_6$) δ 9.74 (br. s., 1H) 8.99 (s, 1H) 8.46 (s, 1H) 8.06-8.21 (m, 2H) 7.67-7.81 (m, 1H) 7.55-7.64 (m, 1H) 7.41-7.51 (m, 1H) 4.26-4.38 (m, 2H) 4.14 (q, J=6.28 Hz, 1H) 2.21-2.38 (m, 2H) 2.00-2.15 (m, 1H) 1.55-1.72 (m, 1H) 1.26-1.47 (m, 1H) 0.80-0.95 (m, 3H). LC-MS: m/z 371.2 (M+H).

Example 15

9-(((2S,3S,4S)-3-ethyl-4-fluoro-5-oxopyrrolidin-2-yl)methoxy)-6-fluoroimidazo[1,2-a]quinoline-4-carboxamide

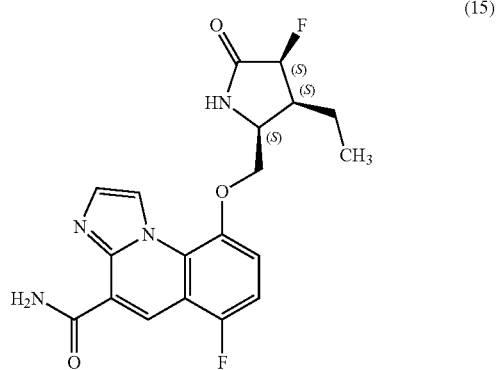

(15)

This compound was synthesized according to the general procedure outlined in Example 1 using the appropriate intermediates. $^1$H NMR (400 MHz, DMSO-d$_6$) δ 9.76 (br. s., 1H), 9.02 (d, J=1.5 Hz, 1H), 8.96 (s, 1H), 8.45 (s, 1H), 8.14

(br. s., 1H), 7.59 (dd, J=9.2, 5.0 Hz, 1H), 7.48-7.39 (m, 1H), 4.97 (d, J=5.9 Hz, 1H), 4.84 (d, J=5.6 Hz, 1H), 4.37-4.31 (m, 1H), 4.27-4.10 (m, 3H), 2.94-2.88 (m, 1H), 1.66-1.55 (m, 2H), 1.24 (dd, J=11.4, 5.0 Hz, 1H), 1.15 (t, J=7.3 Hz, 2H), 1.01-0.90 (m, 3H). LC-MS: m/z 389.2 (M+H).

Example 16

1-(((2S,3R)-3-ethyl-5-oxopyrrolidin-2-yl)methoxy)imidazo[1,2-a][1,7]naphthyridine-6-carboxamide

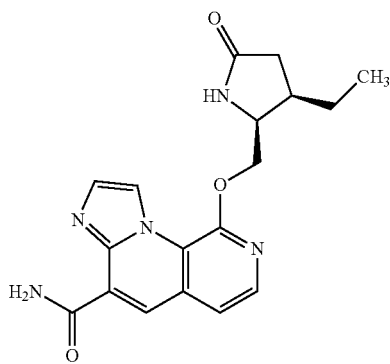

Intermediate 16A:
1H-pyrrolo[3,4-c]pyridine-1,3(2H)-dione

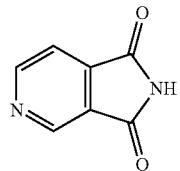

A stirred solution of pyridine-3,4-dicarboxylic acid (100 g, 600 mmol) in Ac$_2$O (160 mL, 170 mmol) was heated at 140° C. for 16 h and cooled to room temperature. The solvent was evaporated under reduced pressure to yield a crude mixture. Acetamide (53.0 g, 900 mmol) was added and the resulting mixture was heated at 140° C. for 8 h. The mixture was cooled to room temperature, diluted with hot water, and stirred for 30 min. The precipitated solid was filtered and dried to provide 1H-pyrrolo[3,4-c]pyridine-1,3(2H)-dione (60 g, 68% yield) as a pale yellow solid. LC-MS: m/z 149.1 (M+H).

Intermediate 16B: 3-aminoisonicotinic acid

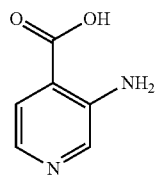

To a solution of NaOH (120 g, 3000 mmol) in water (1.2 L) was added bromine (10.5 mL, 203 mmol) drop wise at 0° C. The reaction mixture was stirred at the same temperature for 30 min. 1H-pyrrolo[3,4-c]pyridine-1,3(2H)-dione (30 g, 203 mmol) was added to the reaction mixture portion wise at 0° C. The reaction mixture was allowed to warm to room temperature and then heated at 80° C. for 8 h. The reaction mixture was cooled to 0° C. and acidified with acetic acid (130 mL). The precipitated solid was filtered, washed with water (100 mL), dried in vacuo to afford 3-aminoisonicotinic acid (20 g, 72% yield) as a pale yellow solid. LC-MS: m/z 139.1 (M+H).

Intermediate 16C: ethyl 3-aminoisonicotinate

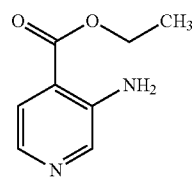

To a solution of 3-aminoisonicotinic acid (25 g, 181 mmol) in ethanol (250 mL) was added sulfuric acid (9.65 mL, 181 mmol) dropwise at 0° C. The reaction mixture was stirred at 95° C. for 16 h and cooled to room temperature. The solvent was removed under reduced pressure and the residue was diluted with water, basified with aqueous 10% NaHCO$_3$ solution, and extracted with ethyl acetate. The combined organic extracts were dried over anhydrous Na$_2$SO$_4$ and concentrated to provide ethyl 3-aminoisonicotinate (12 g, 40% yield) as an off-white solid. LC-MS: m/z 167.2 (M+H).

Intermediates 16D1 and 16D2: ethyl
3-amino-2-chloroisonicotinate (16D1) and ethyl
3-amino-2,6-dichloroisonicotinate (16D2)

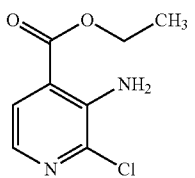

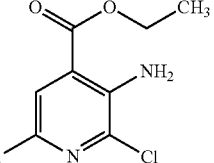

To a solution of ethyl 3-aminoisonicotinate (7 g, 42.1 mmol) in HCl (70 mL, 2.3 mol) was added H$_2$O$_2$ (5.16 mL, 84 mmol) drop wise at 0° C. The reaction mixture was stirred at room temperature for 1 h. The reaction was quenched with the addition of saturated aqueous NaHCO$_3$ solution. The reaction mixture was extracted with ethyl acetate. The combined organic extracts were dried over anhydrous Na₂SO₄ and concentrated. The crude material was purified by column chromatography (silica gel, 3.5% ethyl acetate in pet-ether) to provide ethyl 3-amino-2-chloroisonicotinate (3 g, 36% yield). ¹H NMR (300 MHz, DMSO-d₆) δ 7.70-7.54 (m, 2H), 6.78 (br. s., 2H), 4.33 (q, J=7.2 Hz, 2H), 1.32 (t, J=7.2 Hz, 3H) and ethyl 3-amino-2,6-dichloroisonicotinate (3.5 g, 35% yield) as an off-white solid. LC-MS: m/z 201.1 (M+H).

Intermediate 16E:
(3-amino-2-chloropyridin-4-yl)methanol

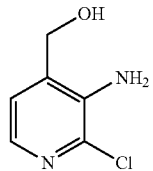
(16E)

To a stirred solution of ethyl 3-amino-2-chloroisonicotinate (3 g, 15 mmol) in tetrahydrofuran (40 mL) was added LAH (6.23 mL, 15 mmol) at −78° C. over a period of 5 min. The resulting reaction mixture was stirred at the same temperature for 15 min and then allowed to come to 0° C. and stirred for 30 min. The reaction was quenched with the addition of ethyl acetate followed by aqueous Na₂SO₄. The reaction mixture was extracted with ethyl acetate. The combined organic extracts were washed with water, dried over anhydrous Na₂SO₄ and concentrated to provide (3-amino-2-chloropyridin-4-yl)methanol as an off-white solid. LC-MS: m/z 159.1 (M+H).

Intermediate 16F:
3-amino-2-chloroisonicotinaldehyde

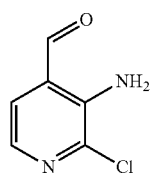
(16F)

To a stirred solution of (3-amino-2-chloropyridin-4-yl)methanol (2.1 g, 13.24 mmol) in DCM (20 mL) was added manganese dioxide (3.45 g, 39.7 mmol) at room temperature. The reaction mixture was stirred for 16 h. The reaction mixture was diluted with DCM and filtered through celite. The filtrate was concentrated and the crude compound was purified by column chromatography (silica gel, 25% ethyl acetate in pet ether) to provide 3-amino-2-chloroisonicotinaldehyde (1.2 g, 58% yield) as a colorless liquid. ¹H NMR (300 MHz, DMSO-d₆) δ 9.99 (s, 1H), 7.77 (d, J=4.9 Hz, 1H), 7.62 (d, J=4.9 Hz, 1H), 7.16 (br. s., 2H). LC-MS: m/z 157 (M+H).

Intermediate 16G:
2-amino-8-chloro-1,7-naphthyridine-3-carboxamide

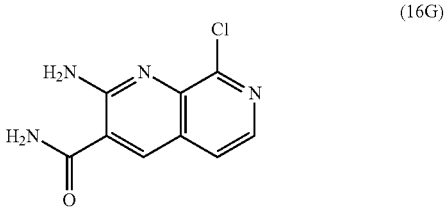 [SMILES: NC(=O)c1cc2ccnc(Cl)c2nc1N]
(16G)

To a stirred solution of 3-amino-2-chloroisonicotinaldehyde (0.15 g, 1 mmol) in ethanol (20 mL) was added 2-cyanoacetamide (0.081 g, 1 mmol) followed by piperidine (9.49 μL, 0.096 mmol) at room temperature. The reaction mixture was heated at 100° C. for 16 h and cooled to room temperature. The solvent was evaporated under reduced pressure and the residue was dissolved in water and extracted with ethyl acetate. The combined organic extracts were dried over anhydrous Na₂SO₄ and concentrated. The crude compound was purified by column chromatography (silica gel, 3% MeOH in CHCl₃) to provide 2-amino-8-chloro-1,7-naphthyridine-3-carboxamide (0.15 g, 70% yield) as an off-white solid. LC-MS: m/z 223.4 (M+H).

Intermediate 16H: 1-chloroimidazo[1,2-a][1,7]naphthyridine-6-carboxamide

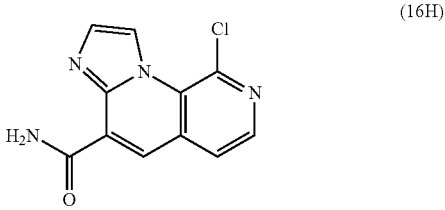 [SMILES: NC(=O)c1cc2ccnc(Cl)c2n2ccnc12]
(16H)

To a stirred solution of 2-amino-8-chloro-1,7-naphthyridine-3-carboxamide (0.15 g, 0.67 mmol) in DMF (5 mL) was added 2-chloroacetaldehyde (0.159 g, 2.02 mmol) at room temperature. The resulting reaction mixture was heated at 95° C. for 4 h and cooled to room temperature. The solvent was removed under reduced pressure and the residue was dissolved in water and extracted with ethyl acetate. The combined organic extracts were washed with aqueous NaHCO₃, dried over anhydrous Na₂SO₄, and concentrated. The crude obtained was purified by column chromatography (silica gel, 2% methanol in chloroform) to provide 1-chloroimidazo[1,2-a][1,7]naphthyridine-6-carboxamide (0.08 g, 48% yield) as a pale yellow solid. ¹H NMR (300 MHz, DMSO-d₆) δ 9.72 (s, 1H), 9.17 (s, 1H), 8.52-8.47 (m, 2H), 8.21 (d, J=4.9 Hz, 2H), 3.40 (s, 3H). LC-MS: m/z 247.2 (M+H).

Intermediate 161: 1-chloro-8-methylimidazo[1,2-a][1,7]naphthyridine-6-carboxamide

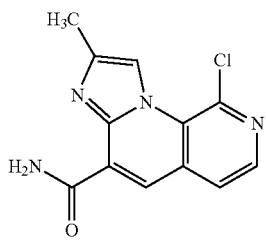
(16I)

To a stirred solution of 2-amino-8-chloro-1,7-naphthyridine-3-carboxamide (0.15 g, 0.674 mmol) in DMF (5 mL) was added 1-chloropropan-2-one (0.062 g, 0.674 mmol) at room temperature. The reaction mixture was heated at 95° C. for 4 h and cooled to room temperature. The solvent was removed under reduced pressure and the residue was dissolved in water and extracted with ethyl acetate. The combined organic extracts were washed with aqueous $NaHCO_3$ solution, dried over anhydrous $Na_2SO_4$ and concentrated. The product was purified by column chromatography (silica gel, 2% methanol in chloroform) to provide 1-chloro-8-methylimidazo[1,2-a][1,7]naphthyridine-6-carboxamide (0.08 g, 45% yield) as a pale yellow solid. $^1$H NMR (300 MHz, DMSO-$d_6$) δ 9.72 (s, 1H), 9.17 (s, 1H), 8.52-8.47 (m, 2H), 8.21 (d, J=4.9 Hz, 2H), 3.40 (s, 3H). LC-MS: m/z 261.1 (M+H).

Example 16: 1-(((2S,3R)-3-ethyl-5-oxopyrrolidin-2-yl)methoxy)imidazo[1,2-a][1,7]naphthyridine-6-carboxamide

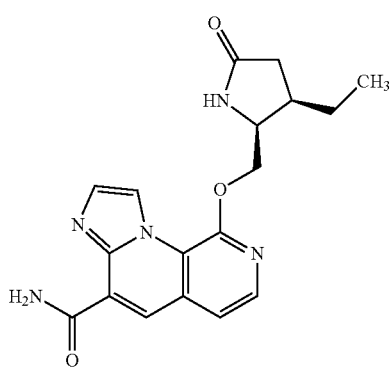
(16)

To a stirred solution of (4R,5S)-4-ethyl-5-(hydroxymethyl)pyrrolidin-2-one (0.017 g, 0.12 mmol) in DMF (2 mL) was added NaH (5.84 mg, 0.24 mmol) at 0° C. The reaction mixture was stirred for 10 min. Next, 1-chloroimidazo[1,2-a][1,7]naphthyridine-6-carboxamide (0.02 g, 0.08 mmol) was added to the reaction mixture and the resulting solution was heated at 80° C. for 2 h. The reaction was quenched with methanol and the reaction mixture was concentrated. The residue was dissolved in water and extracted with ethyl acetate. The combined organic extracts were dried over anhydrous $Na_2SO_4$ and concentrated. The crude compound was purified by prep-HPLC to provide 1-(((2S,3R)-3-ethyl-5-oxopyrrolidin-2-yl)methoxy)imidazo[1,2-a][1,7]naphthyridine-6-carboxamide as a pale yellow solid. $^1$H NMR (400 MHz, Methanol-$d_4$) δ 9.04-8.98 (m, 1H), 8.68 (s, 1H), 8.50 (s, 1H), 8.15-8.08 (m, 1H), 8.01 (s, 1H), 8.02-7.96 (m, 1H), 7.64-7.55 (m, 1H), 5.07-4.94 (m, 1H), 5.05-4.94 (m, 1H), 4.82-4.72 (m, 1H), 4.82-4.70 (m, 5H), 3.59-3.45 (m, 2H), 3.18-3.11 (m, 1H), 2.94-2.87 (m, 3H), 2.61-2.44 (m, 3H), 1.66-1.47 (m, 2H), 1.34-1.26 (m, 1H), 1.11 (t, J=7.3 Hz, 3H). LC-MS: m/z 354.2 (M+H).

Example 17

1-(((2S,3S,4S)-3-ethyl-4-fluoro-5-oxopyrrolidin-2-yl)methoxy)imidazo[1,2-a][1,7]naphthyridine-6-carboxamide

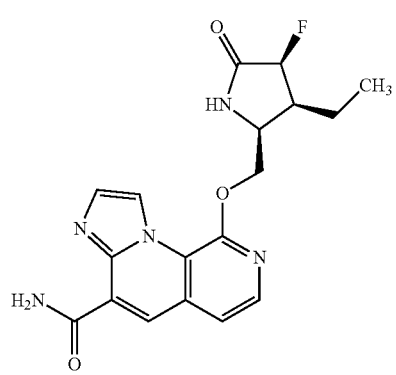
(17)

This compound was synthesized according to the general procedure outlined in Example 16 using the appropriate intermediates. $^1$H NMR (400 MHz, DMSO-$d_6$) δ 9.78-9.69 (m, 1H), 8.99-8.88 (m, 2H), 8.51-8.44 (m, 1H), 8.28-8.18 (m, 2H), 7.84-7.74 (m, 2H), 4.97-4.89 (m, 1H), 4.84-4.80 (m, 1H), 4.77-4.69 (m, 1H), 4.62-4.51 (m, 1H), 4.29-4.20 (m, 1H), 1.66-1.52 (m, 2H), 1.05-0.97 (m, 3H). LC-MS: m/z 372.1 (M+H).

Example 18

1-(((2S,3R)-3-ethyl-5-oxopyrrolidin-2-yl)methoxy)-8-methylimidazo[1,2-a][1,7]naphthyridine-6-carboxamide

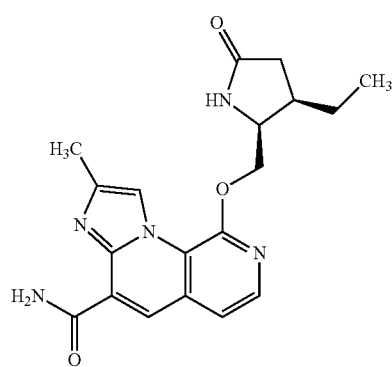
(18)

This compound was synthesized according to the general procedure outlined in Example 16 using the appropriate intermediates. ¹H NMR (400 MHz, DMSO-d$_6$) δ 9.81-9.74 (m, 1H), 8.63-8.58 (m, 1H), 8.41-8.36 (m, 1H), 8.22-8.09 (m, 3H), 7.78-7.68 (m, 1H), 4.84-4.75 (m, 1H), 4.59-4.46 (m, 1H), 4.18-4.09 (m, 1H), 3.22-3.10 (m, 1H), 2.70-2.63 (m, 1H), 2.37-2.20 (m, 1H), 2.13-2.01 (m, 1H), 1.67-1.51 (m, 1H), 1.39-1.27 (m, 1H), 1.25-1.20 (m, 1H), 0.93-0.83 (m, 3H). LC-MS: m/z 368.1 (M+H).

Example 19

1-(((2S,3S,4S)-3-ethyl-4-fluoro-5-oxopyrrolidin-2-yl)methoxy)-8-methylimidazo[1,2-a][1,7]naphthyridine-6-carboxamide

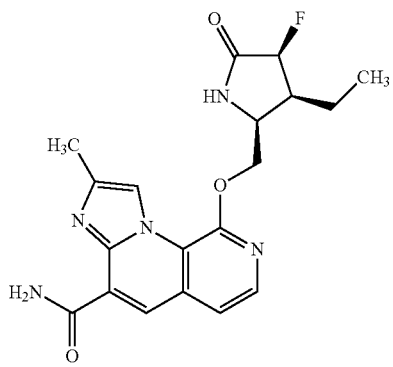

(19)

This compound was synthesized according to the general procedure outlined in Example 16 using the appropriate intermediates. ¹H NMR (400 MHz, DMSO-d$_6$) δ 9.85-9.66 (m, 1H), 8.97-8.92 (m, 1H), 8.72-8.65 (m, 1H), 8.44-8.35 (m, 1H), 8.25-8.12 (m, 2H), 7.80-7.67 (m, 1H), 4.99-4.92 (m, 1H), 4.86-4.76 (m, 1H), 4.71-4.55 (m, 2H), 4.34-4.16 (m, 1H), 1.64-1.48 (m, 2H), 1.07-0.94 (m, 3H). LC-MS: m/z 386.2 (M+H).

Example 20

1-(((2S,3S)-3-ethyl-4,4-difluoro-5-oxopyrrolidin-2-yl)methoxy)imidazo[1,2-a][1,7]naphthyridine-6-carboxamide

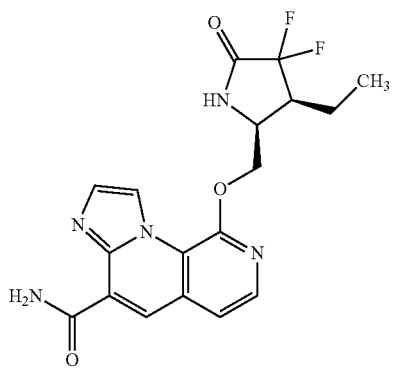

(20)

This compound was synthesized according to the general procedure outlined in Example 16 using the appropriate intermediates. ¹H NMR (400 MHz, DMSO-d$_6$) δ 1.05 (t, J=7.09 Hz, 3H) 1.64-1.72 (m, 2H) 2.82-2.94 (m, 1H) 4.36 (br. s., 1H) 4.58-4.67 (m, 1H) 4.73 (dd, J=11.37, 3.79 Hz, 1H) 7.78-7.83 (m, 2H) 8.21 (br. s., 1H) 8.25 (d, J=5.38 Hz, 1H) 8.49 (s, 1H) 8.92 (s, 1H) 9.47 (br. s., 1H) 9.70 (br. s., 1H). LC-MS: m/z 390.2 (M+H).

Example 21

1-(((2S,3S)-3-ethyl-4,4-difluoro-5-oxopyrrolidin-2-yl)methoxy)-8-methylimidazo[1,2-a][1,7]naphthyridine-6-carboxamide

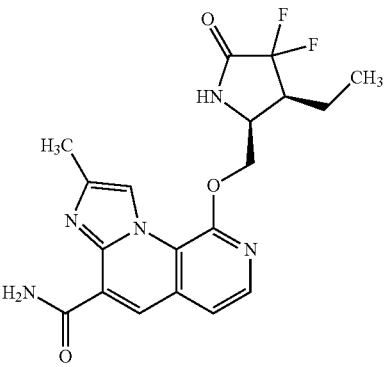

(21)

This compound was synthesized according to the general procedure outlined in Example 16 using the appropriate intermediates. ¹H NMR (400 MHz, DMSO-d$_6$) δ 1.04 (t, J=7.27 Hz, 3H) 1.66 (quin, J=7.46 Hz, 2H) 2.89 (td, J=16.23, 7.76 Hz, 1H) 4.04 (s, 1H) 4.37 (br. s., 1H) 4.60-4.73 (m, 2H) 7.76 (d, J=5.38 Hz, 1H) 8.20 (d, J=5.26 Hz, 1H) 8.41 (s, 1H) 8.63 (s, 1H) 9.51 (br. s., 1H) 9.78 (br. s., 1H). LC-MS: m/z 404.1 (M+H).

Example 22

1-(((4R,5S)-5-ethyl-2-oxooxazolidin-4-yl)methoxy)imidazo[1,2-a][1,7]naphthyridine-6-carboxamide

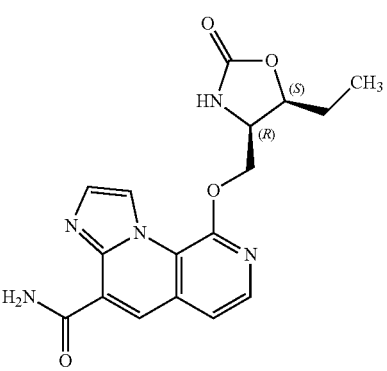

(22)

This compound was synthesized according to the general procedure outlined in Example 16 using the appropriate intermediates. ¹H NMR (400 MHz, DMSO-d₆) δ 9.70 (br. s., 1H), 8.92 (s, 1H), 8.48 (s, 1H), 8.26 (d, J=5.4 Hz, 1H), 8.20 (br. s., 1H), 8.00 (s, 1H), 7.84-7.78 (m, 2H), 4.72-4.60 (m, 3H), 4.41-4.34 (m, 1H), 1.80 (quin, J=7.3 Hz, 2H), 0.99 (t, J=7.2 Hz, 3H). LC-MS: m/z 356.1 (M+H).

Example 23

1-(((4S,5R)-5-ethyl-2-oxooxazolidin-4-yl)methoxy)imidazo[1,2-a][1,7]naphthyridine-6-carboxamide

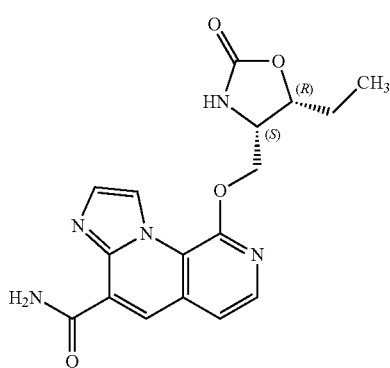

(23)

This compound was synthesized according to the general procedure outlined in Example 16 using the appropriate intermediates. ¹H NMR (400 MHz, DMSO-d₆) δ 9.75 (br. s., 1H), 8.89 (d, J=1.2 Hz, 1H), 8.45 (s, 1H), 8.23 (d, J=5.4 Hz, 1H), 8.19 (br. s., 1H), 8.01 (s, 1H), 7.82 (d, J=1.2 Hz, 1H), 7.76 (d, J=5.4 Hz, 1H), 5.61 (td, J=4.7, 7.2 Hz, 1H), 4.55-4.43 (m, 2H), 4.35 (td, J=4.2, 8.9 Hz, 1H), 1.88 (qt, J=7.2, 14.5 Hz, 2H), 0.94 (t, J=7.5 Hz, 3H). LC-MS: m/z 356.1 (M+H).

Example 24

1-(((4S,5S)-5-ethyl-2-oxooxazolidin-4-yl)methoxy)imidazo[1,2-a][1,7]naphthyridine-6-carboxamide

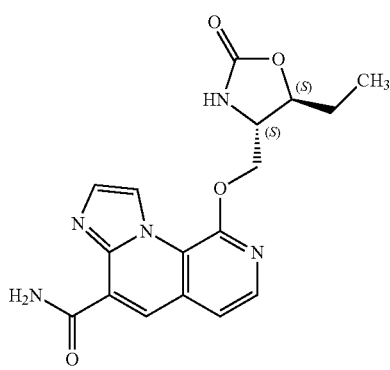

(24)

This compound was synthesized according to the general procedure outlined in Example 16 using the appropriate intermediates. ¹H NMR (400 MHz, DMSO-d₆) δ 9.73 (br. s., 1H), 8.89 (s, 1H), 8.43 (s, 1H), 8.23 (d, J=5.4 Hz, 1H), 8.17 (br. s., 1H), 8.00 (s, 1H), 7.80-7.74 (m, 2H), 4.71-4.59 (m, 3H), 4.41-4.32 (m, 1H), 1.80 (quin, J=7.4 Hz, 2H), 0.99 (t, J=7.3 Hz, 3H). LC-MS: m/z 356.1 (M+H).

Example 25

1-(((2R,3S)-2-ethyl-5-oxomorpholin-3-yl)methoxy)imidazo[1,2-a][1,7]naphthyridine-6-carboxamide

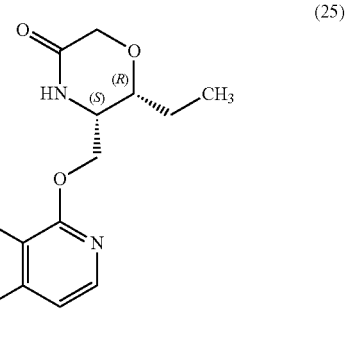

(25)

This compound was synthesized according to the general procedure outlined in Example 16 using the appropriate intermediates. ¹H NMR (400 MHz, DMSO-d₆) δ 9.75 (br. s., 1H), 9.13 (s, 1H), 8.46 (s, 1H), 8.40 (d, J=3.9 Hz, 1H), 8.24 (d, J=5.1 Hz, 1H), 8.19 (br. s., 1H), 7.82 (s, 1H), 7.77 (d, J=5.6 Hz, 1H), 4.88 (dd, J=11.4, 3.8 Hz, 1H), 4.60 (dd, J=11.1, 5.7 Hz, 1H), 4.26-4.00 (m, 2H), 3.91 (br. s., 1H), 3.83 (s, 1H), 1.80-1.52 (m, 2H), 0.99 (t, J=7.3 Hz, 3H). LC-MS: m/z 370.1 (M+H).

Example 26

1-(((2S,3R)-2-ethyl-5-oxomorpholin-3-yl)methoxy)imidazo[1,2-a][1,7]naphthyridine-6-carboxamide

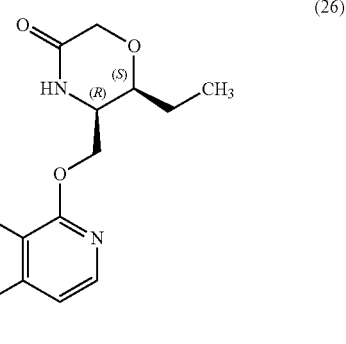

(26)

This compound was synthesized according to the general procedure outlined in Example 16 using the appropriate intermediates. ¹H NMR (400 MHz, DMSO-d₆) δ 9.75 (br. s., 1H), 9.00 (d, J=1.2 Hz, 1H), 8.46 (s, 1H), 8.37 (br. s., 1H), 8.22 (d, J=5.4 Hz, 1H), 8.19 (br. s., 1H), 7.82 (d, J=1.2 Hz, 1H), 7.75 (d, J=5.4 Hz, 1H), 5.72-5.60 (m, 1H), 3.99 (s, 2H), 3.97-3.93 (m, 2H), 3.90-3.82 (m, 1H), 2.03-1.89 (m, 2H), 0.95 (t, J=7.3 Hz, 3H). LC-MS: m/z 370.1 (M+H).

Example 27

(S)-1-((2-oxoimidazolidin-4-yl)methoxy)imidazo[1,2-a][1,7]naphthyridine-6-carboxamide

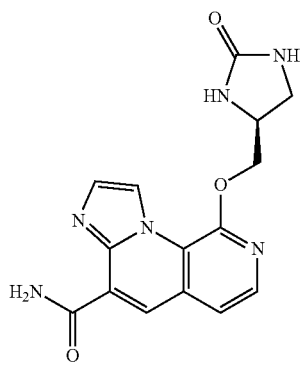
(27)

This compound was synthesized according to the general procedure outlined in Example 16 using the appropriate intermediates. $^1$H NMR (400 MHz, DMSO-$d_6$) δ 9.75 (br. s., 1H), 8.96 (s, 1H), 8.46 (s, 1H), 8.29-8.13 (m, 2H), 7.78 (br. s., 2H), 6.70 (s, 1H), 6.35 (s, 1H), 4.65-4.44 (m, 2H), 4.31-4.20 (m, 1H), 3.64-3.58 (m, 1H), 3.17 (d, J=4.2 Hz, 1H). LC-MS: m/z 327.4 (M+H).

Example 28

1-(((2S,3R)-3-ethyl-5-oxopyrrolidin-2-yl)methoxy)-3-methylimidazo[1,2-a][1,7]naphthyridine-6-carboxamide

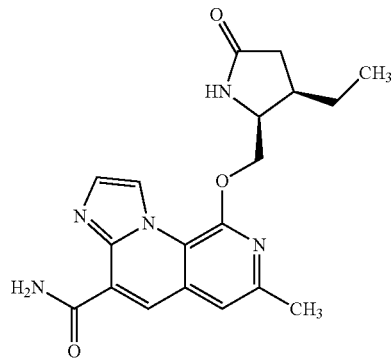
(28)

Intermediate 28A: ethyl 6-methyl-3-nitro-2-oxo-1,2-dihydropyridine-4-carboxylate

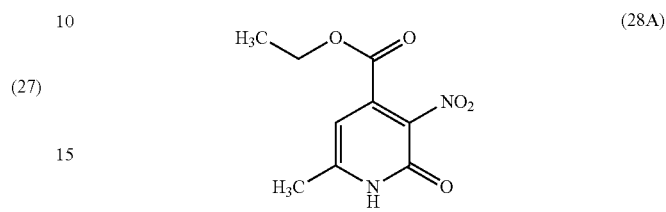
(28A)

To a solution of ethyl 2,4-dioxopentanoate (5 g, 31.6 mmol) in water were added acetic acid (5.43 mL, 95 mmol), 2-nitroacetamide (4.28 g, 41.1 mmol) and piperidine (6.26 mL, 63.2 mmol) at room temperature. The reaction mixture was stirred at the room temperature for 4 h. The solvent was evaporated under reduced pressure and the residue was diluted with water. The pH of aqueous solution was adjusted to ~4 and extracted with ethyl acetate. The combined organic extracts were dried over anhydrous $Na_2SO_4$ and concentrated to provide ethyl 6-methyl-3-nitro-2-oxo-1,2-dihydropyridine-4-carboxylate (2.5 g, 35% yield). $^1$H NMR (400 MHz, DMSO-$d_6$) δ 13.16 (br. s., 1H), 6.41 (s, 1H), 4.29 (q, J=7.0 Hz, 2H), 2.32 (s, 3H), 1.29-1.19 (m, 3H). LC-MS: m/z 227.1 (M+H).

Intermediate 28B: ethyl 3-amino-6-methyl-2-oxo-1,2-dihydropyridine-4-carboxylate

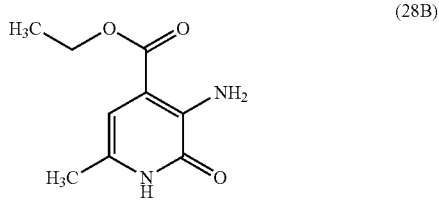
(28B)

To a stirred solution of ethyl 6-methyl-3-nitro-2-oxo-1,2-dihydropyridine-4-carboxylate (1.2 g, 5.3 mmol) in methanol (50 mL) was added Pd/C (0.57 g, 5.3 mmol) at room temperature. The reaction mixture was hydrogenated under balloon pressure of hydrogen at room temperature for 16 h. The reaction mixture was filtered through celite and washed with methanol. The filtrate was concentrated under reduced pressure to provide ethyl 3-amino-6-methyl-2-oxo-1,2-dihydropyridine-4-carboxylate (1 g, 96% yield) as an off-white solid. $^1$H NMR (400 MHz, DMSO-$d_6$) δ 13.16 (br. s., 1H), 6.41 (s, 1H), 4.29 (q, J=7.0 Hz, 2H), 2.32 (s, 3H), 1.29-1.19 (m, 3H). LC-MS: m/z 197 (M+H).

Intermediate 28C: ethyl 3-amino-2-chloro-6-methylisonicotinate

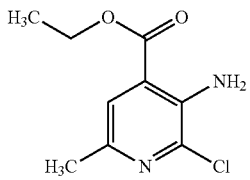

(28C)

To a solution of ethyl 3-amino-6-methyl-2-oxo-1,2-dihydropyridine-4-carboxylate (1.7 g, 8.66 mmol) and POCl$_3$ (0.808 mL, 8.66 mmol) was added 2 drops of DMF. The reaction mixture was heated at reflux for 16 h. The reaction mixture was cooled to room temperature and the solvent was removed under reduced pressure. The gummy mass was dissolved in NaHCO$_3$ solution and extracted with ethyl acetate. The combined organic extracts were dried over anhydrous Na$_2$SO$_4$ and concentrated under reduced pressure. The crude compound was purified by column chromatography (silica gel, 20% ethyl acetate in pet-ether) to provide ethyl 3-amino-2-chloro-6-methylisonicotinate (1 g, 54% yield). LC-MS: m/z 215.4 (M+H).

Intermediate 28D: (3-amino-2-chloro-6-methylpyridin-4-yl)methanol

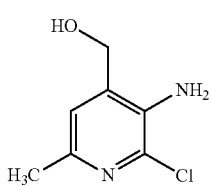

(28D)

To a stirred solution of ethyl 3-amino-2-chloro-6-methylisonicotinate (3 g, 13.98 mmol) in tetrahydrofuran (40 mL) was added LAH (5.82 mL, 14 mmol) slowly over a period of 5 min at −78° C. The reaction mixture was allowed to warm to room temperature and stirred for 1 h. The reaction mixture was cooled to 0° C. and quenched with ethyl acetate followed by aqueous Na$_2$SO$_4$ solution and then extracted with ethyl acetate. The combined organic extracts were washed with water, dried over anhydrous Na$_2$SO$_4$ and evaporated under reduced pressure to provide (3-amino-2-chloro-6-methylpyridin-4-yl)methanol (2.2 g, 91% yield). LC-MS: m/z 173.1 (M+H).

Intermediate 28E: 3-amino-2-chloro-6-methylisonicotinaldehyde

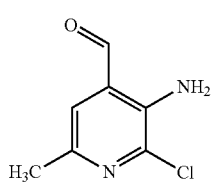

(28E)

To a stirred solution of (3-amino-2-chloro-6-methylpyridin-4-yl)methanol (2.1 g, 12.2 mmol) in DCM (20 mL) was added manganese dioxide (3.17 g, 37 mmol) and stirred at room temperature for 16 h. The reaction mixture was diluted with DCM and filtered through celite and washed with DCM. The filtrate was concentrated and the crude compound was purified by column chromatography (silica gel, 25% ethyl acetate in pet ether) to provide 3-amino-2-chloro-6-methylisonicotinaldehyde (1.2 g, 58% yield) as color less liquid. $^1$H NMR (300 MHz, DMSO-d$_6$) δ 9.95 (s, 1H), 7.47 (s, 1H), 6.90 (br. s., 2H), 2.36 (s, 3H). LC-MS: m/z 171.1 (M+H).

Intermediate 28F: 2-amino-8-chloro-6-methyl-1,7-naphthyridine-3-carboxamide

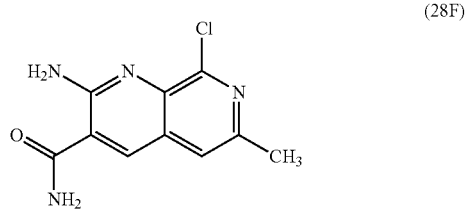 [SMILES: Cc1cc2cc(C(N)=O)c(N)nc2c(Cl)n1]

(28F)

To a stirred solution of 3-amino-2-chloro-6-methylisonicotinaldehyde (0.3 g, 1.8 mmol) in ethanol (20 mL) was added 2-cyanoacetamide (0.163 g, 1.9 mmol) followed by piperidine (0.017 mL, 0.18 mmol) at room temperature. The reaction was heated at 100° C. for 16 h and cooled to room temperature. The solvent was concentrated under reduced pressure and the residue was dissolved in water and extracted with ethyl acetate. The combined organic extracts were dried over anhydrous Na$_2$SO$_4$ and concentrated. The crude compound was purified by column chromatography (silica gel, 3% methanol in chloroform) to provide 2-amino-8-chloro-6-methyl-1,7-naphthyridine-3-carboxamide (0.4 g, 96% yield) as an off-white solid. LC-MS: m/z 237.1 (M+H).

Intermediate 28G: 1-chloro-3-methylimidazo[1,2-a][1,7]naphthyridine-6-carboxamide

(28G)

To a stirred solution of 2-amino-8-chloro-6-methyl-1,7-naphthyridine-3-carboxamide (0.1 g, 0.42 mmol) in DMF (5 mL) was added 2-chloroacetaldehyde (0.083 g, 0.63 mmol) at room temperature. The reaction mixture was heated at 95° C. for 4 h and cooled to room temperature. The solvent was concentrated under reduced pressure and the residue was dissolved in water and extracted with ethyl acetate. The combined organic extracts were dried over anhydrous Na$_2$SO$_4$ and concentrated. The crude compound was purified by column chromatography (Silica gel, 2% methanol in chloroform) to provide 1-chloro-3-methylimidazo[1,2-a][1,7]naphthyridine-6-carboxamide (0.07 g, 64% yield). LC-MS: m/z 261.1 (M+H).

Intermediate 28H: 1-chloro-3,8-dimethylimidazo[1,2-a][1,7]naphthyridine-6-carboxamide

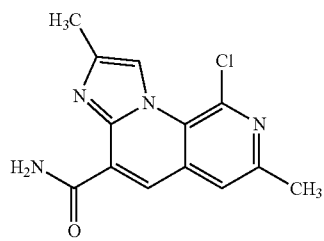

(28H)

To a stirred solution of 2-amino-8-chloro-6-methyl-1,7-naphthyridine-3-carboxamide (0.15 g, 0.63 mmol) in DMF (5 mL) was added 1-chloropropan-2-one (0.088 g, 0.95 mmol) at room temperature. The reaction mixture was heated at 95° C. for 4 h and cooled to room temperature. The solvent was concentrated under reduced pressure and the residue was dissolved in water and extracted with ethyl acetate. The combined organic extracts were dried over anhydrous $Na_2SO_4$ and concentrated. The crude compound was purified by column chromatography (silica gel, 2% methanol in chloroform) to provide 1-chloro-3,8-dimethyl-imidazo[1,2-a][1,7]naphthyridine-6-carboxamide (0.07 g, 40% yield). LC-MS: m/z 275.2 (M+H).

Example 28: 1-(((2S,3R)-3-ethyl-5-oxopyrrolidin-2-yl)methoxy)-3-methylimidazo[1,2-a][1,7]naphthyridine-6-carboxamide This compound was synthesized according to the general procedure outlined in Example 16 using the appropriate intermediates. $^1$H NMR (400 MHz, DMSO-$d_6$) δ 0.89-0.93 (m, 3H) 1.31-1.46 (m, 2H) 1.58-1.64 (m, 1H) 2.10 (s, 1H) 2.20-2.32 (m, 2H) 3.81 (s, 1H) 4.15 (d, J=5.38 Hz, 1H) 4.57-4.67 (m, 3H) 7.57 (s, 1H) 7.72-7.78 (m, 1H) 8.04-8.09 (m, 1H) 8.17 (br. s., 1H) 8.34 (s, 1H) 8.80-8.87 (m, 1H) 9.74 (br. s., 1H). LC-MS: m/z 368.2 (M+H).

Example 29

1-(((2S,3R)-3-ethyl-5-oxopyrrolidin-2-yl)methoxy)-3,8-dimethylimidazo[1,2-a][1,7]naphthyridine-6-carboxamide

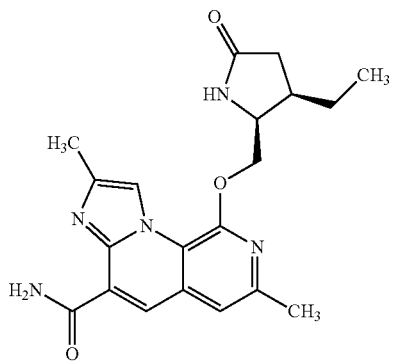

(29)

This compound was synthesized according to the general procedure outlined in Example 16 using the appropriate intermediates. $^1$H NMR (400 MHz, DMSO-$d_6$) δ 0.92 (d, J=6.85 Hz, 3H) 1.35 (br. s., 1H) 1.54-1.62 (m, 1H) 1.95 (dd, J=16.75, 6.97 Hz, 1H) 2.01-2.12 (m, 2H) 2.23-2.34 (m, 3H) 4.12 (br. s., 2H) 4.50-4.55 (m, 1H) 4.74 (dd, J=11.00, 5.87 Hz, 1H) 6.51 (s, 1H) 7.53 (s, 1H) 8.05-8.16 (m, 2H) 8.28 (s, 1H) 8.55 (s, 1H) 9.78 (br. s., 1H). LC-MS: m/z 382.1 (M+H).

Examples 30 and 31

1-(((2S,3R)-3-ethyl-5-oxopyrrolidin-2-yl)methoxy)-8-(trifluoromethyl)imidazo[1,2-a][1,7]naphthyridine-6-carboxamide (30) and 1-(((2S,3S)-3-ethyl-5-oxopyrrolidin-2-yl) methoxy)-8-(trifluoromethyl)imidazo[1,2-a][1,7]naphthyridine-6-carboxamide (31)

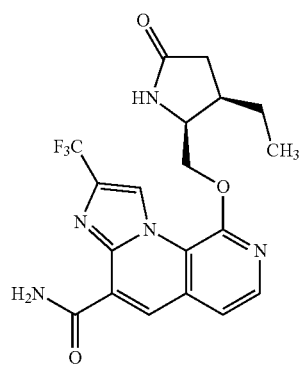

(30)

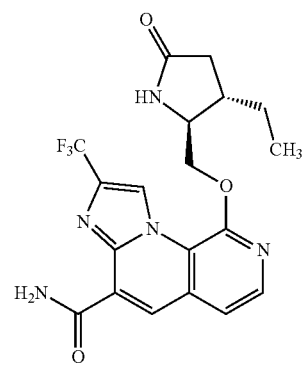

(31)

Intermediate 30A: 1-chloro-8-(trifluoromethyl)imidazo[1,2-a][1,7]naphthyridine-6-carboxamide

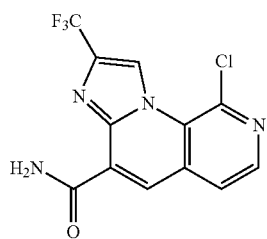

(30A)

To a stirred solution of 2-amino-8-chloro-1,7-naphthyridine-3-carboxamide (0.2 g, 0.9 mmol) in DMF (5 mL) was added 3-chloro-1,1,1-trifluoropropan-2-one (0.197 g, 1.35 mmol) and the reaction mixture was stirred at 95° C. for 4 h. The reaction mixture was cooled to room temperature and the solvent was removed under reduced pressure. The crude obtained was diluted with water and extracted with ethyl acetate. The combined organic layer was dried over anhydrous Na$_2$SO$_4$ and concentrated. The crude compound was purified by column chromatography (silica gel, 2% chloroform in methanol) to provide 1-chloro-8-(trifluoromethyl)imidazo[1,2-a][1,7]naphthyridine-6-carboxamide (0.07 g, 25% yield) as an off-white solid. LC-MS: m/z 315.2 (M+H).

Examples 30 and 31: 1-(((2S,3R)-3-ethyl-5-oxopyrrolidin-2-yl)methoxy)-8-(trifluoromethyl)imidazo[1,2-a][1,7]naphthyridine-6-carboxamide (30) and 1-(((2S,3S)-3-ethyl-5-oxopyrrolidin-2-yl)methoxy)-8-(trifluoromethyl)imidazo[1,2-a][1,7]naphthyridine-6-carboxamide (31)

These compounds were synthesized according to the general procedure outlined in Example 16 using the appropriate intermediates and the chloride above.

Example 30: $^1$H NMR (400 MHz, DMSO-d$_6$) δ 0.92 (d, J=6.85 Hz, 3H) 1.35 (br. s., 1H) 1.54-1.62 (m, 1H) 1.95 (dd, J=16.75, 6.97 Hz, 1H) 2.01-2.12 (m, 1H) 2.23-2.34 (m, 1H) 4.12 (br. s., 1H) 4.50-4.55 (m, 1H) 4.74 (dd, J=11.00, 5.87 Hz, 1H) 7.81-7.83 (d, 1H) 8.05-8.16 (m, 1H) 8.28 (d, 1H) 8.6 (s, 1H) 9.11 (s, 1H) 9.2 (br. s., 1H). LC-MS: m/z 422.1 (M+H).

Example 31: $^1$H NMR (400 MHz, DMSO-d$_6$) δ 0.91 (t, J=7.34 Hz, 3H) 1.40-1.50 (m, 1H) 1.60-1.67 (m, 1H) 1.96 (dd, J=16.75, 6.72 Hz, 1H) 2.22 (d, J=6.36 Hz, 1H) 2.33 (br. s., 1H) 3.17 (d, J=5.38 Hz, 1H) 3.80-3.84 (m, 1H) 4.01-4.11 (m, 1H) 4.59-4.71 (m, 2H) 7.84 (d, J=5.14 Hz, 1H) 8.07 (s, 1H) 8.25-8.35 (m, 2H) 8.62 (s, 1H) 9.11 (br. s., 1H) 9.24 (s, 1H). LC-MS: m/z 422 (M+H).

Example 32

(1-(((2S,3S,4S)-3-ethyl-4-fluoro-1-(hydroxymethyl)-5-oxopyrrolidin-2-yl)methoxy) imidazo[1,2-a][1,7]naphthyridine-6-carboxamide

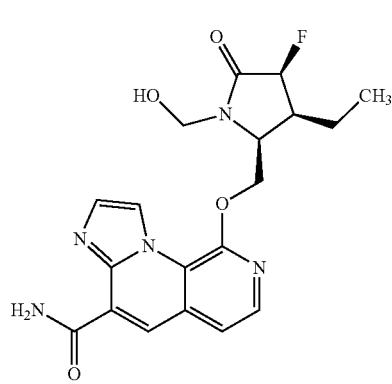

(32)

To a solution of 1-(((2S,3S,4S)-3-ethyl-4-fluoro-5-oxopyrrolidin-2-yl)methoxy) imidazo[1,2-a][1,7]naphthyridine-6-carboxamide (100 mg, 0.27 mmol) in DMF (6 mL) was added NaH (32.3 mg, 0.81 mmol) at 0° C. After stirring for 20 min, bromomethyl acetate (41.2 mg, 0.27 mmol) in 0.1 mL of DMF was added stirring continued for 20 min. The reaction was quenched by the addition of 4 drops of 1.5 N HCl. The reaction mixture was diluted with ethyl acetate. The reaction mixture was concentrated at 28-33° C. in vacuo and the crude compound was purified by prep-HPLC to provide ((2S,3S,4S)-2-(((6-carbamoylimidazo[1,2-a][1,7]naphthyridin-1-yl)oxy)methyl)-3-ethyl-4-fluoro-5-oxopyrrolidin-1-yl)methyl acetate (6 mg, 5% yield) as an off-white solid. $^1$H NMR (400 MHz, DMSO-d$_6$) δ 9.73 (br. s., 1H) 8.96 (d, J=1.47 Hz, 1H) 8.47 (s, 1H) 8.26 (d, J=5.14 Hz, 1H) 8.21 (br. s., 1H) 7.75-7.86 (m, 2H) 6.09 (t, J=7.09 Hz, 2H) 5.08 (d, J=5.62 Hz, 1H) 4.88-4.98 (m, 2H) 4.72-4.87 (m, 3H) 4.50 (dd, J=7.95, 3.06 Hz, 1H) 2.38-2.48 (m, 2H) 1.53-1.77 (m, 3H) 1.00 (t, J=7.34 Hz, 3H). LC-MS: m/z 402.4 (M+H).

Example 33

1-((((3R)-3-ethyl-5-oxopyrrolidin-2-yl)methyl)amino)imidazo[1,2-a][1,7]naphthyridine-6-carboxamide

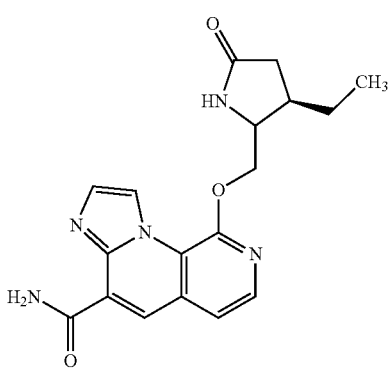

(33)

Intermediate 33A: ethyl 1-chloroimidazo[1,2-a][1,7]naphthyridine-6-carboxylate

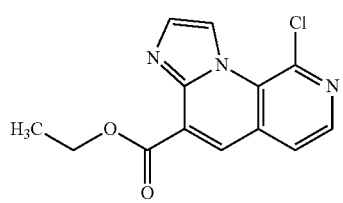

(33A)

To a stirred suspension of ethyl 2-amino-8-chloro-1,7-naphthyridine-3-carboxylate (200 mg, 0.80 mmol) in ethanol (5 mL) was added 2-chloroacetaldehyde (136 mg, 0.95 mmol) and heated to 80° C. for 16 h. Then, an additional amount of 2-chloroacetaldehyde (136 mg, 0.95 mmol) was added the above reaction mixture and continued heating for 2 h. The reaction mixture was cooled to room temperature and concentrated in vacuo to give crude compound which was passed through a small pad of silica gel using 30% of ethyl acetate in pet-ether to provide ethyl 1-chloroimidazo[1,2-a][1,7]naphthyridine-6-carboxylate (200 mg, crude) as yellow solid. LC-MS: m/z 276.7 (M+H).

Intermediate 33B: 1-chloro-N-methylimidazo[1,2-a][1,7]naphthyridine-6-carboxamide

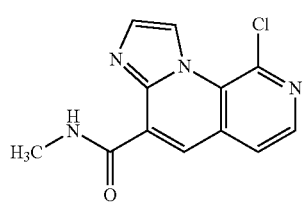

(33B)

To a solution of ethyl 1-chloroimidazo[1,2-a][1,7]naphthyridine-6-carboxylate (100 mg, 0.363 mmol) in methanol (1 mL) in a pressure tube was added methanamine (0.4 mL, 0.800 mmol, 2.0 in THF) and stirred at 25° C. for 2 h. The reaction mixture was concentrated under reduced pressure to give the desire compound 1-chloro-N-methylimidazo[1,2-a][1,7]naphthyridine-6-carboxamide (90 mg, 57% yield) as yellow solid. LC-MS: m/z 262.5 (M+H).

Example 33: 1-((((2S,3R)-3-ethyl-5-oxopyrrolidin-2-yl)methyl)amino)imidazo[1,2-a][1,7]naphthyridine-6-carboxamide To a stirred solution of (4R,5S)-5-(aminomethyl)-4-ethylpyrrolidin-2-one (34.6 mg, 0.24 mmol) and 1-chloroimidazo[1,2-a][1,7]naphthyridine-6-carboxamide (60 mg, 0.24 mmol) in DMSO (2 mL) was added potassium fluoride (14.13 mg, 0.24 mmol) and heated to at 110° C. for 16 h. The reaction mixture was cooled to room temperature and purified by preparative HPLC to provide 1-((((2S,3R)-3-ethyl-5-oxopyrrolidin-2-yl)methyl)amino)imidazo[1,2-a][1,7]naphthyridine-6-carboxamide (5.2 mg, 6% yield). LC-MS: m/z 353.4 (M+H).

Example 34

10-(((2S,3S,4S)-3-ethyl-4-fluoro-5-oxopyrrolidin-2-yl)methoxy)pyrazolo[5,1-a]isoquinoline-5-carboxamide

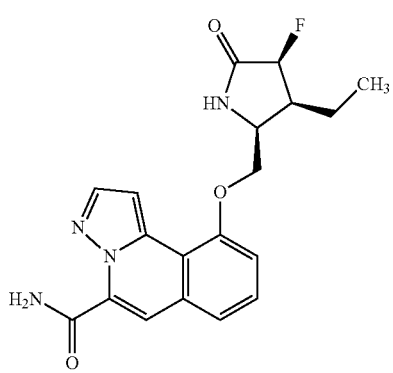

(34)

Intermediate 34A: 2-bromo-6-methoxybenzaldehyde

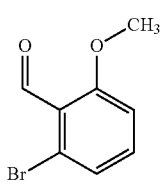

(34A)

To a solution of 2-bromo-6-hydroxybenzaldehyde (1.75 g, 8.7 mmol) in acetone (20 mL) was added $K_2CO_3$ (1.44 g, 10.5 mmol) followed by methyl iodide (1.09 mL, 17.4 mmol) at room temperature. The reaction mixture was stirred at the same temperature for 12 h. The reaction mixture was concentrated under reduced pressure and the residue was purified by column chromatography (silica gel, 20% ethyl acetate in pet-ether) to afford 2-bromo-6-methoxybenzaldehyde (1.8 g, 96% yield) as oily liquid. $^1$H NMR (400 MHz, Chloroform-d) δ 10.42 (s, 1H), 7.35-7.30 (m, 1H), 7.27-7.23 (m, 1H), 6.95 (dd, J=8.4, 0.9 Hz, 1H), 3.92 (s, 3H). LC-MS: m/z 217.1 (M+H).

Intermediate 34B: Preparation of 2-methoxy-6-(3-methoxyprop-1-yn-1-yl)benzaldehyde

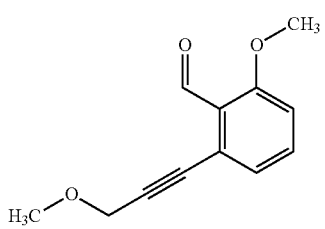

(34B)

To a stirred solution of 2-bromo-6-methoxybenzaldehyde (1.0 g, 4.7 mmol) in DMF (8 mL) was added 3-methoxyprop-1-yne (0.39 g, 5.6 mmol) followed by triethylamine (0.97 mL, 7.0 mmol) and copper(I) iodide (0.066 g, 0.35 mmol) at room temperature in a pressure tube. The mixture was degassed with argon for 5 min. To this was added bis(triphenylphosphine)palladium(II) dichloride (0.131 g, 0.19 mmol) and the solution was purged with argon for additional 5 min. The pressure tube was closed and heated to 70° C. for 6 h. The reaction mixture was cooled to room temperature and diluted with water and extracted with ethyl acetate. The combined organic extracts were washed with brine, dried over anhydrous $Na_2SO_4$ and evaporated under reduced pressure. The crude compound was purified by column chromatography (silica gel, 25% ethyl acetate in pet ether) to provide 2-methoxy-6-(3-methoxyprop-1-yn-1-yl)benzaldehyde (0.4 g, 42% yield) as oily liquid. LC-MS: m/z 205.1 (M+H).

Intermediate 34C: 10-methoxy-5-(methoxymethyl) pyrazolo[5,1-a]isoquinoline

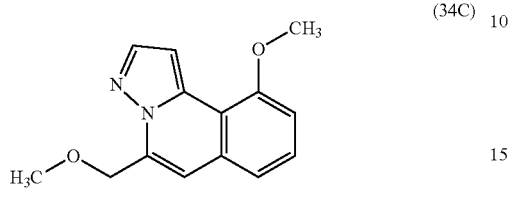
(34C)

To a stirred solution of 2-methoxy-6-(3-methoxyprop-1-yn-1-yl)benzaldehyde (0.4 g, 1.96 mmol) in DCE was added 4-methylbenzenesulfonohydrazide (0.438 g, 2.35 mmol) at room temperature. The mixture was stirred at the same temperature for 10 min. Silver trifluoromethanesulfonate (0.050 g, 0.20 mmol) was added and the reaction mixture was stirred at 60° C. with an open condenser for 30 min. The reaction mixture was cooled to 0° C. and was added $CuCl_2$ (0.019 g, 0.196 mmol) followed by N-ethyl-N-isopropyl-propan-2-amine (2.81 mL, 20 mmol). The reaction mixture was stirred for 12 h at room temperature, diluted with water and extracted with dichloromethane. The combined organic extracts were dried over anhydrous sodium sulphate and concentrated. The crude compound was purified by (Silica gel, 20% ethyl acetate in pet ether) to provide 10-methoxy-5-(methoxymethyl)pyrazolo[5,1-a]isoquinoline as an off-white solid. $^1$H NMR (400 MHz, Chloroform-d) δ 8.02 (d, J=2.3 Hz, 1H), 7.52-7.47 (m, 1H), 7.37-7.34 (m, 2H), 7.12 (t, J=1.1 Hz, 1H), 7.06-7.01 (m, 1H), 5.02 (d, J=1.3 Hz, 2H), 4.10 (s, 3H), 3.63 (s, 3H). LC-MS: m/z 243.1 (M+H).

Intermediate 34D: (10-methoxypyrazolo[5,1-a]isoquinolin-5-yl)methanol

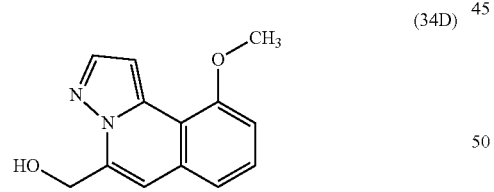
(34D)

To a stirred solution of 10-methoxy-5-(methoxymethyl) pyrazolo[5,1-a]isoquinoline (1.0 g, 4.13 mmol) in DCM (10 mL) was added $BBr_3$ (4.13 mL, 4.13 mmol) at −78° C. and stirred for 1 h. The reaction mixture was allowed to warm to room temperature and diluted with sodium bicarbonate solution and extracted with dichloromethane. The combined organic extracts were dried over anhydrous sodium sulphate and concentrated to provide (10-methoxypyrazolo[5,1-a]isoquinolin-5-yl)methanol (0.22 g, 23% yield) as a pale yellow solid. $^1$H NMR (400 MHz, DMSO-$d_6$) δ 8.07 (d, J=2.0 Hz, 1H), 7.61-7.55 (m, 1H), 7.52-7.48 (m, 1H), 7.32 (d, J=2.2 Hz, 1H), 7.26-7.19 (m, 2H), 5.73 (t, J=5.9 Hz, 1H), 4.97 (dd, J=5.7, 1.3 Hz, 2H), 4.08 (s, 3H). LC-MS: m/z 229.1 (M+H).

Intermediate 34E: 10-methoxypyrazolo[5,1-a]isoquinoline-5-carbaldehyde (34E)

To a solution of (10-methoxypyrazolo[5,1-a]isoquinolin-5-yl)methanol (0.3 g, 1.31 mmol) in toluene (5 mL) was added manganese dioxide (0.34 g, 3.94 mmol) and hated at 80° C. for 16 h. The reaction mixture was cooled to room temperature and diluted with sodium bicarbonate solution and extracted with dichloromethane. The combined organic extracts were dried over anhydrous sodium sulphate and concentrated. The crude compound was purified by (silica gel using 60% ethyl acetate in pet ether) to provide 10-methoxypyrazolo[5,1-a]isoquinoline-5-carbaldehyde (0.2 g, 67% yield) as a pale yellow solid. $^1$H NMR (400 MHz, Chloroform-d) δ 10.93 (s, 1H), 8.09 (d, J=2.3 Hz, 1H), 7.70 (s, 1H), 7.55 (t, J=7.9 Hz, 1H), 7.48 (dd, J=8.0, 1.0 Hz, 1H), 7.40 (d, J=2.0 Hz, 1H), 7.18 (dd, J=8.0, 1.0 Hz, 1H), 4.11 (s, 3H). LC-MS: m/z 227.1 (M+H).

Intermediate 34F: 10-methoxypyrazolo[5,1-a]isoquinoline-5-carbonitrile

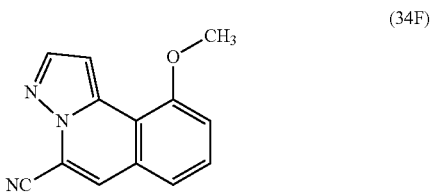 [SMILES: COc1cccc2cc(C#N)n3nccc3c12]
(34F)

To a solution of 10-methoxypyrazolo[5,1-a]isoquinoline-5-carbaldehyde (200 mg, 0.88 mmol) in tetrahydrofuran (10 mL) was added iodine (247 mg, 0.97 mmol) in 28% aqueous ammonia solution (6 mL). The mixture was stirred for 60 min then added $H_2O_2$ (0.027 mL, 0.88 mmol) and stirred for another 10 min. The reaction mixture was then diluted with sodium bicarbonate solution and extracted with dichloromethane. The combined organic extracts was dried over anhydrous sodium sulphate and concentrated. The crude compound was purified by column chromatography (silica gel, using 60% ethyl acetate in pet ether) to provide 10-methoxypyrazolo[5,1-a]isoquinoline-5-carbonitrile (0.125 g, 61% yield) as an off-white solid. $^1$H NMR (400 MHz, Chloroform-d) δ 8.11 (d, J=2.0 Hz, 1H), 7.61-7.55 (m, 2H), 7.40-7.37 (m, 2H), 7.20 (d, J=8.3 Hz, 1H), 4.12 (s, 3H). LC-MS: m/z 224.1 (M+H).

Intermediate 34G: 10-hydroxypyrazolo[5,1-a]isoquinoline-5-carbonitrile

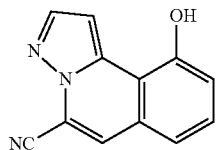
(34G)

To a stirred solution of 10-methoxypyrazolo[5,1-a]isoquinoline-5-carbonitrile (0.125 g, 0.56 mmol) in DCM (5 mL) was added BBr$_3$ (1.12 mL, 1.12 mmol) at −78° C.

The reaction mixture was allowed to warm to room temperature and stirred for 12 h. The reaction mixture was diluted with sodium bicarbonate and extracted with dichloromethane. The combined organic extracts were dried over anhydrous sodium sulphate and concentrated. The crude material was purified by column chromatography (silica gel, using 60% ethyl acetate in pet ether) to provide 10-hydroxypyrazolo[5,1-a]isoquinoline-5-carbonitrile (0.11 g, 94% yield) as a pale yellow solid. $^1$H NMR (400 MHz, DMSO-d$_6$) δ 11.04 (s, 1H), 8.18-8.14 (m, 2H), 7.58-7.52 (m, 1H), 7.44 (d, J=7.0 Hz, 1H), 7.37 (d, J=2.0 Hz, 1H), 7.29-7.25 (m, 1H). LC-MS: m/z 210.1 (M+H).

Intermediate 34H: 10-(((2S,3S,4S)-3-ethyl-4-fluoro-5-oxopyrrolidin-2-yl)methoxy) pyrazolo[5,1-a]isoquinoline-5-carbonitrile

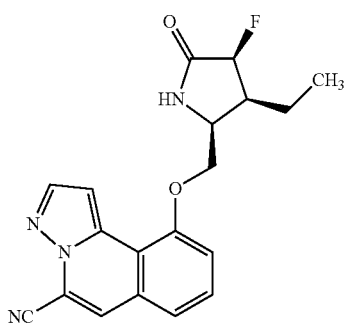
(34H)

To a solution of 10-hydroxypyrazolo[5,1-a]isoquinoline-5-carbonitrile (0.05 g, 0.24 mmol) and ((2S,3S,4S)-3-ethyl-4-fluoro-5-oxopyrrolidin-2-yl)methyl 4-methylbenzenesulfonate (0.075 g, 0.24 mmol) in DMF (5 mL) was added Cs$_2$CO$_3$ (0.234 g, 0.72 mmol). The reaction mixture was heated at 60° C. for 2 h. The reaction mixture was cooled to room temperature and diluted with water and extracted with ethyl acetate. The combined organic extracts were washed with brine, dried over Na$_2$SO$_4$ and concentrated to afford 10-(((2S,3S,4S)-3-ethyl-4-fluoro-5-oxopyrrolidin-2-yl)methoxy) pyrazolo[5,1-a]isoquinoline-5-carbonitrile (0.1 g, 0.19 mmol, 80% yield) as a pale yellow solid. The crude compound was used in the next step without further purification. LC-MS: m/z 353.1 (M+H).

Example 34: 10-(((2S,3S,4S)-3-ethyl-4-fluoro-5-oxopyrrolidin-2-yl)methoxy) pyrazolo[5,1-a]isoquinoline-5-carboxamide A solution of ethyl 10-(((2S,3S,4S)-3-ethyl-4-fluoro-5-oxopyrrolidin-2-yl) methoxy)pyrazolo[5,1-a]isoquinoline-5-carbonitrile (0.1 g, 0.28 mmol) in concentrated H$_2$SO$_4$ (1.0 mL, 18.8 mmol) was heated at 55° C. for 60 min. The reaction mixture was cooled room temperature, diluted with aqueous ammonia solution and extracted with ethyl acetate. The combined organic extracts were washed with brine, dried over Na$_2$SO$_4$ and concentrated. The crude compound was purified by preparative HPLC to provide 10-(((2S,3S,4S)-3-ethyl-4-fluoro-5-oxopyrrolidin-2-yl)methoxy)pyrazolo[5,1-a]isoquinoline-5-carboxamide (5 mg g, 4% yield) a pale yellow solid. $^1$H NMR (400 MHz, DMSO-d$_6$) δ 9.75 (br. s., 1H), 8.84 (s, 1H), 8.33 (br. s., 1H), 8.20 (d, J=2.2 Hz, 1H), 8.05 (s, 1H), 7.70 (d, J=7.6 Hz, 1H), 7.63 (t, J=7.9 Hz, 1H), 7.52 (d, J=2.2 Hz, 1H), 7.43 (d, J=8.3 Hz, 1H), 4.99 (d, J=5.6 Hz, 1H), 4.39-4.30 (m, 1H), 4.25 (br. s., 1H), 4.21-4.13 (m, 1H), 2.76-2.59 (m, 1H), 1.74-1.50 (m, 2H), 1.04-0.90 (m, 3H). LC-MS: m/z 371.1 (M+H).

Example 35

10-(((2S,3R)-3-ethyl-5-oxopyrrolidin-2-yl)methoxy) pyrazolo[5,1-a]isoquinoline-5-carboxamide

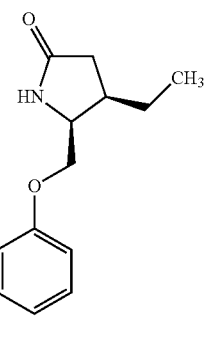
(35)

These compounds were synthesized according to the general procedure outlined in Example 34 using the appropriate intermediates. $^1$H NMR (400 MHz, DMSO-d$_6$) δ 0.87 (t, J=7.34 Hz, 3H) 1.22-1.39 (m, 1H) 1.61-1.69 (m, 1H) 1.91-2.01 (m, 1H) 2.06-2.18 (m, 1H) 2.20-2.30 (m, 1H) 4.08-4.22 (m, 1H) 4.23-4.38 (m, 2H) 7.47 (d, J=2.45 Hz, 2H) 7.68 (d, J=15.41 Hz, 2H) 8.07 (s, 2H) 8.20 (d, J=2.20 Hz, 1H) 8.31-8.40 (m, 1H) 9.71-9.77 (m, 1H). LC-MS: m/z 353.1 (M+H).

Example 36

1-(((2S,3S,4S)-3-ethyl-4-fluoro-5-oxopyrrolidin-2-yl)methoxy)pyrazolo[5,1-a][2,7]naphthyridine-6-carboxamide

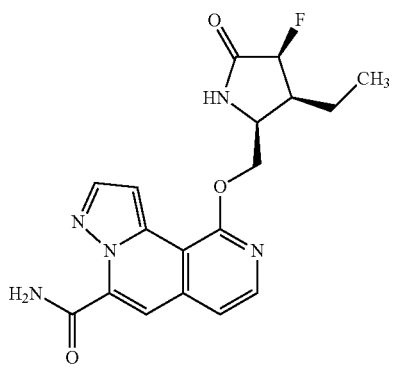

(36)

Intermediate 36A: 2-chloro-4-(3-methoxyprop-1-yn-1-yl)nicotinaldehyde

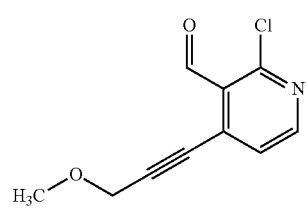

(36A)

To a solution of 2-chloro-4-iodonicotinaldehyde (3.5 g, 13.1 mmol) in THF (70 mL) in a pressure tube were added Et$_3$N (9.12 mL, 65.4 mmol) followed by copper(I) iodide (30 mg, 0.16 mmol). The reaction mixture was degassed with argon for 5 min. Bis(triphenylphosphine)palladium(II) dichloride (100 mg, 0.14 mmol) and 3-methoxyprop-1-yne (0.917 g, 13.1 mmol) were added to the reaction mixture. The pressure tube was closed and the reaction mixture was stirred at 25° C. for 12 h. The reaction mixture was diluted with water and extracted with ethyl acetate. The combined organic extracts were dried over anhydrous Na$_2$SO$_4$ and concentrated. The crude mixture was purified by column chromatography (silica gel, 15% ethyl acetate in pet-ether) to provided 2-chloro-4-(3-methoxyprop-1-yn-1-yl)nicotinaldehyde (1 g, 36% yield) as an off-white solid. $^1$H NMR (400 MHz, DMSO-d$_6$) δ 10.37 (s, 1H), 8.60 (d, J=4.80 Hz, 1H), 7.66 (d, J=4.80 Hz, 1H), 4.45 (s, 2H), 3.39 (s, 3H). LC-MS: m/z 210.4 (M+H).

Intermediate 36B: 1-chloro-6-(methoxymethyl)pyrazolo[5,1-a][2,7]naphthyridine

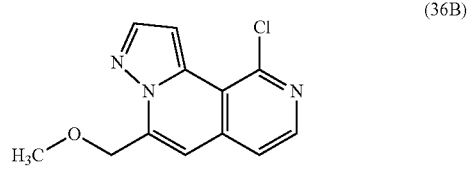 [SMILES: COCc1cc2ccnc(Cl)c2c2ccnn12]

(36B)

To a solution of 2-chloro-4-(3-methoxyprop-1-yn-1-yl)nicotinaldehyde (1.0 g, 4.77 mmol) in ethanol (15 mL) were added 4-methylbenzenesulphonhydrazide (0.89 g, 4.77 mmol) followed by silver trifluoromethanesulfonate (0.184 g, 0.72 mmol). The reaction mixture was stirred for 40 min with an open condenser. DL-proline (0.082 g, 0.72 mmol) was added and the reaction mixture was stirred for 15 min. Acetaldehyde (2.10 g, 48 mmol) was added and the reaction mixture was heated under microwave at 60° C. for 40 min. The reaction mixture was cooled to room temperature and treated with Na$_2$CO$_3$ (3.03 g, 28.6 mmol). The formed suspension was stirred for 6 h at room temperature then filtered and concentrated to a dark red syrup. The crude compound was purified by column chromatography (silica gel, 20% ethyl acetate in pet-ether) to provide 1-chloro-6-(methoxymethyl)pyrazolo[5,1-a][2,7]naphthyridine (200 mg, 17% yield) as an off-white solid. $^1$H NMR (400 MHz, DMSO-d$_6$) δ 8.50 (d, J=5.5 Hz, 1H), 8.28 (d, J=2.5 Hz, 1H), 7.97 (d, J=5.5 Hz, 1H), 7.73 (d, J=2.5 Hz, 1H), 7.39 (s, 1H), 4.99 (d, J=1.0 Hz, 2H), 3.56 (s, 3H). LC-MS: m/z 248.4 (M+H).

Intermediate 36C: (1-chloropyrazolo[5,1-a][2,7]naphthyridin-6-yl)methanol

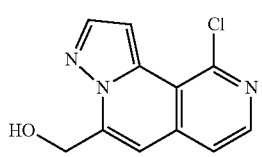

(36C)

To a stirred solution of 1-chloro-6-(methoxymethyl)pyrazolo[5,1-a][2,7]naphthyridine (150 mg, 0.61 mmol) in DCM (2 mL) was added boron tribromide (0.91 mL, 0.91 mmol, 1.0 M in DCM) at 0° C. The reaction mixture was allowed to warm to room temperature and stirred for 2 h. The reaction mixture was then cooled to 0° C. The reaction was quenched by the addition of 10% NaHCO$_3$ aqueous solution. The organic layer was separated and the aqueous layer was extracted with DCM. The combined organic extracts were dried over anhydrous Na$_2$SO$_4$ and concentrated to give the crude product which was triturated with pentane. The solid product was dried in vacuo to provide (1-chloropyrazolo[5,1-a][2,7]naphthyridin-6-yl)methanol (120 mg, 85% yield). $^1$H NMR (400 MHz, DMSO-d$_6$) δ 8.50 (d, J=5.1 Hz, 1H), 8.28 (d, J=2.2 Hz, 1H), 7.99 (d, J=5.4 Hz, 1H), 7.73 (d, J=2.2 Hz, 1H), 7.43 (s, 1H), 5.95 (br. s., 1H), 5.03 (s, 2H). LC-MS: m/z 234.2 (M+H).

Intermediate 36D: 1-chloropyrazolo[5,1-a][2,7]naphthyridine-6-carbaldehyde

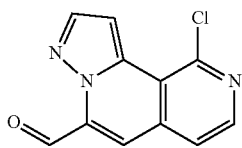

To a stirred suspension of (1-chloropyrazolo[5,1-a][2,7]naphthyridin-6-yl)methanol (120 mg, 0.51 mmol) in toluene (5 mL) was added manganese dioxide (134 mg, 1.54 mmol). The reaction mixture was heated to 100° C. for 4 h. The reaction mixture was cooled to room temperature, filtered, washed with toluene, and the filtrate was concentrated under reduced pressure to provide 1-chloropyrazolo[5,1-a][2,7]naphthyridine-6-carbaldehyde (80 mg, 67% yield) which was used further without purification. $^1$H NMR (400 MHz, DMSO-$d_6$) δ 10.80 (s, 1H), 8.61-8.59 (m, 1H), 8.41 (d, J=2.0 Hz, 1H), 8.15 (d, J=5.5 Hz, 1H), 7.95 (s, 1H), 7.81 (d, J=2.5 Hz, 1H). LC-MS: m/z 232.2 (M+H).

Intermediate 36E: 1-chloropyrazolo[5,1-a][2,7]naphthyridine-6-carboxamide

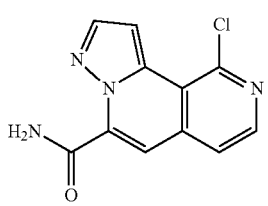

To a stirred solution of 1-chloropyrazolo[5,1-a][2,7]naphthyridine-6-carbaldehyde (80 mg, 0.345 mmol) in THF (2 mL) was added a mixture of iodine (175 mg, 0.691 mmol) and ammonia (5 mL, 231 mmol) at 25° C. After being stirred for 2 h, hydrogen peroxide (10.6 μL, 0.345 mmol) was added and stirred for 15 min. The reaction mixture was diluted with water and extracted with ethyl acetate. The combined organic extracts were concentrated under reduced pressure to provide 1-chloropyrazolo[5,1-a][2,7]naphthyridine-6-carboxamide (80 mg, 94% yield) as a brown solid, which was used further without purification.

Example 36: 1-(((2S,3 S,4S)-3-ethyl-4-fluoro-5-oxopyrrolidin-2-yl)methoxy) pyrazolo[5,1-a][2,7]naphthyridine-6-carboxamide This compound was synthesized by according to the general procedure as outlined in Example 34 using appropriate intermediates. $^1$H NMR (400 MHz, DMSO-$d_6$) δ 9.56 (br. s., 1H), 8.85 (s, 1H), 8.44 (br. s., 1H), 8.36-8.19 (m, 2H), 7.98 (s, 1H), 7.65 (d, J=5.4 Hz, 1H), 7.49 (d, J=2.2 Hz, 1H), 4.95 (d, J=5.6 Hz, 1H), 4.82 (d, J=5.4 Hz, 1H), 4.65 (dd, J=11.1, 5.0 Hz, 1H), 4.52 (dd, J=10.8, 7.3 Hz, 1H), 4.24 (br. s., 1H), 2.62-2.55 (m, 1H), 1.70-1.56 (m, 2H), 0.99 (t, J=7.3 Hz, 3H). LC-MS: m/z 372.2 (M+H)

Example 37

9-(((2S,3R)-3-ethyl-5-oxopyrrolidin-2-yl)methoxy)-[1,2,4]triazolo[1,5-a]quinoline-4-carboxamide

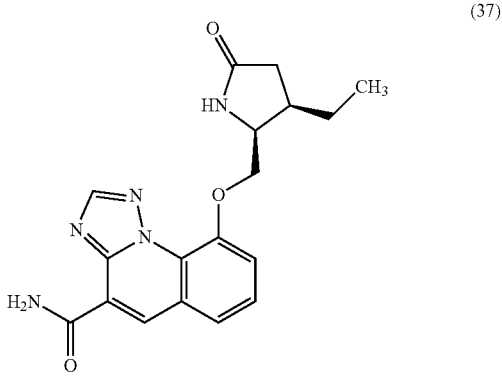

Intermediate 37A: ethyl 9-methoxy-[1,2,4]triazolo[1,5-a]quinoline-4-carboxylate

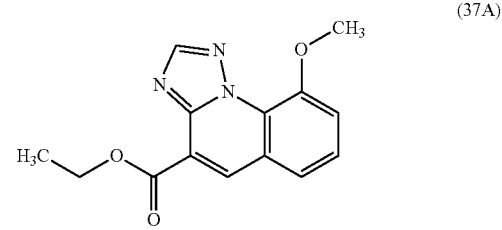 [SMILES: CCOC(=O)c1cc2cccc(OC)c2n2ncnc12]

To a solution of 1,2-diamino-3-(ethoxycarbonyl)-8-methoxyquinolin-1-ium (3.0 g, 5.72 mmol) in formic acid (5 mL, 130 mmol) was added HCl (0.95 mL, 5.72 mmol). The reaction mixture was heated at 90° C. for 16 h. The reaction mixture was cooled to room temperature and concentrated under reduced pressure. The residue was diluted with 10 mL of ethanol. Thionyl chloride (0.5 mL) was added and the reaction mixture was heated to 80° C. for 6 h. The reaction mixture was cooled to room temperature and the solvent was evaporated under reduced pressure. The crude compound was purified by column chromatography (silica gel, using 8% methanol in chloroform) to provide ethyl 9-methoxy-[1,2,4]triazolo[1,5-a]quinoline-4-carboxylate (0.5 g, 32% yield) as a light brown solid. $^1$H NMR (300 MHz, DMSO-$d_6$) δ 8.74 (s, 1H), 8.64 (s, 1H), 7.90 (d, J=5.3 Hz, 1H), 7.66 (d, J=7.6 Hz, 2H), 4.49-4.39 (m, 2H), 4.06 (s, 3H), 1.39 (t, J=7.2 Hz, 3H). LC-MS: m/z 272.1 (M+H).

Intermediate 37B: 9-methoxy-[1,2,4]triazolo[1,5-a]quinoline-4-carboxamide

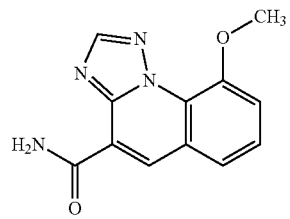

(37B)

To a freshly prepared ammonia solution in methanol (15 mL, 693 mmol) in a pressure tube was added ethyl 9-methoxy-[1,2,4]triazolo[1,5-a]quinoline-4-carboxylate (0.5 g, 1.84 mmol). The mixture was stirred at 25° C. for 12 h., then concentrated to provide 9-methoxy-[1,2,4]triazolo[1,5-a]quinoline-4-carboxamide (0.45 g, 100% yield) as an off-white solid. LC-MS: m/z 243.1 (M+H).

Intermediate 37C: 9-hydroxy-[1,2,4]triazolo[1,5-a]quinoline-4-carboxamide

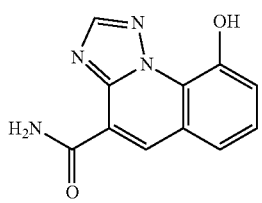

(37C)

To a stirred solution of 9-methoxy-[1,2,4]triazolo[1,5-a]quinoline-4-carboxamide (0.5 g, 2.06 mmol) in DCM (10 mL) was added BBr$_3$ (10.3 mL, 10.3 mmol) at −78° C. The reaction mixture was allowed to warm to room temperature and stirred for 16 h. The reaction mixture was cooled to 0° C., diluted with 10 mL of methanol and stirred for 10 min. The solvent was evaporated under reduced pressure to afford 9-hydroxy-[1,2,4]triazolo[1,5-a]quinoline-4-carboxamide (0.42 g, 1.840 mmol, 89% yield) as a pale yellow solid. $^1$H NMR (400 MHz, DMSO-d$_6$) δ 10.72 (br. s., 1H), 8.92-8.81 (m, 3H), 8.22 (br. s., 1H), 7.84 (d, J=7.0 Hz, 1H), 7.61 (t, J=8.0 Hz, 1H), 7.45 (d, J=8.0 Hz, 1H). LC-MS: m/z 229.1 (M+H).

Example 37: 9-(((2S,3R)-3-ethyl-5-oxopyrrolidin-2-yl)methoxy)-[1,2,4]triazolo[1,5-a]quinoline-4-carboxamide This compound was synthesized according to the general procedure outlined in Example 1 using appropriate intermediates. $^1$H NMR (400 MHz, DMSO-d$_6$) δ 0.92 (t, J=7.28 Hz, 3H) 1.24 (s, 1H) 1.50 (d, J=8.53 Hz, 1H) 1.68 (br. s., 1H) 2.21 (d, J=7.53 Hz, 1H) 4.04 (br. s., 1H) 4.19 (dd, J=10.04, 5.52 Hz, 1H) 4.37 (dd, J=9.54, 4.02 Hz, 1H) 7.56 (s, 1H) 7.63-7.70 (m, 2H) 7.94 (dd, J=5.77, 3.26 Hz, 1H) 8.18 (br. s., 1H) 8.70 (s, 1H) 8.80 (s, 1H) 9.08 (br. s., 1H). LC-MS: m/z 354.4 (M+H).

Example 38

9-(((2S,3S,4S)-3-ethyl-4-fluoro-5-oxopyrrolidin-2-yl)methoxy)-[1,2,4]triazolo[1,5-a]quinoline-4-carboxamide

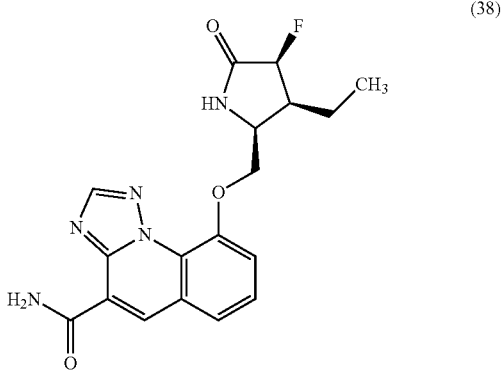

(38)

This compound was synthesized according to the general procedure outlined in Example 1 using appropriate intermediates. LC-MS: m/z 372.4 (M+H).

Example 39

9-(((2S,3S)-3-ethyl-4,4-difluoro-5-oxopyrrolidin-2-yl)methoxy)-[1,2,4]triazolo[1,5-a]quinoline-4-carboxamide

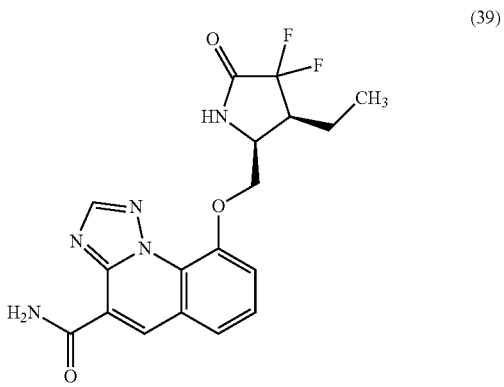

(39)

This compound was synthesized according to the general procedure outlined in Example 1 using appropriate intermediates. $^1$H NMR (400 MHz, DMSO-d$_6$) δ (t, J=7.28 Hz, 3H) 1.23 (br. s., 1H) 1.77 (d, J=6.53 Hz, 2H) 4.06 (d, J=9.04 Hz, 1H) 4.22-4.35 (m, 1H) 4.42 (dd, J=9.54, 4.52 Hz, 1H) 7.62-7.74 (m, 2H) 8.00 (dd, J=7.78, 1.25 Hz, 1H) 8.19 (br. s., 1H) 8.75 (s, 1H) 8.82 (s, 1H) 9.00-9.12 (m, 1H). LC-MS: m/z 390.4 (M+H).

Example 40

9-(((2S,3S,4S)-3-ethyl-4-fluoro-5-oxopyrrolidin-2-yl)methoxy)-2-methyl-[1,2,4]triazolo[1,5-a]quinoline-4-carboxamide

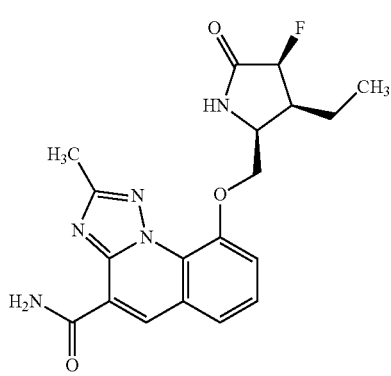

(40)

Intermediate 40A: 1,2-diamino-3-(ethoxycarbonyl)-8-methoxyquinolin-1-ium

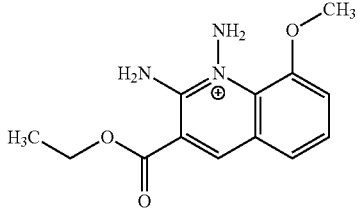

(40A)

To a stirred solution of ethyl o-methylsulfonylacetohydroxamate (1.74 g, 6.1 mmol) in 1,4-dioxane (1 mL) was added perchloric acid (0.31 mL, 3.1 mmol) at 0° C. The reaction mixture was stirred for 30 min. The reaction mixture was diluted with ice-cold water and stirred for an additional 5 min. The precipitated solid was filtered and immediately dissolved in DCM. The DCM layer was dried over $Na_2SO_4$ and filtered. This solution was cooled to 0° C. A solution of ethyl 2-amino-8-methoxyquinoline-3-carboxylate (0.5 g, 2.03 mmol) in DCM was added. The resulting reaction mixture was stirred at 0° C. for 4 h. The reaction mixture was diluted with ether and the supernatant layer was decanted. The residue semisolid was triturated with ether to provide partially pure 1,2-diamino-3-(ethoxycarbonyl)-8-methoxyquinolin-1-ium (0.5 g, 46.9% yield), which was used as such without further purification. $^1$H NMR (400 MHz, DMSO-$d_6$) δ 9.12 (s, 2H), 7.81 (d, J=9.0 Hz, 1H), 7.67 (d, J=9.0 Hz, 1H), 7.62-7.54 (m, 1H), 6.79 (br. s., 1H), 6.74 (s, 2H), 4.49-4.39 (m, 2H), 4.01 (s, 3H), 1.40 (t, J=7.0 Hz, 3H).

Intermediate 40B: ethyl 9-methoxy-2-methyl-[1,2,4]triazolo[1,5-a]quinoline-4-carboxylate

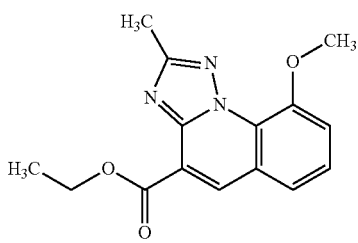

(40B)

To a solution of 1,2-diamino-3-(ethoxycarbonyl)-8-methoxyquinolin-1-ium (0.3 g, 0.57 mmol) in acetic anhydride (0.54 mL, 5.72 mmol) was added concentrated HCl (0.095 mL, 0.57 mmol) and the reaction mixture was heated at 90° C. for 16 h. The reaction mixture was cooled to room temperature, concentrated under reduced pressure and the residue was purified by column chromatography (Silica gel, 8% methanol in chloroform) to provide ethyl 9-methoxy-2-methyl-[1,2,4]triazolo[1,5-a]quinoline-4-carboxylate (0.15 g, 92% yield) as an off-white solid. LC-MS: m/z 286.3 (M+H).

Intermediate 40C: 9-methoxy-2-methyl-[1,2,4]triazolo[1,5-a]quinoline-4-carboxamide

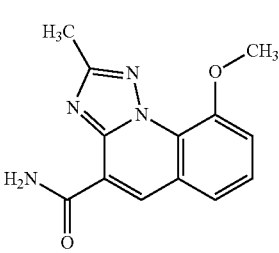

(40C)

A solution of ethyl 9-methoxy-2-methyl-[1,2,4]triazolo[1,5-a]quinoline-4-carboxylate (0.15 g, 0.526 mmol) in methanol in a pressure tube was purged with ammonia for 5 min. The reaction vessel was sealed. The reaction mixture was stirred at room temperature for 12 h. The solvent was evaporated under reduced pressure to afford 9-methoxy-2-methyl-[1,2,4]triazolo[1,5-a]quinoline-4-carboxamide (0.13 g, 93% yield) as an off-white solid. LC-MS: m/z 257.1 (M+H).

Intermediate 40D: 9-hydroxy-2-methyl-[1,2,4]triazolo[1,5-a]quinoline-4-carboxamide

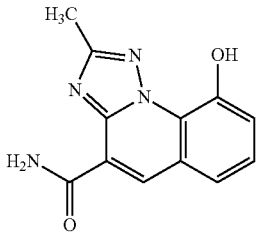
(40D)

To a stirred solution of 9-methoxy-2-methyl-[1,2,4]triazolo[1,5-a]quinoline-4-carboxamide (0.13 g, 0.507 mmol) in DCM (10 mL) was added BBr$_3$ (5.07 mL, 5.07 mmol) at −78° C. The reaction mixture was allowed to warm to room temperature and stirred for 16 h. The reaction mixture was then cooled to 0° C., diluted with 10 mL of methanol and stirred for 10 min. The solvent was evaporated under reduced pressure to afford 9-hydroxy-2-methyl-[1,2,4]triazolo[1,5-a]quinoline-4-carboxamide (0.1 g, 81% yield) as a pale yellow solid. $^1$H NMR (300 MHz, DMSO-d$_6$) δ 10.79 (br. s., 1H), 8.87 (br. s., 1H), 8.20 (br. s., 1H), 7.81 (d, J=8.3 Hz, 1H), 7.57 (t, J=7.9 Hz, 1H), 7.42 (d, J=7.9 Hz, 1H), 2.64 (s, 3H). LC-MS: m/z 243.2 (M+H).

Example 40: 9-(((2S,3S,4S)-3-ethyl-4-fluoro-5-oxopyrrolidin-2-yl)methoxy)-2-methyl-[1,2,4]triazolo[1,5-a]quinoline-4-carboxamide This compound was synthesized according to the general procedure outlined in Example 1 using appropriate intermediates. $^1$H NMR (400 MHz, DMSO-d$_6$) δ 1.02 (t, J=7.28 Hz, 3H) 1.55-1.73 (m, 2H) 2.34 (t, J=1.76 Hz, 1H) 2.58-2.70 (m, 3H) 3.97 (s, 1H) 4.16-4.28 (m, 1H) 4.54 (d, J=4.52 Hz, 1H) 4.87 (d, J=5.52 Hz, 1H) 6.80-7.02 (m, 1H) 7.58-7.75 (m, 1H) 7.97 (dd, J=8.03, 1.00 Hz, 1H) 8.18 (br. s., 1H) 8.57 (s, 1H) 8.78 (s, 1H) 9.08-9.17 (m, 1H). LC-MS: m/z 386.2 (M+H).

Examples 41 and 42

9-(((2S,3R)-3-ethyl-5-oxopyrrolidin-2-yl)methoxy)-[1,2,4]triazolo[4,3-a]quinoline-4-carboxamide and 9-(((2S,3S)-3-ethyl-5-oxopyrrolidin-2-yl)methoxy)-[1,2,4]triazolo [4,3-a]quinoline-4-carboxamide

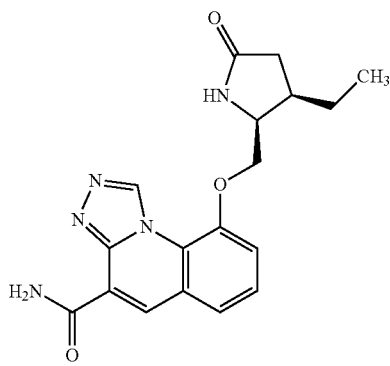
(41)

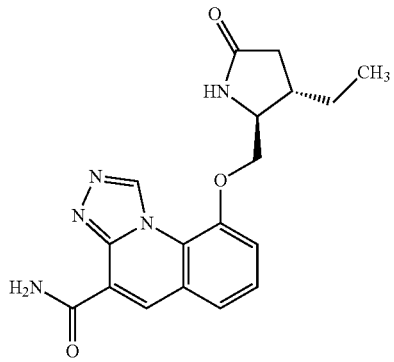
(42)

Intermediate 41A: diethyl 2-(3-methoxy-2-nitrobenzylidene)malonate

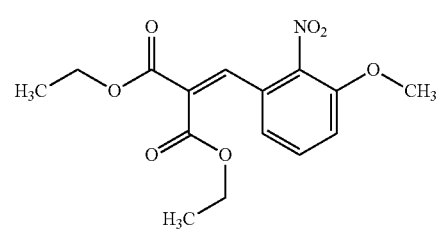
(41A)

To a stirred solution of 3-methoxy-2-nitrobenzaldehyde (4.5 g, 24.84 mmol) and diethyl malonate (3.98 g, 24.84 mmol) in acetic anhydride (15 mL, 159 mmol) was added K$_2$CO$_3$ (4.5 g, 32.6 mmol). The reaction mixture was heated at 80° C. for 4 h. The reaction mixture was poured into crushed ice and diluted with ethyl acetate. Solid NaHCO$_3$ was added carefully with stirring, until the CO$_2$ gas evolution subsided. The organic layer was separated, dried over anhydrous Na$_2$SO$_4$, and then concentrated to provide diethyl 2-(3-methoxy-2-nitrobenzylidene)malonate (6.99 g, 87% yield) as a pale brown syrup. LC-MS: m/z 324.1 (M+H).

Intermediate 41B: ethyl 8-methoxy-2-oxo-1,2-dihydroquinoline-3-carboxylate

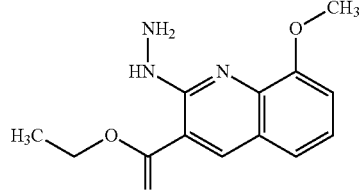
(41B)

To a stirred solution of diethyl 2-(3-methoxy-2-nitrobenzylidene)malonate (6.99 g, 21.62 mmol) in acetic acid (5 mL, 87 mmol) and ethanol (20 mL) was added iron (2.42 g, 43.2 mmol). The suspension was heated to 90° C. for 3 h., and then cooled to room temperature. The reaction mixture was diluted with DCM (100 mL). The reaction was quenched with water. The reaction mixture was stirred for 15 min. The organic layer was separated and the aqueous layer was extracted with DCM. The combined organic extracts were dried over anhydrous Na$_2$SO$_4$ and concentrated to provide ethyl 8-methoxy-2-oxo-1,2-dihydroquinoline-3-carboxylate (3.1 g, 12.54 mmol, 58.0% yield) as yellow solid. LC-MS: m/z 248.1 (M+H).

Intermediate 41D: ethyl 2-chloro-8-methoxyquinoline-3-carboxylate

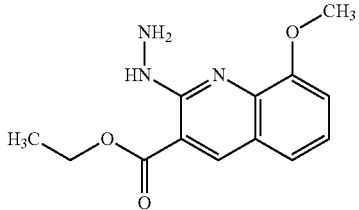

(41D)

To a stirred suspension of ethyl 8-methoxy-2-oxo-1,2-dihydroquinoline-3-carboxylate (2.2 g, 8.90 mmol) in toluene (30 mL) were added POCl$_3$ (2.5 mL, 26.7 mmol) followed by DIPEA (4.7 mL, 26.7 mmol). The reaction mixture was heated to 125° C. for 16 h. The reaction mixture was cooled to room temperature and concentrated in vacuo to a syrup that was diluted with ethyl acetate and poured into 10% NaHCO$_3$ solution. The mixture was filtered through celite and the filtrate was further diluted with ethyl acetate. The ethyl acetate layer was dried over Na$_2$SO$_4$ and concentrated to a pale brown solid. The crude compound was purified by column chromatography (silica gel, 15% ethyl acetate in pet-ether) to provide ethyl 2-chloro-8-methoxyquinoline-3-carboxylate (1.3 g, 55% yield) as a white crystalline solid. LC-MS: m/z 266.1 (M+H)

Intermediate 41F: ethyl 2-hydrazinyl-8-methoxyquinoline-3-carboxylate

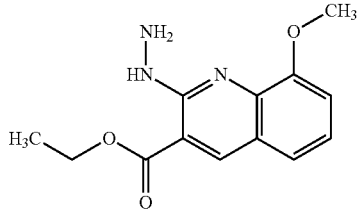

(41F)

To a stirred solution of ethyl 2-chloro-8-methoxyquinoline-3-carboxylate (350 mg, 1.32 mmol) in ethanol (40 mL) was added hydrazine hydrate (65.9 mg, 1.32 mmol). The reaction mixture was heated at 40° C. for 16 h. Additional hydrazine hydrate (65.9 mg, 1.32 mmol) was added. The reaction mixture was heated for an additional 24 h. The reaction mixture was concentrated in vacuo at 35° C. and the residue obtained was diluted with water and stirred for 10 min. The precipitated solids were filtered and dried to provide ethyl 2-hydrazinyl-8-methoxyquinoline-3-carboxylate (240 mg, 70% yield) as yellow solid. LC-MS: m/z 262.1 (M+H).

Intermediate 41G: ethyl 9-methoxy-[1,2,4]triazolo[4,3-a]quinoline-4-carboxylate

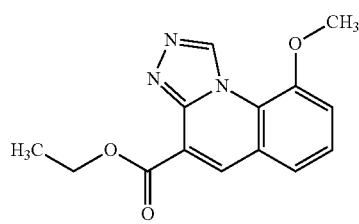

(41G)

A stirred solution of ethyl 2-hydrazinyl-8-methoxyquinoline-3-carboxylate (240 mg, 0.919 mmol) in formic acid (5 mL, 130 mmol) was heated to 95° C. for 16 h and cooled to room temperature. The reaction mixture was concentrated to give brown semi-solid which was neutralized using 10% NaHCO$_3$ solution and extracted with ethyl acetate. The combined organic extracts were dried over Na$_2$SO$_4$ and concentrated in vacuo to provide ethyl 9-methoxy-[1,2,4]triazolo[4,3-a]quinoline-4-carboxylate (180 mg, 72% yield) as a pale-brown solid. LC-MS: m/z 272.1 (M+H).

Intermediate 41H: 9-methoxy-[1,2,4]triazolo[4,3-a]quinoline-4-carboxamide

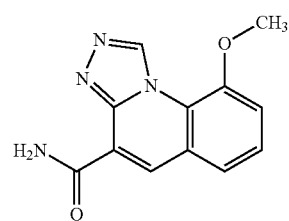

(41H)

To a solution of freshly prepared ammonia in methanol (15 mL, 693 mmol) in a pressure tube was added ethyl 9-methoxy-[1,2,4]triazolo[4,3-a]quinoline-4-carboxylate (180 mg, 0.66 mmol). The reaction mixture was stirred at 25° C. for 3 h. The reaction mixture was concentrated in vacuo to provide 9-methoxy-[1,2,4]triazolo[4,3-a]quinoline-4-carboxamide (150 mg, 93% yield) as an off-white solid. LC-MS: m/z 243.1 (M+H).

Intermediate 41I: 9-hydroxy-[1,2,4]triazolo[4,3-a]quinoline-4-carboxamide

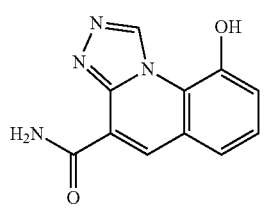

(41I)

To a stirred solution of 9-methoxy-[1,2,4]triazolo[4,3-a]quinoline-4-carboxamide (150 mg, 0.619 mmol) in DCM (5 mL) was added BBr₃ (6 mL, 6.00 mmol, 1.0 M in DCM) at −78° C. The reaction mixture was allowed to warm to room temperature over 1 h and stirring continued for 16 h. Additional 6 mL of (1.0 M) of BBr₃ was added at room temperature and continued stirring for additional 16 h. The reaction was quenched by methanol at −78° C. The mixture was concentrated to afford 9-hydroxy-[1,2,4]triazolo[4,3-a]quinoline-4-carboxamide (140 mg, 99% yield). LC-MS: m/z 229.1 (M+H).

Examples 41 and 42: 9-(((2S,3R)-3-ethyl-5-oxopyrrolidin-2-yl)methoxy)-[1,2,4]triazolo[4,3-a]quinoline-4-carboxamide and 9-(((2S,3S)-3-ethyl-5-oxopyrrolidin-2-yl)methoxy)-[1,2,4]triazolo[4,3-a]quinoline-4-carboxamide A racemic mixture of Examples 41 and 42 was synthesized according to the general procedure outlined in Example 1 using appropriate intermediates. Isomers were separated by preparative HPLC.

Example 41: ¹H NMR (400 MHz, DMSO-d₆) δ 9.93 (s, 1H), 9.13 (br. s., 1H), 8.55 (s, 1H), 8.30-8.14 (m, 2H), 7.86 (dd, J=7.8, 1.3 Hz, 1H), 7.76-7.54 (m, 2H), 4.40 (d, J=6.0 Hz, 2H), 4.22 (q, J=6.5 Hz, 1H), 2.38-2.21 (m, 2H), 2.10 (dd, J=16.6, 10.0 Hz, 1H), 1.72-1.56 (m, 1H), 1.50-1.30 (m, 1H), 0.90 (t, J=7.5 Hz, 3H). LC-MS: m/z 354.1 (M+H).

Example 42: ¹H NMR (400 MHz, DMSO-d₆) δ 9.91 (s, 1H), 9.12 (br. s., 1H), 8.56 (s, 1H), 8.19 (s, 2H), 7.96-7.79 (m, 1H), 7.73-7.46 (m, 2H), 4.52-4.24 (m, 2H), 4.00-3.75 (m, 1H), 2.35 (m, 1H), 2.29-2.10 (m, 1H), 1.97 (dd, J=16.8, 6.8 Hz, 1H), 1.65 (ddd, J=13.3, 7.5, 5.8 Hz, 1H), 1.57-1.26 (m, 1H), 1.06-0.81 (m, 3H). LC-MS: m/z 354.1 (M+H)

Example 43

9-(((2S,3S,4S)-3-ethyl-4-fluoro-5-oxopyrrolidin-2-yl)methoxy)-[1,2,4]triazolo[4,3-a]quinoline-4-carboxamide

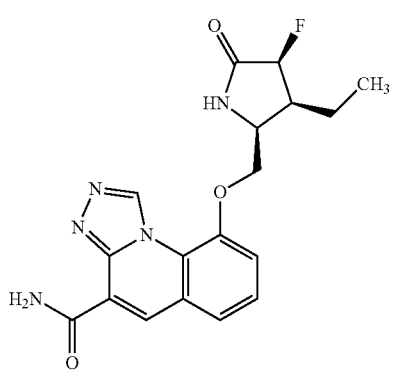

(43)

This compound was synthesized by according to the general procedure outlined in Example 1 using appropriate intermediates. ¹H NMR (400 MHz, DMSO-d₆) δ 9.97 (s, 1H), 9.04 (br. s., 1H), 8.55 (s, 1H), 8.30-8.14 (m, 2H), 7.85 (m, 1H), 7.68-7.62 (m, 2H), 4.90-4.80 (m, 1), 4.42-4.22 (m, 3H), 2.21 (m, 1H), 1.64-1.19 (m, 2H), 0.90 (t, J=7.2 Hz, 3H). LC-MS: m/z 372.5 (M+H).

Example 44

9-(((2S,3R)-3-ethyl-5-oxopyrrolidin-2-yl)methoxy)tetrazolo[1,5-a]quinoline-4-carboxamide

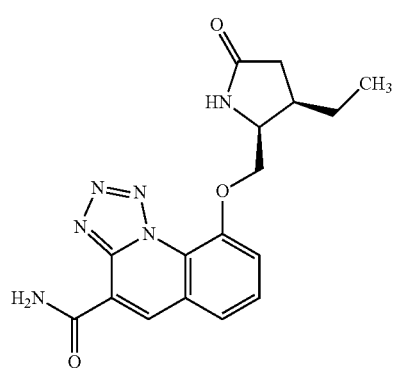

(44)

Intermediate 44A: ethyl 9-methoxytetrazolo[1,5-a]quinoline-4-carboxylate

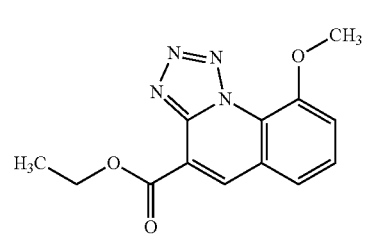

(44A)

To a solution of ethyl 2-chloro-8-methoxyquinoline-3-carboxylate (0.45 g, 1.7 mmol) in DMF (10 mL) was added sodium azide (0.132 g, 2.03 mmol). The reaction mixture was heated to 120° C. for 16 h. The reaction mixture was cooled to room temperature and concentrated to dryness. The residue was diluted with ethanol (10 mL) and thionyl chloride (0.5 mL) was added. The reaction mixture was heated at 80° C. for 6 h, cooled to room temperature, and concentrated. The crude compound was purified by column chromatography (silica gel, using 8% methanol in chloroform) to provide ethyl 9-methoxytetrazolo[1,5-a]quinoline-4-carboxylate (0.1 g, 22% yield) as an off-white solid. LC-MS: m/z 273.1 (M+H).

Intermediate 44B: Preparation of 9-methoxytetrazolo[1,5-a]quinoline-4-carboxamide

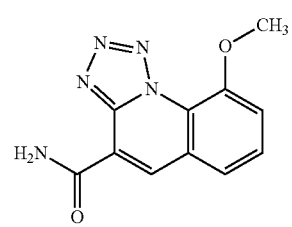

(44B)

To a freshly prepared ammonia solution (15 mL, 700 mmol) in methanol in a pressure tube was added ethyl 9-methoxytetrazolo[1,5-a]quinoline-4-carboxylate (0.1 g, 0.37 mmol). The reaction mixture was stirred at room temperature for 12 h. The reaction mixture was concentrated to provide 9-methoxytetrazolo[1,5-a]quinoline-4-carboxamide (0.06 g, 67% yield) as an off-white solid. ¹H NMR (400 MHz, DMSO-d₆) δ 8.89 (s, 1H), 8.53 (br. s., 1H), 8.33 (br. s., 1H), 8.00 (d, J=8.1 Hz, 1H), 7.82 (t, J=7.9 Hz, 1H), 7.75 (d, J=7.6 Hz, 1H), 4.15 (s, 3H). LC-MS: m/z 244.1 (M+H).

Intermediate 44C: 9-hydroxytetrazolo[1,5-a]quinoline-4-carboxamide

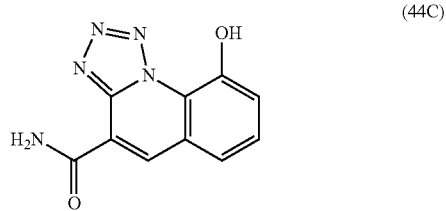 [SMILES: NC(=O)c1cc2cccc(O)c2n2nnnc12]
(44C)

To a stirred solution of 9-methoxytetrazolo[1,5-a]quinoline-4-carboxamide (0.06 g, 0.25 mmol) in DCM (10 mL) was added BBr₃ (1.23 mL, 1.23 mmol) at −78° C. The reaction mixture was allowed to come to room temperature and stirred for 16 h. The reaction mixture was cooled to 0° C., diluted with 6 mL of methanol, and stirred for 10 min. The solvent was evaporated under reduced pressure to provide 9-hydroxytetrazolo[1,5-a]quinoline-4-carboxamide (0.05 g, 88% yield) as a pale yellow solid. LC-MS: m/z 230.1 (M+H).

Example 44: 9-(((2S,3R)-3-ethyl-5-oxopyrrolidin-2-yl)methoxy)tetrazolo[1,5-a]quinoline-4-carboxamide This compound was synthesized according to the general procedure as outlined in Example 1 using appropriate intermediates. LC-MS: m/z 355.2 (M+H).

Example 45

9-(((2S,3S,4S)-3-ethyl-4-fluoro-5-oxopyrrolidin-2-yl)methoxy)tetrazolo[1,5-a]quinoline-4-carboxamide

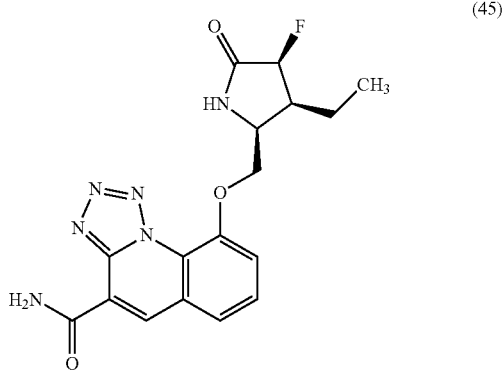 [SMILES: CC[C@@H]1[C@H](F)C(=O)N[C@@H]1COc1cccc2cc(C(N)=O)c3nnnn3c12]
(45)

This compound was synthesized according to the general procedure as outlined in Example 1 using appropriate intermediates. ¹H NMR (400 MHz, DMSO-d₆) δ 8.90 (s, 1H), 8.53 (br. s., 1H), 8.37 (s, 1H), 8.32 (br. s., 1H), 8.04 (dd, J=7.2, 1.8 Hz, 1H), 7.87-7.74 (m, 2H), 4.51 (dd, J=9.4, 5.5 Hz, 1H), 4.22 (br. s., 1H), 4.19-4.11 (m, 1H), 2.76-2.61 (m, 1H), 1.80-1.70 (m, 1H), 1.67-1.53 (m, 1H), 0.99 (t, J=7.3 Hz, 3H). LC-MS: m/z 373.2 (M+H)

Example 46

9-(((2S,3R)-3-ethyl-5-oxopyrrolidin-2-yl)methoxy)-[1,2,4]triazolo[1,5-a][1,7]naphthyridine-4-carboxamide

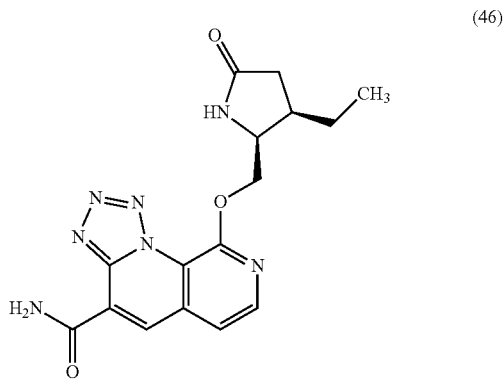 [SMILES: CC[C@@H]1CC(=O)N[C@@H]1COc1nccc2cc(C(N)=O)c3nnnn3c12]
(46)

Intermediate 46A: ethyl 2-amino-8-chloro-1,7-naphthyridine-3-carboxylate

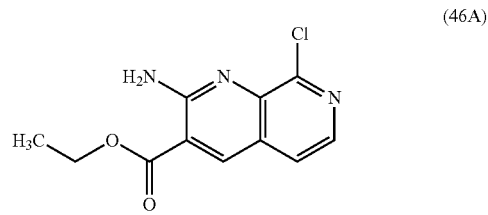 [SMILES: CCOC(=O)c1cc2ccnc(Cl)c2nc1N]
(46A)

To a stirred solution of 3-amino-2-chloroisonicotinaldehyde (1.7 g, 10.9 mmol) in ethanol (20 mL) was added ethyl cyanoacetate (1.45 g, 13.0 mmol) followed by piperidine (0.054 mL, 0.54 mmol) at room temperature. The reaction mixture was heated at 100° C. for 6 h, then cooled to room temperature and concentrated. The residue was dissolved in ethyl acetate, washed with water and brine, then dried over anhydrous sodium sulfate. The crude material was purified by column chromatography (silica gel, 3% methanol in chloroform) to provide ethyl 2-amino-8-chloro-1,7-naphthyridine-3-carboxylate (0.5 g, 18% yield) as a pale yellow solid. LC-MS: m/z 252.2 (M+H).

Intermediate 46B: (E)-ethyl 8-chloro-2-(((dimethylamino)methylene)amino)-1,7-naphthyridine-3-carboxylate

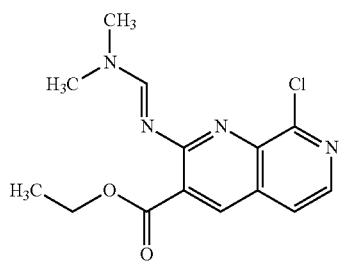

(46B)

To a stirred solution of ethyl 2-amino-8-chloro-1,7-naphthyridine-3-carboxylate (0.25 g, 0.99 mmol) in 2-propanol (20 mL) was added DMF-DMA (0.2 mL, 1.49 mmol) at room temperature. The resulting reaction mixture was heated at 100° C. for 4 h. The reaction mixture was cooled to room temperature and concentrated under reduced pressure to provide crude (E)-ethyl 8-chloro-2-(((dimethylamino)methylene)amino)-1,7-naphthyridine-3-carboxylate (0.15 g, 49% yield) as a pale yellow solid. The crude compound was taken to next step without further purification. LC-MS: m/z 308 (M+H).

Intermediate 46C: (E)-ethyl 8-chloro-2-(((hydroxyamino)methylene)amino)-1,7-naphthyridine-3-carboxylate

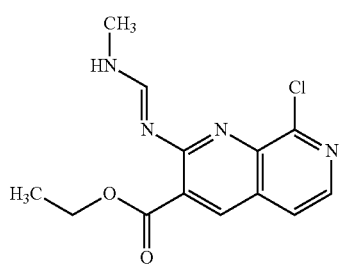

(46C)

To a stirred solution of (E)-ethyl 8-chloro-2-(((dimethylamino)methylene)amino)-1,7-naphthyridine-3-carboxylate (0.15 g, 0.49 mmol) in 2-propanol (10 mL) was added hydroxylamine hydrochloride (0.041 g, 0.59 mmol) at room temperature. The resulting reaction mixture was heated at 110° C. for 4 h. The reaction mixture was cooled to room temperature and concentrated to remove solvent. The residue was dissolved in water extracted with ethyl acetate. The combined organic layer was dried over anhydrous sodium sulphate and concentrated under reduced pressure. The crude compound was purified by column chromatography (silica gel, 50% ethyl acetate in pet-ether) to provide (E)-ethyl 8-chloro-2-(((hydroxyamino)methylene)amino)-1,7-naphthyridine-3-carboxylate obtained as a colorless liquid. LC-MS: m/z 295.2 (M+H).

Intermediate 46D: ethyl 9-chloro-[1,2,4]triazolo[1,5-a][1,7]naphthyridine-4-carboxylate

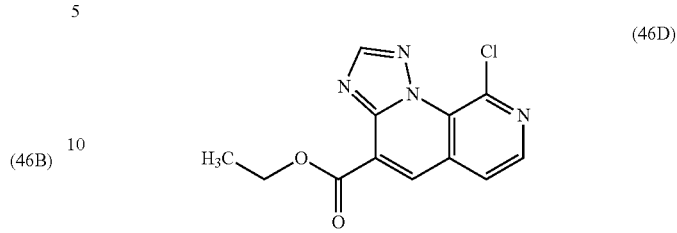

(46D)

To a stirred solution of (E)-ethyl 8-chloro-2-(((hydroxyamino)methylene)amino)-1,7-naphthyridine-3-carboxylate (0.1 g, 0.34 mmol) in THF (10 mL) was added TFAA (0.072 mL, 0.51 mmol) at room temperature. The reaction mixture was heated at 75° C. for 3 h. The reaction mixture was cooled to room temperature and concentrated under reduced pressure. The residue was dissolved in ethyl acetate, washed with aqueous NaHCO$_3$ solution, dried over anhydrous sodium sulphate and concentrated to provide ethyl 9-chloro-[1,2,4]triazolo[1,5-a][1,7]naphthyridine-4-carboxylate (0.05 g, 53% yield). LC-MS: m/z 277.2 (M+H).

Intermediate 46E: 9-chloro-[1,2,4]triazolo[1,5-a][1,7]naphthyridine-4-carboxylic acid

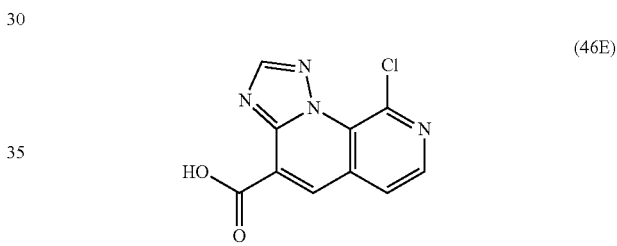

(46E)

To a solution of ethyl 9-chloro-[1,2,4]triazolo[1,5-a][1,7] naphthyridine-4-carboxylate (0.12 g, 0.43 mmol) in MeOH (5 mL) was added a solution of LiOH (10.4 mg, 0.43 mmol) in water at room temperature. The reaction mixture was stirred for 4 h. The solvent was evaporated under reduced pressure and the residue was dissolved in water and acidified the solution to pH ~4. The turbid aqueous solution was extracted with ethyl acetate and the organic layer was washed with water, dried over anhydrous sodium sulphate and concentrated under reduced pressure to provide 9-chloro-[1,2,4]triazolo[1,5-a][1,7]naphthyridine-4-carboxylic acid (0.06 g, 55% yield) as an off-white solid. LC-MS: m/z 249.1 (M+H).

Intermediate 46F: 9-chloro-[1,2,4]triazolo[1,5-a][1,7]naphthyridine-4-carboxamide

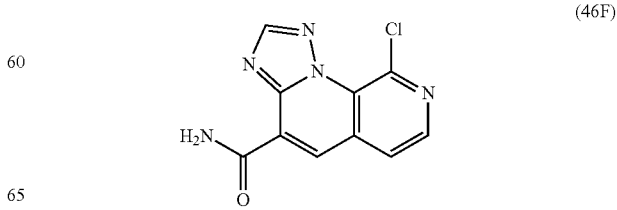

(46F)

To a stirred solution of 9-chloro-[1,2,4]triazolo[1,5-a][1,7]naphthyridine-4-carboxylic acid (0.05 g, 0.20 mmol) in DMF (2 mL) were added HATU (0.115 g, 0.30 mmol) followed by DIPEA (0.176 mL, 1.0 mmol) and ammonium chloride (0.054 g, 1.0 mmol) at room temperature. The reaction mixture was stirred for 3 h. The solvent was removed under reduced pressure and the residue was purified by column chromatography (silica gel, 5% methanol in chloroform) to provide 9-chloro-[1,2,4]triazolo[1,5-a][1,7]naphthyridine-4-carboxamide (0.03 g, 60% yield) as an off-white solid. LC-MS: m/z 248 (M+H).

Example 46: 9-(((2S,3R)-3-ethyl-5-oxopyrrolidin-2-yl)methoxy)-[1,2,4]triazolo[1,5-a][1,7]naphthyridine-4-carboxamide This compound was synthesized according to the general procedure as outlined in Example 16 using appropriate intermediates. $^1$H NMR (400 MHz, DMSO-d$_6$) δ 9.13-9.02 (m, 1H), 8.80-8.75 (m, 2H), 8.83-8.71 (m, 2H), 8.38-8.23 (m, 2H), 7.90-7.80 (m, 1H), 7.59-7.48 (m, 1H), 4.79-4.66 (m, 1H), 4.52-4.39 (m, 1H), 4.17-3.98 (m, 1H), 2.81-2.63 (m, 1H), 2.23-2.11 (m, 1H), 1.75-1.65 (m, 1H), 1.63-1.48 (m, 1H), 0.97-0.83 (m, 3H). LC-MS: m/z 355.0 (M+H).

Example 47

9-(((2S,3S,4S)-3-ethyl-4-fluoro-5-oxopyrrolidin-2-yl)methoxy)-[1,2,4]triazolo [1,5-a][1,7]naphthyridine-4-carboxamide

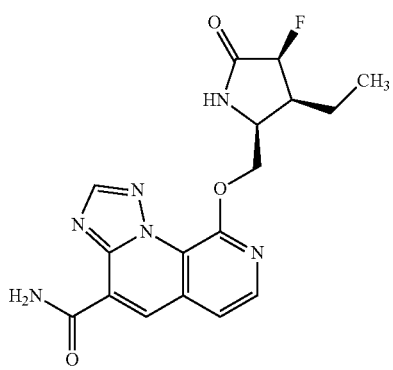

(47)

This compound was synthesized according to the general procedure as outlined in Example 16 using appropriate intermediates. $^1$H NMR (400 MHz, DMSO-d$_6$) δ 0.99 (s, 3H) 1.56-1.78 (m, 2H) 4.19 (br. s., 1H) 4.49 (m, 1H) 4.70 (dd, J=10.52, 6.11 Hz, 1H) 4.81 (s, 1H) 4.95 (d, J=5.38 Hz, 1H) 7.88 (d, J=5.62 Hz, 1H) 8.31-8.42 (m, 3H) 8.78 (s, 1H) 8.84 (s, 1H) 9.09 (br. s., 1H). LC-MS: m/z 373.1 (M+H).

Example 48

9-(((2S,3S)-3-ethyl-4,4-difluoro-5-oxopyrrolidin-2-yl)methoxy)-[1,2,4]triazolo[1,5-a][1,7]naphthyridine-4-carboxamide

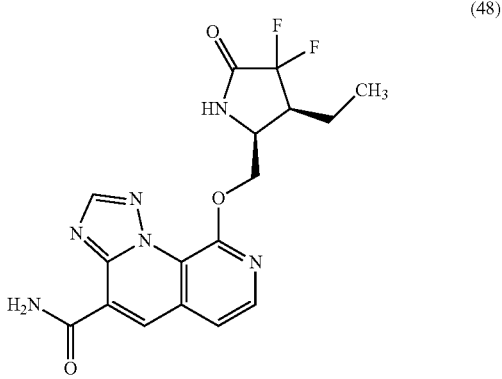 [SMILES: CC[C@H]1[C@@H](COc2nccc3cc(C(N)=O)c4ncnn4c23)NC(=O)C1(F)F]

(48)

This compound was synthesized by the general procedure as outlined in Example 16 using appropriate intermediates. $^1$H NMR (400 MHz, DMSO-d$_6$) δ 1.04 (t, J=7.46 Hz, 3H) 2.07 (s, 1H) 2.32-2.34 (m, 1H) 2.66-2.68 (m, 1H) 3.17 (d, J=5.38 Hz, 1H) 4.09 (d, J=5.14 Hz, 1H) 4.27 (br. s., 1H) 4.50-4.56 (m, 2H) 4.70 (dd, J=11.00, 5.62 Hz, 1H) 7.90 (d, J=5.38 Hz, 1H) 8.33 (d, J=5.38 Hz, 1H) 8.80 (s, 1H) 8.82 (s, 1H) 9.04 (br. s., 1H) 9.08 (br. s., 1H). LC-MS: m/z 391.1 (M+H).

Example 49

9-(((2S,3R)-3-ethyl-5-oxopyrrolidin-2-yl)methoxy)-2-methyl-[1,2,4]triazolo[1,5-a][1,7]naphthyridine-4-carboxamide

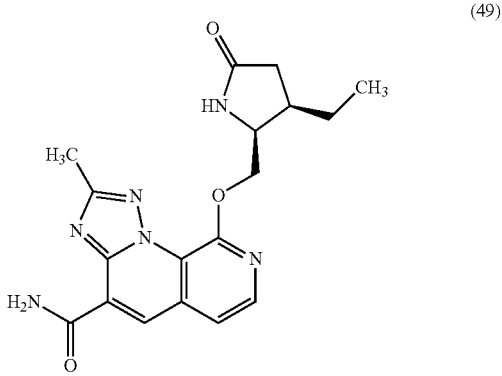

(49)

Intermediate 49A: ethyl (E)-8-chloro-2-((1-(dimethylamino)ethylidene)amino)-1,7-naphthyridine-3-carboxylate

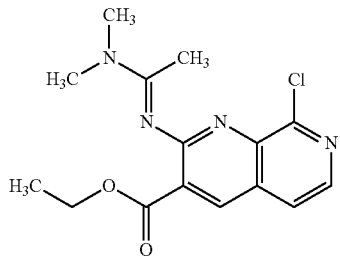

(49A)

To a stirred solution of ethyl 2-amino-8-chloro-1,7-naphthyridine-3-carboxylate (0.25 g, 0.99 mmol) in 2-propanol (20 mL) was added 1,1-dimethoxy-N,N-dimethylethanamine (0.132 g, 0.99 mmol) at room temperature. The reaction mixture was heated at 100° C. for 4 h. The reaction mixture was cooled to room temperature and concentrated to provide (E)-ethyl 8-chloro-2-((1-(dimethylamino)ethylidene)amino)-1,7-naphthyridine-3-carboxylate (0.15 g, 47% yield). This crude compound was taken to the next step without further purification. LC-MS: m/z 321.2 (M+H).

Intermediate 49B: ethyl (E)-8-chloro-2-((1-(hydroxyamino)ethylidene)amino)-1,7-naphthyridine-3-carboxylate

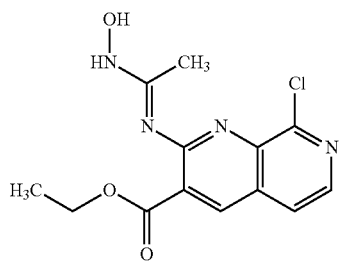

(49B)

To a stirred solution of (E)-ethyl 8-chloro-2-((1-(dimethylamino)ethylidene) amino)-1,7-naphthyridine-3-carboxylate (0.2 g, 0.62 mmol) in 2-propanol (10 mL) was added hydroxylamine hydrochloride (0.052 g, 0.75 mmol). The reaction mixture was heated at 110° C. for 4 h., then cooled to room temperature and concentrated to remove solvents. The residue was dissolved in water and extracted with ethyl acetate. The combined organic extracts were dried over sodium sulphate and concentrated. The crude compound was purified by column chromatography (silica gel, 50% ethyl acetate in pet ether) to provide (E)-ethyl 8-chloro-2-((1-(hydroxyamino)ethylidene)amino)-1,7-naphthyridine-3-carboxylate (0.15 g, 78% yield) as colorless liquid. LC-MS: m/z 309.2 (M+H).

Intermediate 49C: ethyl 9-chloro-2-methyl-[1,2,4]triazolo[1,5-a][1,7]naphthyridine-4-carboxylate

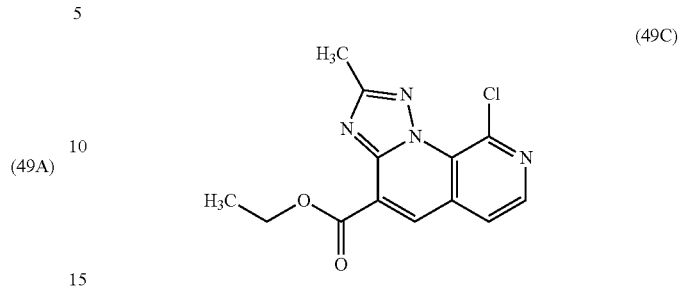

(49C)

To a stirred solution of (Z)-ethyl 8-chloro-2-((1-(hydroxyamino)ethylidene) amino)-1,7-naphthyridine-3-carboxylate (0.1 g, 0.324 mmol) in tetrahydrofuran (10 mL) was added TFAA (0.069 mL, 0.486 mmol). The reaction mixture was heated at 75° C. for 3 h. The reaction mixture was cooled to room temperature and concentrated. The crude compound was dissolved in ethyl acetate and washed with aqueous NaHCO$_3$ solution, dried over anhydrous sodium sulphate and concentrated to provide 9-chloro-2-methyl-[1,2,4]triazolo[1,5-a][1,7]naphthyridine-4-carboxylate (0.06 g, 64% yield). LC-MS: m/z 291.1 (M+H).

Intermediate 49D: 9-chloro-2-methyl-[1,2,4]triazolo[1,5-a][1,7]naphthyridine-4-carboxamide

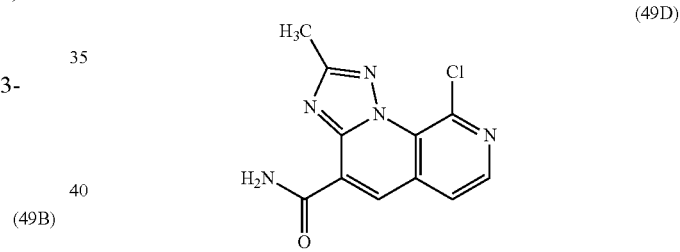

(49D)

A stirred solution of ethyl 9-chloro-2-methyl-[1,2,4]triazolo[1,5-a][1,7]naphthyridine-4-carboxylate (0.08 g, 0.28 mmol) in methanol (5 mL) was purged ammonia for 5 min at 0° C. The reaction vessel was sealed. The reaction mixture was stirred at room temperature for 12 h. The solvent was evaporated under reduced pressure to provide 9-chloro-2-methyl-[1,2,4]triazolo[1,5-a][1,7]naphthyridine-4-carboxamide. This crude compound was taken to the next step without further purification. LC-MS: m/z 262.2 (M+H).

Example 49: 9-(((2S,3R)-3-ethyl-5-oxopyrrolidin-2-yl)methoxy)-2-methyl-[1,2,4]triazolo[1,5-a][1,7]naphthyridine-4-carboxamide This compound was synthesized according to the general procedure as outlined in Example 16 using appropriate intermediates. $^1$H NMR (400 MHz, DMSO-d$_6$) δ 9.14-9.05 (m, 1H), 8.75-8.70 (m, 1H), 8.33-8.27 (m, 2H), 7.86-7.80 (m, 1H), 7.61-7.54 (m, 1H), 4.67-4.58 (m, 1H), 4.58-4.45 (m, 1H), 4.15-4.05 (m, 1H), 4.02-3.94 (m, 1H), 3.21-3.11 (m, 1H), 3.02-2.86 (m, 3H), 2.71-2.61 (m, 3H), 2.36-2.25 (m, 1H), 2.19-2.04 (m, 3H), 1.75-1.61 (m, 3H), 1.61-1.39 (m, 4H), 1.29-1.11 (m, 2H), 0.98-0.82 (m, 3H). LC-MS: m/z 369.1 (M+H).

Example 50

1-(((2S,3S,4S)-3-ethyl-4-fluoro-5-oxotetrahydrofuran-2-yl)methoxy)-8-methyl-8,9-dihydrofuro[2,3-h]isoquinoline-6-carboxamide

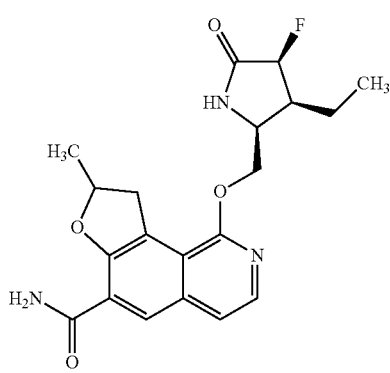

(50)

Intermediate 50A: methyl 7-(allyloxy)isoquinoline-6-carboxylate

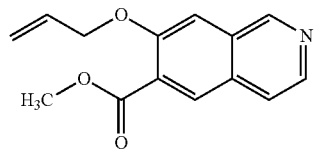

(50A)

To a stirred solution of methyl 7-hydroxyisoquinoline-6-carboxylate (0.5 g, 2.5 mmol) in acetone (10 mL) were added $K_2CO_3$ (1.02 g, 7.4 mmol) follow by allylbromide (0.43 mL, 4.9 mmol). The reaction mixture was stirred at room temperature for 3 h. The solvent was removed under reduced pressure and the residue was diluted with water and extracted with ethyl acetate. The combined organic extracts were dried over anhydrous $Na_2SO_4$ and concentrated to provide 7-(allyloxy)isoquinoline-6-carboxylate (0.3 g, 43% yield) as a light brown solid. LC-MS: m/z 244.2 (M+H).

Intermediate 50B: methyl 8-allyl-7-hydroxyisoquinoline-6-carboxylate

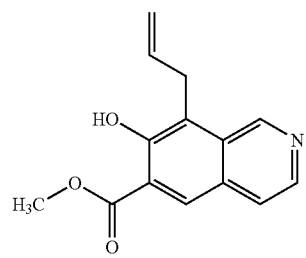

(50B)

To a stirred solution of methyl 7-(allyloxy)isoquinoline-6-carboxylate (0.2 g, 0.82 mmol) in xylene (10 mL) were added zinc chloride (0.112 g, 0.82 mmol) and 10 mg of silica gel. The reaction mixture was heated at 145° C. for 30 min. The reaction mixture was cooled to room temperature, filtered through celite, and washed with xylene. The filtrate was concentrated under reduced pressure. The crude compound was purified by column chromatography (silica gel, 45% ethyl acetate in pet ether) to provide methyl 8-allyl-7-hydroxyisoquinoline-6-carboxylate (0.18 g, 81% yield) as a light brown solid. LC-MS: m/z 244.2 (M+H).

Intermediate 50c: methyl 8-methyl-8,9-dihydrofuro[2,3-h]isoquinoline-6-carboxylate

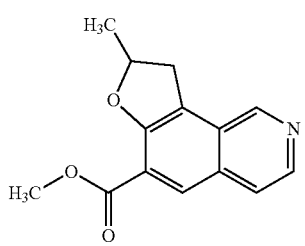

(50C)

To a solution of methyl 8-allyl-7-hydroxyisoquinoline-6-carboxylate (1.5 g, 6.17 mmol) in dichloroethane (50 mL) was added TFA (2.78 g, 18.5 mmol). The reaction mixture was heated at reflux for 1 h and cooled to room temperature. The solvent was removed under reduced pressure and the crude compound was purified by column chromatography (silica gel, 10% ethyl acetate in pet ether) to provide methyl 8-methyl-8,9-dihydrofuro[2,3-h]isoquinoline-6-carboxylate (0.4 g, 27% yield) as a light brown solid. LC-MS: m/z 244.2 (M+H).

Intermediate 50D: 6-(methoxycarbonyl)-8-methyl-8,9-dihydrofuro[2,3-h]isoquinoline 2-oxide

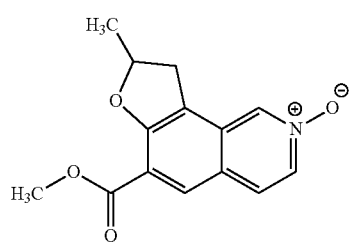

(50D)

To a stirred solution of methyl 8-methyl-8,9-dihydrofuro[2,3-h]isoquinoline-6-carboxylate (0.2 g, 0.82 mmol) in DCM (20 mL) was added m-CPBA (0.43 g, 2.47 mmol). The reaction mixture was stirred at room temperature for 3 h. The reaction mixture was diluted with DCM and washed with aqueous sodium bisulphate solution and water. The DCM extracts were dried over anhydrous $Na_2SO_4$ and concentrated to provide 6-(methoxycarbonyl)-8-methyl-8,9-dihydrofuro[2,3-h]isoquinoline 2-oxide (0.1 g, 47% yield) as an off-white solid. LC-MS: m/z 260.2 (M+H).

Intermediate 50E: Preparation of methyl 1-chloro-8-methyl-8,9-dihydrofuro[2,3-h]isoquinoline-6-carboxylate

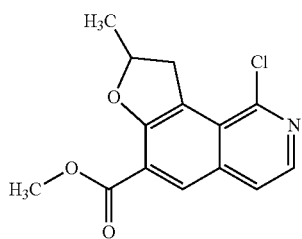

(50E)

To a solution of 6-(methoxycarbonyl)-8-methyl-8,9-dihydrofuro[2,3-h]isoquinoline 2-oxide (0.2 g, 0.77 mmol) in toluene (10 mL) were added $POCl_3$ (5 mL, 53.6 mmol) followed by 2 drops of DMF. The reaction mixture was heated at reflux for 16 h and cooled to room temperature. The solvent was removed under reduced pressure. The resulting gummy mass was dissolved in $NaHCO_3$ solution and extracted with ethyl acetate. The combined organic extracts were dried over anhydrous $Na_2SO_4$ and concentrated. The crude compound was purified by column chromatography (silica gel, 20% ethyl acetate in pet-ether) to provide methyl 1-chloro-8-methyl-8,9-dihydrofuro[2,3-h]isoquinoline-6-carboxylate (0.12 g, 56% yield) as an off-white solid. LC-MS: m/z 278.2 (M+H).

Intermediate 50F: 1-chloro-8-methyl-8,9-dihydrofuro[2,3-h]isoquinoline-6-carboxamide

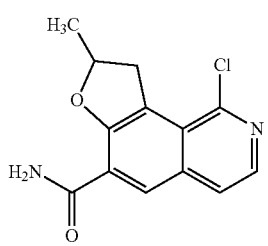

(50F)

A stirred solution of methyl 1-chloro-8-methyl-8,9-dihydrofuro[2,3-h]isoquinoline-6-carboxylate (0.05 g, 0.180 mmol) in methanol (10 mL) was purged with ammonia gas at −78° C. for 5 min. The reaction vessel was sealed. The reaction mixture was stirred at room temperature for 3 h. The solvent was removed under reduced pressure and the crude compound was purified by column chromatography (silica gel, 2% methanol in chloroform) to provide 1-chloro-8-methyl-8,9-dihydrofuro[2,3-h]isoquinoline-6-carboxamide (0.035 g, 63% yield) as an off-white solid. LC-MS: m/z 262.4 (M+H)

Example 50: 1-(((2S,3S,4S)-3-ethyl-4-fluoro-5-oxotetrahydrofuran-2-yl)methoxy)-8-methyl-8,9-dihydrofuro[2,3-h]isoquinoline-6-carboxamide This compound was synthesized according to the general procedure outlined in Example 16 using appropriate intermediates and isolated as a mixture of diastereomers. $^1$H NMR (400 MHz, DMSO-$d_6$) δ 8.79 (d, J=11.0 Hz, 1H), 8.20 (s, 1H), 7.83 (br. s., 1H), 7.79 (d, J=5.9 Hz, 1H), 7.59 (br. s., 1H), 7.42 (d, J=5.9 Hz, 1H), 5.26-5.13 (m, 1H), 4.93 (d, J=5.6 Hz, 1H), 4.80 (d, J=5.6 Hz, 1H), 4.48 (dd, J=11.1, 3.5 Hz, 1H), 4.39-4.25 (m, 1H), 4.19-4.04 (m, 2H), 1.62-1.55 (m, 2H), 1.52 (d, J=6.1 Hz, 3H), 1.01 (td, J=7.3, 2.2 Hz, 3H). LC-MS: m/z 389.4 (M+H).

Example 50 was separated into the individual diastereomers via SFC chromatography.

Example 51: $^1$H NMR (400 MHz, DMSO-$d_6$) δ 8.79 (d, J=11.0 Hz, 1H), 8.20 (s, 1H), 7.83 (br. s., 1H), 7.79 (d, J=5.9 Hz, 1H), 7.59 (br. s., 1H), 7.42 (d, J=5.9 Hz, 1H), 5.26-5.13 (m, 1H), 4.93 (d, J=5.6 Hz, 1H), 4.80 (d, J=5.6 Hz, 1H), 4.48 (dd, J=11.1, 3.5 Hz, 1H), 4.39-4.25 (m, 1H), 4.19-4.04 (m, 2H), 1.62-1.55 (m, 2H), 1.52 (d, J=6.1 Hz, 3H), 1.01 (td, J=7.3, 2.2 Hz, 3H). LC-MS: m/z 388.2 (M+H).

Example 52: $^1$H NMR (400 MHz, DMSO-$d_6$) δ 8.79 (d, J=11.0 Hz, 1H), 8.20 (s, 1H), 7.83 (br. s., 1H), 7.79 (d, J=5.9 Hz, 1H), 7.59 (br. s., 1H), 7.42 (d, J=5.9 Hz, 1H), 5.26-5.13 (m, 1H), 4.93 (d, J=5.6 Hz, 1H), 4.80 (d, J=5.6 Hz, 1H), 4.48 (dd, J=11.1, 3.5 Hz, 1H), 4.39-4.25 (m, 1H), 4.19-4.04 (m, 2H), 1.62-1.55 (m, 2H), 1.52 (d, J=6.1 Hz, 3H), 1.01 (td, J=7.3, 2.2 Hz, 3H). LC-MS: m/z 388.2 (M+H).

Example 53

1-(((2S,3R)-3-ethyl-5-oxotetrahydrofuran-2-yl)methoxy)-8-methyl-8,9-dihydrofuro[2,3-h]isoquinoline-6-carboxamide

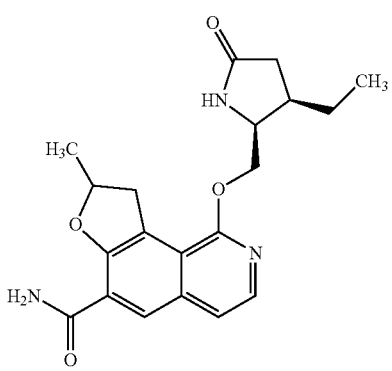

(53)

This compound was synthesized by following the general procedure outlined in Example 16 using appropriate intermediates and isolated as a mixture of diastereomers. $^1$H NMR (400 MHz, DMSO-$d_6$) δ 8.20 (s, 1H), 7.94 (d, J=10.8 Hz, 1H), 7.87-7.71 (m, 2H), 7.58 (br. s., 1H), 7.42 (d, J=5.9 Hz, 1H), 5.30-5.07 (m, 1H), 4.52-4.32 (m, 2H), 4.09-3.97 (m, 1H), 2.46 (br. s., 1H), 2.29-2.20 (m, 1H), 2.13-2.00 (m, 1H), 1.58 (d, J=4.9 Hz, 1H), 1.51 (dd, J=8.1, 6.4 Hz, 3H), 1.42-1.31 (m, 1H), 0.91 (td, J=7.3, 2.6 Hz, 3H). LC-MS: m/z 371.4 (M+H).

Example 54

1-(((2S,3R)-3-ethyl-5-oxopyrrolidin-2-yl)methoxy)-8,9-dihydrofuro[2,3-h]isoquinoline-6-carboxamide

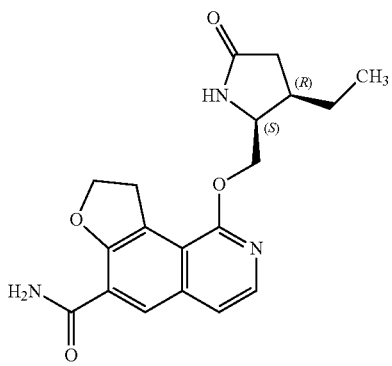
(54)

Intermediate 54A: tert-butyl 4-bromo-2-fluorobenzoate

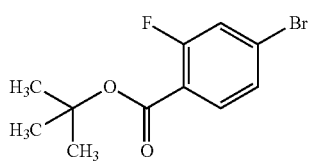
(54A)

To a stirred solution of 4-bromo-2-fluorobenzoic acid (1.2 g, 5.5 mmol) in t-butanol (10 mL) and tetrahydrofuran (20 mL) were added BOC$_2$O (1.27 mL, 5.5 mmol) and DMAP (0.08 g, 0.7 mmol). The reaction mixture was heated at 80° C. for 12 h. The reaction mixture was cooled to room temperature and volatiles were evaporated to dryness under reduced pressure. The residue was diluted with water and extracted with ethyl acetate. The combined organic extracts were washed with water and brine, then dried over sodium sulphate and concentrated. The crude compound was purified by column chromatography (silica gel, 35% ethyl acetate in pet ether) to provide tert-butyl 4-bromo-2-fluorobenzoate (560 mg, 37% yield) as an off-white solid. $^1$H NMR (400 MHz, CDCl$_3$) δ 7.73 (d, J=8.51 Hz, 1H) 7.27-7.32 (m, 2H) 1.59 (s, 11H).

Intermediate 54B: tert-butyl 4-bromo-2,3-dihydrobenzofuran-7-carboxylate

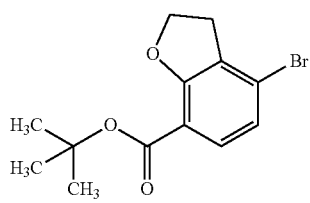
(54B)

To a stirred solution of tert-butyl 4-bromo-2-fluorobenzoate (500 mg, 1.82 mmol) in tetrahydrofuran (12 mL) was added LDA (2 M in THF) (0.91 mL, 1.82 mmol) at -78° C. The reaction mixture was stirred for 2 h at the same temperature. Oxirane (2.5 M in THF) (2.18 mL, 5.45 mmol) was added and the reaction mixture was stirred for 4 h at -78° C. The reaction mixture was allowed to warm room temperature and stirred for 14 h. The reaction was quenched with aqueous ammonium chloride solution. The reaction mixture was extracted with ethyl acetate. The combined organic extracts were washed with water and brine, then dried over sodium sulphate and concentrated. The crude compound was purified by column chromatography (silica gel, 30% ethyl acetate in pet ether) to provide tert-butyl 4-bromo-2,3-dihydrobenzofuran-7-carboxylate (230 mg, 4% yield) as an off-white solid. $^1$H NMR (400 MHz, CDCl$_3$) δ 7.53 (dt, J=8.51, 0.75 Hz, 1H) 6.98 (d, J=8.51 Hz, 1H) 4.75 (t, J=8.88 Hz, 2H) 3.11-3.26 (m, 2H) 1.47-1.65 (m, 9H).

Intermediate 54C: 4-bromo-2,3-dihydrobenzofuran-7-carboxylic acid

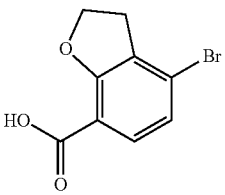
(54C)

To a stirred solution of tert-butyl 4-bromo-2,3-dihydrobenzofuran-7-carboxylate (120 mg, 0.401 mmol) in dichloromethane (3 mL) was added TFA (1 mL, 12.98 mmol). The reaction mixture was stirred at room temperature for 15 h. The volatiles were evaporated to dryness under reduced pressure. The residue was diluted with hexane and the mixture was stirred for 10 min. The precipitated solid was filtered, washed with hexane, and dried under vacuum to provide 4-bromo-2,3-dihydrobenzofuran-7-carboxylic acid (55 mg, 56% yield) as a TFA salt. The product was taken to the next step without further purification. $^1$H NMR (400 MHz, DMSO-d$_6$) δ 12.55 (Br, 1H) 7.51 (d, J=8.53 Hz, 1H) 7.08 (d, J=8.53 Hz, 1H) 4.68 (t, J=9.04 Hz, 2H) 3.20 (t, J=8.78 Hz, 2H).

Intermediate 54D: 4-bromo-N-(tert-butyl)-2,3-dihydrobenzofuran-7-carboxamide

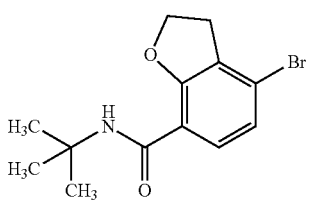
(54D)

To a stirred solution of 4-bromo-2,3-dihydrobenzofuran-7-carboxylic acid (2.8 g, 11.5 mmol), HATU (4.38 g, 11.5 mmol) and TEA (4.82 mL, 34.6 mmol) in dichloromethane (25 mL) was added 2-methylpropan-2-amine (1.221 mL, 11.5 mmol). The reaction mixture was stirred under nitrogen atmosphere for 4 h. The volatiles were evaporated to dryness under reduced pressure and the residue was diluted with water and extracted with ethyl acetate. The combined organic extracts were washed with water and brine, then dried over sodium sulphate and concentrated. The crude compound was purified by column chromatography (silica gel, 55% ethyl acetate in pet ether) to provide 4-bromo-N-(tert-butyl)-2,3-dihydrobenzofuran-7-carboxamide (2.2 g, 64% yield). $^1$H NMR (400 MHz, DMSO-d$_6$) δ 7.55 (d, J=8.56 Hz, 1H) 7.42 (s, 1H) 7.15 (d, J=8.31 Hz, 1H) 4.79 (t, J=8.80 Hz, 2H) 3.23 (t, J=8.68 Hz, 2H) 1.37 (s, 9H).

Intermediate 54E: 7-(tert-butylcarbamoyl)-2,3-dihydrobenzofuran-4-carboxylic acid

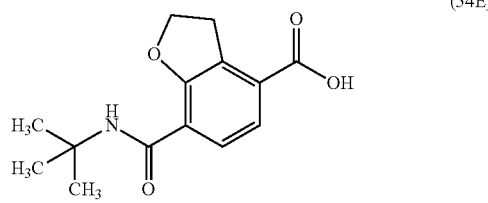

(54E)

To a stirred solution of 4-bromo-N-(tert-butyl)-2,3-dihydrobenzofuran-7-carboxamide (50 mg, 0.15 mmol) in tetrahydrofuran (10 mL) was added n-butyllithium (2.5 M in hexanes, 0.15 mL, 0.37 mmol) at −78° C. under an argon atmosphere. The reaction mixture was stirred at the same temperature for 45 min. The reaction mixture was purged with CO$_2$ gas for 20 min and stirring was continued for 45 min. The reaction was quenched with the addition of aqueous 1.5 N HCl solution. The reaction mixture was extracted with ethyl acetate. The combined organic extracts were washed with water and brine, then dried over sodium sulphate and concentrated to afford 7-(tert-butylcarbamoyl)-2,3-dihydrobenzofuran-4-carboxylic acid (50 mg, 59% yield) as a pale yellow solid. LC-MS: m/z 264.2 (M+H). This compound was taken to the next step without further purification.

Intermediate 54F: N7-(tert-butyl)-N4-(2,2-dimethoxyethyl)-2,3-dihydrobenzofuran-4,7-dicarboxamide

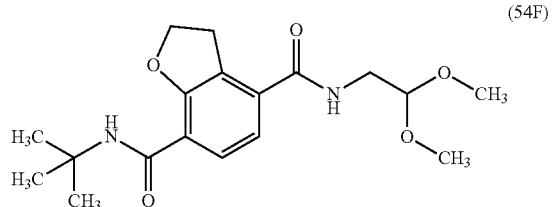

(54F)

To a stirred solution of 7-(tert-butylcarbamoyl)-2,3-dihydrobenzofuran-4-carboxylic acid (63 mg, 0.24 mmol), HATU (91 mg, 0.24 mmol), TEA (0.1 mL, 0.72 mmol) in dichloromethane (5 mL) was added aminoacetaldehyde dimethylacetal (25.2 mg, 0.24 mmol). The reaction mixture was stirred under nitrogen atmosphere for 4 h. The volatiles were evaporated to dryness and the residue was diluted with water and extracted with ethyl acetate. The combined organic extracts were washed with water, brine, then dried over sodium sulphate and concentrated to afford N7-(tert-butyl)-N4-(2,2-dimethoxyethyl)-2,3-dihydrobenzofuran-4,7-dicarboxamide (90 mg) as a light brown solid. LC-MS: m/z 351.5 (M+H). This compound was taken to the next step without further purification.

Intermediate 54G: 1-oxo-1,2,8,9-tetrahydrofuro[2,3-h]isoquinoline-6-carboxamide

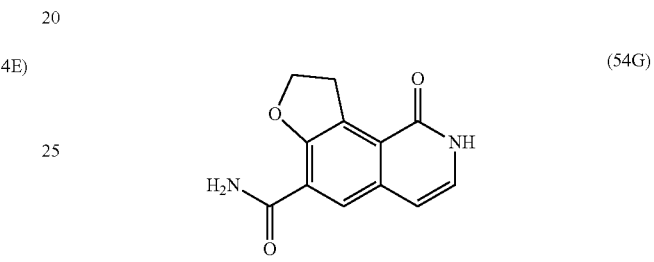

(54G)

A stirred solution of N7-(tert-butyl)-N4-(2,2-dimethoxyethyl)-2,3-dihydrobenzofuran-4,7-dicarboxamide (60 mg, 0.17 mmol) in sulfuric acid (0.4 mL, 7.5 mmol) was heated at 90° C. for 48 h and cooled to room temperature. The reaction mixture was poured into saturated aqueous sodium bicarbonate solution and extracted with ethyl acetate. The combined organic extracts were washed with water, brine, then dried over sodium sulphate and concentrated to provide 1-oxo-1,2,8,9-tetrahydrofuro[2,3-h]isoquinoline-6-carboxamide (50 mg) as a light brown solid. $^1$H NMR (400 MHz, DMSO-d$_6$) δ 8.30 (s, 1H) 7.77 (d, J=8.53 Hz, 1H) 7.67 (br. s., 1H) 7.56 (s, 1H) 7.54 (s, 1H) 7.48 (d, J=1.00 Hz, 1H) 7.34 (br. s., 1H) 4.79 (t, J=8.78 Hz, 2H) 3.60 (t, J=8.78 Hz, 2H).

Intermediate 54H: 1-chloro-8,9-dihydrofuro[2,3-h]isoquinoline-6-carbonitrile

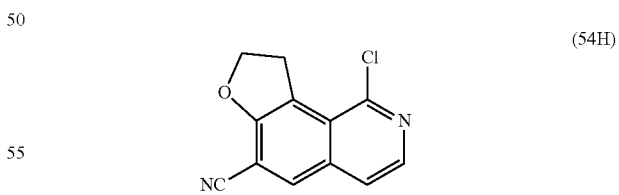

(54H)

A stirred solution on 1-oxo-1,2,8,9-tetrahydrofuro[2,3-h]isoquinoline-6-carboxamide (50 mg, 0.26 mmol) in POCl$_3$ (2 mL, 21.5 mmol) was heated at 110° C. for 3 h and cooled to room temperature. The solvent was removed under reduced pressure and the crude compound was purified by column chromatography (silica gel, 2% methanol in chloroform) to provide 1-chloro-8,9-dihydrofuro[2,3-h]isoquinoline-6-carbonitrile (43 mg) as an off-white solid. LC-MS: m/z 231.1 (M+H).

Intermediate 54I: 1-(((2S,3R)-3-ethyl-5-oxopyrrolidin-2-yl)methoxy)-8,9-dihydrofuro[2,3-h]isoquinoline-6-carbonitrile

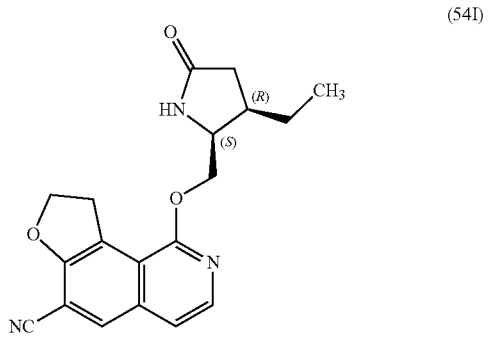

(54I)

To a stirred solution of 1-chloro-8,9-dihydrofuro[2,3-h]isoquinoline-6-carbonitrile (40 mg, 0.17 mmol) and (4R,5S)-4-ethyl-5-(hydroxymethyl)pyrrolidin-2-one (24.8 mg, 0.17 mmol) in THF (10 mL) was added sodium hydride (6.94 mg, 0.17 mmol) in two portions under nitrogen atmosphere. The reaction mixture was heated at 60° C. for 14 h. The reaction mixture was cooled to room temperature and diluted with water and extracted with ethyl acetate. The combined organic extracts were washed with water, brine, then dried over sodium sulphate and concentrated provide 1-(((2S,3R)-3-ethyl-5-oxopyrrolidin-2-yl)methoxy)-8,9-dihydrofuro[2,3-h]isoquinoline-6-carbonitrile (56 mg, 22% yield) as a light brown solid. LC-MS: m/z 338.1 (M+H).

Example 54: 1-(((2S,3R)-3-ethyl-5-oxopyrrolidin-2-yl)methoxy)-8,9-dihydrofuro[2,3-h]isoquinoline-6-carboxamide A stirred solution of 1-(((2S,3R)-3-ethyl-5-oxopyrrolidin-2-yl)methoxy)-8,9-dihydrofuro[2,3-h]isoquinoline-6-carbonitrile (55 mg, 0.037 mmol) in sulfuric acid (1 mL, 18.76 mmol) was heated at 60° C. for 45 min and cooled to room temperature. The reaction mixture was diluted with MeOH and purified by prep-HPLC to provide 1-(((2S,3R)-3-ethyl-5-oxopyrrolidin-2-yl)methoxy)-8,9-dihydrofuro[2,3-h]isoquinoline-6-carboxamide as a pale yellow solid. MS: m/z 356.2 (M+H).

Example 55

1-(((2S,3R)-3-ethyl-5-oxopyrrolidin-2-yl)methoxy)-2,7-phenanthroline-6-carboxamide

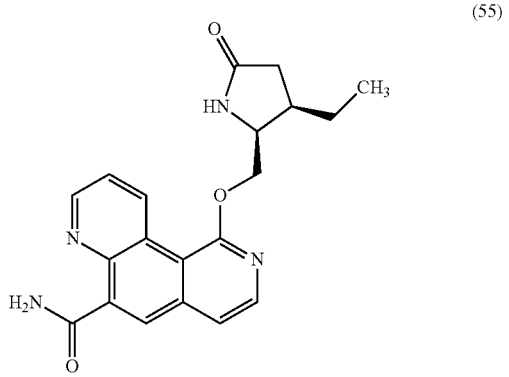 [SMILES: CC[C@@H]1CC(=O)N[C@@H]1COc1nccc2cc(C(N)=O)c3ncccc3c12]

(55)

Intermediate 55A: methyl 5-amino-4-iodo-2-methylbenzoate

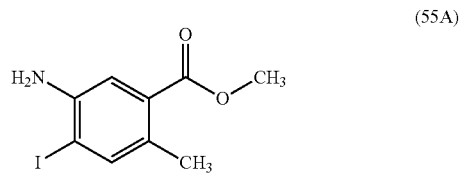

(55A)

To a stirred solution of methyl 5-amino-2-methylbenzoate (7.0 g, 42.4 mmol) in acetic acid (90 mL) was added N-iodosuccinimide (9.82 g, 43.6 mmol) portion wise at room temperature. The mixture was stirred for 1 h and then solvent was removed under reduced pressure. The resulting crude mass was diluted with water and basified using saturated $Na_2CO_3$ solution. The turbid solution was extracted with ethyl acetate and the combined organic extracts were washed with water and brine, then dried over sodium sulphate and concentrated. The crude compound was purified by column chromatography (silica gel, 55% ethyl acetate in pet ether) to provide methyl 5-amino-4-iodo-2-methylbenzoate (5.7 g, 46% yield) as a yellow liquid. $^1H$ NMR (300 MHz, DMSO-$d_6$) δ 7.53 (s, 1H), 7.23 (s, 1H), 5.26 (s, 2H), 3.78 (s, 3H), 2.30 (s, 3H). LC-MS: m/z 292 (M+H).

Intermediate 55B: 8-iodo-6-methylquinoline-5-carboxylic acid

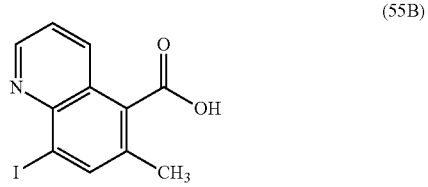

(55B)

To a stirred solution of methyl 5-amino-4-iodo-2-methylbenzoate (5.8 g, 19.9 mmol) in water (20 mL) and $H_2SO_4$ (20 mL) were added glycerol (7.28 mL, 100 mmol) followed by nitrobenzene (20.4 mL, 200 mmol) at room temperature. The reaction mixture was heated at 140° C. for 16 h and cooled to room temperature. The reaction mixture was basified to pH ~8 with saturated NaOH solution and washed with ethyl acetate. The aqueous solution was acidified to pH ~ 5 by 1.5 N HCl solution. The precipitated solid was filtered, washed with water, and dried under vacuum to provide 8-iodo-6-methylquinoline-5-carboxylic acid (1.7 g, 27% yield) as a brown solid. $^1H$ NMR (400 MHz, DMSO-$d_6$) δ=8.96 (dd, J=1.8, 4.3 Hz, 1H), 8.38 (s, 1H), 8.24 (dd, J=2.0, 8.5 Hz, 1H), 7.66 (dd, J=4.0, 8.5 Hz, 1H), 2.48 (s, 3H). LC-MS: m/z 314 (M+H).

Intermediate 55C: 8-iodo-6-methylquinoline-5-carboxamide

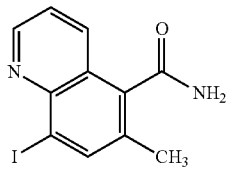

(55C)

To a stirred solution of 8-iodo-6-methylquinoline-5-carboxylic acid (1.7 g, 5.43 mmol) in DCM (15 mL) was added oxalyl chloride (0.475 mL, 5.43 mmol) followed by 2 drops of DMF at 0° C. The reaction mixture was allowed to come to room temperature and stirred for 1 h. The solvent was evaporated under reduced pressure and the residue was dissolved in THF (10 mL). The solution was purged with ammonia for 5 min. and stirred for 1 h at room temperature. The reaction mixture was diluted with water and extracted with ethyl acetate. The combined organic extracts were washed with water and brine, then dried over anhydrous sodium sulphate and concentrated. The crude compound was washed with diethyl ether and dried under vacuum to provide 8-iodo-6-methylquinoline-5-carboxamide (1.3 g, 77% yield) as an off-white solid. $^1$H NMR (400 MHz, DMSO-$d_6$) δ 8.91 (dd, J=1.5, 4.0 Hz, 1H), 8.31 (s, 1H), 8.13 (dd, J=1.5, 8.5 Hz, 1H), 8.03 (br s, 1H), 7.93 (s, 1H), 7.88 (br s, 1H), 7.61 (dd, J=4.0, 8.5 Hz, 1H), 2.42 (s, 3H). LC-MS: m/z 313 (M+H).

Intermediate 55E: (E)-N-((dimethylamino)methylene)-8-iodo-6-methylquinoline-5-carboxamide

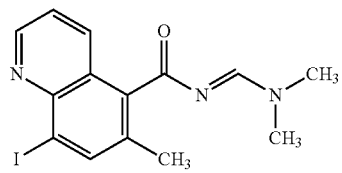

(55E)

To a stirred solution of 8-iodo-6-methylquinoline-5-carboxamide (1.3 g, 4.17 mmol) in THF (20 mL) was added DMF-DMA (2.79 mL, 20.83 mmol). The reaction mixture was heated at 65° C. for 16 h and cooled to room temperature. The solvent was evaporated under reduced pressure and the residue was triturated with diethyl ether for 10 min. The precipitated solid was filtered, washed with water, and dried under vacuum to provide (E)-N-((dimethylamino)methylene)-8-iodo-6-methylquinoline-5-carboxamide (1.1 g, 72% yield) as a white solid. $^1$H NMR (400 MHz, DMSO-$d_6$) δ 8.91-8.89 (m, 1H), 8.67-8.66 (m, 1H), 8.30-8.29 (m, 1H), 8.17-8.13 (m, 1H), 7.58-7.53 (m, 1H), 3.22 (s, 3H), 3.02-2.99 (s, 3H), 2.43 (s, 3H). LC-MS: m/z 368.1 (M+H).

Intermediate 55E: 6-iodo-2,7-phenanthrolin-1(2H)-one

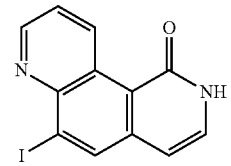

(55E)

To a pre-heated (65° C.) solution of (E)-N-((dimethylamino)methylene)-8-iodo-6-methylquinoline-5-carboxamide (1.1 g, 3 mmol) in THF (5 mL) was carefully added potassium tert-butoxide (3 mL, 3 mmol, 1.0 M in THF) over a period of 20 min. The reaction mixture was stirred for 2 h., then diluted with cold water and acidified to pH ~ 5 using aqueous 1.5 N HCl solution. The precipitated solid was filtered, washed with water, and dried to provide 6-iodo-2,7-phenanthrolin-1(2H)-one (0.6 g, 62% yield) as a yellow solid. $^1$H NMR (400 MHz, DMSO-$d_6$) δ 11.94 (br s, 1H), 10.43 (dd, J=1.5, 8.5 Hz, 1H), 9.00 (dd, J=1.8, 4.3 Hz, 1H), 8.80 (s, 1H), 7.78 (dd, J=4.0, 8.5 Hz, 1H), 7.56 (t, J=6.3 Hz, 1H), 6.82 (d, J=7.0 Hz, 1H). LC-MS: m/z 368.1 (M+H).

Intermediate 55F: 1-oxo-1,2-dihydro-2,7-phenanthroline-6-carbonitrile

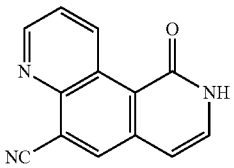

(55F)

To a stirred solution of 6-iodo-2,7-phenanthrolin-1(2H)-one (0.6 g, 1.86 mmol) in DMF was added zinc cyanide (0.55 g, 4.7 mmol) followed by Pd(Ph$_3$P)$_4$ (0.215 g, 0.19 mmol) at room temperature in a pressure tube. The pressure tube was closed and heated at 100° C. for 6 h. The reaction mixture was cooled to room temperature and filtered through celite. The celite was rinsed with ethyl acetate and the filtrate was evaporated under reduced pressure. The residue was diluted with cold water and stirred for 10 min. The precipitated solid was filtered, washed with water and dried to provide 1-oxo-1,2-dihydro-2,7-phenanthroline-6-carbonitrile (0.30 g, 85% yield) as a yellow solid. $^1$H NMR (300 MHz, DMSO-$d_6$) δ 12.17 (br s, 1H), 10.46 (br d, J=9.1 Hz, 1H), 9.09 (br d, J=2.6 Hz, 1H), 8.78 (s, 1H), 7.88 (dd, J=4.3, 8.9 Hz, 1H), 7.65 (br s, 1H), 6.91 (d, J=6.8 Hz, 1H). LC-MS: m/z 222.1 (M+H).

Intermediate 55G: 1-chloro-2,7-phenanthroline-6-carbonitrile

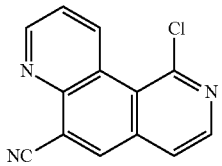

(55G)

To a stirred solution of 1-oxo-1,2-dihydro-2,7-phenanthroline-6-carbonitrile (0.35 g, 1.6 mmol) in toluene (15 mL) were added DIPEA (0.83 mL, 4.8 mmol) followed by POCl$_3$ (1.5 mL, 15.8 mmol) at room temperature. The reaction mixture was heated at 120° C. for 3 h and cooled to room temperature. The solvent was evaporated under reduced pressure and residue was diluted with cold saturated NaHCO$_3$ solution. The precipitated solid was filtered, washed with water, and dried under vacuum to provide 1-chloro-2,7-phenanthroline-6-carbonitrile (0.2 g, 53% yield) as a brown solid. $^1$H NMR (300 MHz, DMSO-d$_6$) δ 10.18 (br d, J=7.6 Hz, 1H), 9.20 (br s, 1H), 9.05 (s, 1H), 8.72 (br d, J=4.9 Hz, 1H), 8.21 (br d, J=4.9 Hz, 1H), 8.05-7.96 (m, 1H). LC-MS: m/z 240.4 (M+H).

Example 55: 1-(((2S,3R)-3-ethyl-5-oxopyrrolidin-2-yl)methoxy)-2,7-phenanthroline-6-carboxamide This compound was synthesized according to the general procedure outlined in Example 16 using the appropriate intermediates. $^1$H NMR (400 MHz, DMSO-d$_6$) δ 9.89 (dd, J=8.8, 1.8 Hz, 1H), 9.83 (br. s., 1H), 9.07 (dd, J=4.3, 1.8 Hz, 1H), 8.79 (s, 1H), 8.38 (d, J=5.3 Hz, 1H), 8.17 (s, 1H), 8.03 (br. s., 1H), 7.86-7.77 (m, 2H), 4.79 (dd, J=11.5, 5.3 Hz, 1H), 4.60 (dd, J=11.3, 4.3 Hz, 1H), 4.22-4.10 (m, 1H), 2.68 (t, J=1.8 Hz, 1H), 2.37-2.23 (m, 1H), 2.08 (dd, J=16.4, 10.4 Hz, 1H), 1.69-1.54 (m, 1H), 1.42-1.23 (m, 1H), 0.88 (t, J=7.4 Hz, 3H). LC-MS: m/z 365.4 (M+H).

Example 56

1-(((2S,3S,4S)-3-ethyl-4-fluoro-5-oxopyrrolidin-2-yl)methoxy)-2,7-phenanthroline-6-carboxamide

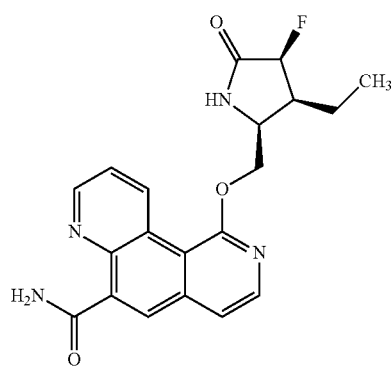

(56)

This compound was synthesized by following same procedure as outlined for Example 16 using appropriate intermediates. $^1$H NMR (400 MHz, DMSO-d$_6$) δ 9.94 (dd, J=8.7, 1.6 Hz, 1H), 9.86 (br. s., 1H), 9.06 (dd, J=4.2, 1.5 Hz, 1H), 8.97 (s, 1H), 8.78 (s, 1H), 8.37 (d, J=5.4 Hz, 1H), 8.00 (br. s., 1H), 7.91-7.74 (m, 2H), 4.96 (dd, J=5.6, 53.0 Hz, 1H), 4.72 (dd, J=11.5, 4.6 Hz, 1H), 4.62 (dd, J=11.0, 7.8 Hz, 1H), 4.29 (br. s., 1H), 2.73-2.64 (m, 1H), 1.61 (quin, J=7.4 Hz, 2H), 1.00 (t, J=7.3 Hz, 3H). LC-MS: m/z 383.4 (M+H).

Additional compounds of the invention prepared according to the general methods outlined above are below.

TABLE 1

| Ex. No. | Structure | LCMS |
|---|---|---|
| 57 | 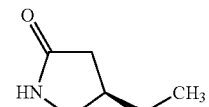 | 371.2 |
| 58 | 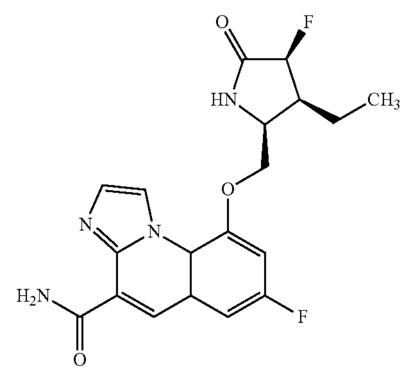 [SMILES: CC[C@@H]1[C@H](F)C(=O)N[C@@H]1COC1=CC(F)=CC2C=C(C(N)=O)c3nccn3C12] | 389.0 |
| 59 | 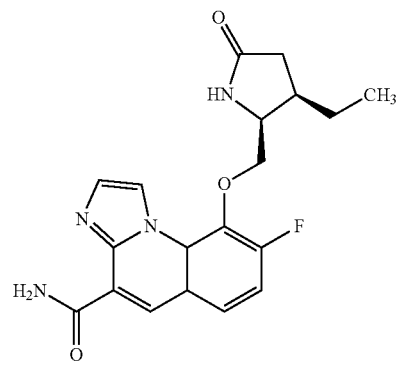 [SMILES: CC[C@@H]1CC(=O)N[C@@H]1COC1=C(F)C=CC2C=C(C(N)=O)c3nccn3C12] | 371.0 |

TABLE 1-continued

| Ex. No. | Structure | LCMS |
|---|---|---|
| 60 | 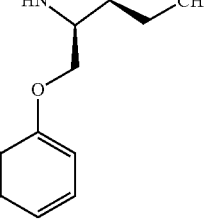 | 335.1 |
| 61 | 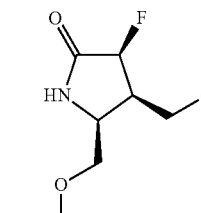 | 400.2 |
| 62 | 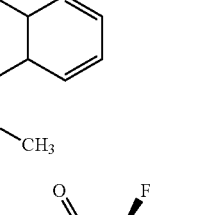 | 386.1 |
| 63 | 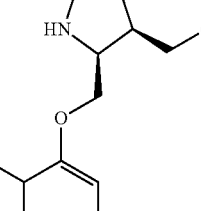 | 402.2 |

HPLC Conditions:

Method A. Sunfire C18 (4.6×150 mm), 3.5 micron, mobile phase A: 95:5 water/MeCN, 0.05% TFA; mobile phase B: 95:5 MeCN/water, 0.05% TFA; 1 mL\min, 12 min gradient.

Method B. Xbridge Phenyl (4.6×150 mm), 3.5 micron, mobile phase A: 95:5 water/MeCN, 0.05% TFA; mobile phase B: 95:5 MeCN/water, 0.05% TFA; 1 mL\min, 12 min gradient.

Method C. Ascentis Express C18 (2.1×50 mm), 2.7 micron, mobile phase A: 95:5 water/MeCN, 10 mM NH$_4$OAc; mobile phase B: 5:95 water/MeCN, 10 mM NH4OAc; 1.1 mL\min, 3 min gradient, 50° C.

Method D. Ascentis Express C18 (2.1×50 mm), 2.7 micron, mobile phase A: 95:5 water/MeCN, 0.01% TFA; mobile phase B: 5:95 water/MeCN, 0.01% TFA; 1.1 mL\min, 3 min gradient, 50° C.

Method E. Waters Acquity UPLC BEH C18, 2.1×50 mm, 1.7 micron; mobile phase A: 5:95 MeCN:water with 10 mM ammonium acetate; mobile phase B: 95:5 MeCN:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

Method F. Column: Waters Acquity UPLC BEH C18, 2.1×50 mm, 1.7 micron; mobile phase A: 5:95 MeCN:water with 0.1% trifluoroacetic acid; mobile phase B: 95:5 MeCN:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

Method G. Ascentis Express C18 (4.6×50 mm), 2.7 micron, mobile phase A: 95:5 water/MeCN, 10 mM NH$_4$OAc; mobile phase B: 5:95 water/MeCN, 10 mM NH$_4$OAc; 4 mL\min, 4 min gradient, 50° C.

Method H. Ascentis Express C18 (2.1×50 mm), 2.7 micron, mobile phase A: 95:5 water/MeCN, 0.1% TFA; mobile phase B: 5:95 water/MeCN, 0.1% TFA; 1.1 mL\min, 3 min gradient, 50° C.

Method I. Sunfire C18 (4.6×150 mm), 3.5 micron, mobile phase A: 95:5 water/MeCN, 0.05% TFA; mobile phase B: 95:5 MeCN/water, 0.05% TFA; 1 mL\min, 18 min gradient.

Method J. Xbridge Phenyl (4.6×150 mm), 3.5 micron, mobile phase A: 95:5 water/MeCN, 0.05% TFA; mobile phase B: 95:5 MeCN/water, 0.05% TFA; 1 mL\min, 18 min gradient.

Method K. Xbridge BEH XP C18 (2.1×50 mm), 2.5 micron, mobile phase A: 95:5 water/MeCN, 10 mM NH$_4$OAc; mobile phase B: 5:95 water/MeCN, 10 mM NH$_4$OAc; 1.1 mL\min, 3 min gradient, 50° C.

Method L. Xbridge BEH XP C18 (2.1×50 mm), 2.5 micron, mobile phase A: 95:5 water/MeCN, 0.01% TFA; mobile phase B: 5:95 water/MeCN, 0.01% TFA; 1.1 mL\min, 3 min gradient, 50° C.

Method M. Xbridge Phenyl (4.6×150 mm), 3.5 micron, mobile phase A: 95:5 water/MeCN, 0.05% TFA; mobile phase B: 95:5 MeCN/water, 0.05% TFA; 1 mL\min, 25 min gradient.

Method N. Waters XBridge C18, 2.1 mm×50 mm, 1.7 m particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min.

Biological Assays

The pharmacological properties of the compounds of this invention may be confirmed by a number of biological assays. The exemplified biological assays, which follow, have been carried out with compounds of the invention.

IRAK4 Inhibition Assay

The assays were performed in U-bottom 384-well plates. The final assay volume was 30 μL prepared from 15 μL additions of enzyme and substrates (fluoresceinated peptide and ATP) and test compounds in assay buffer (20 mM HEPES pH 7.2, 10 mM $MgCl_2$, 0.015% Brij 35 and 4 mM DTT). The reaction was initiated by the combination of IRAK4 with substrates and test compounds. The reaction mixture was incubated at room temperature for 60 min. and terminated by adding 45 μL of 35 mM EDTA to each sample. The reaction mixture was analyzed on the Caliper LABCHIP® 3000 (Caliper, Hopkinton, MA) by electrophoretic separation of the fluorescent substrate and phosphorylated product. Inhibition data were calculated by comparison to no enzyme control reactions for 100% inhibition and vehicle-only reactions for 0% inhibition. The final concentrations of reagents in the assays are ATP, 500 μM; FL-IPTSPITTTYFFFKKK peptide 1.5 μM; IRAK4, 0.6 nM; and DMSO, 1.6%.

IRAK4 Whole Blood Assay

Human whole blood containing the anti-coagulant ACD-A was plated in 384-well plate (25 μL/well) and incubated with compounds for 60 minutes at 37° C. in a 5% $CO_2$ incubator. The blood was stimulated with a TLR2 agonist, 10 μg/mL final concentration of lipoteichoic acid (Invivogen, San Diego, CA) in 25 μL RPMI (Gibco) for 5 hours in a 5% $CO_2$ incubator. At the end of the incubation, plates were centrifuged at 2300 rpm for 5 minutes. Supernatants were harvested and analyzed for IL-6 levels by Flow Cytometry beads assay (BD Biosciences, San Jose, CA).

TABLE A

IRAK4 Inhibition Data

| Ex. No. | IRAK4 $IC_{50}$, μM | Whole Blood $IC_{50}$, μM | HPLC Rt, min | HPLC Conditions |
|---|---|---|---|---|
| 1 | 0.0206 | 1.421 | 1.11 | C |
| 2 | 0.0150 | 0.306 | 1.37 | C |
| 3 | 0.0017 | 0.152 | 1.35 | C |
| 4 | 0.0026 | 0.593 | 1.37 | C |
| 5 | 0.0013 | 0.280 | 9.41 | I |
| 6 | 0.5180 | — | 1.27 | K |
| 7 | 0.2426 | — | 1.09 | C |
| 10 | 0.0019 | 1.391 | 1.53 | C |
| 11 | 0.0034 | 3.455 | 8.69 | I |
| 12 | 0.0022 | 10.000 | 9.26 | I |
| 13 | 1.4302 | — | 1.23 | K |
| 14 | 0.0010 | 0.557 | 1.50 | K |
| 15 | 0.0082 | 2.652 | 1.25 | K |
| 16 | 0.0110 | 1.519 | 9.80 | I |
| 17 | 0.0047 | 0.094 | 10.42 | I |
| 18 | 0.0197 | 20.000 | 1.43 | C |
| 19 | 0.0032 | 0.485 | 11.39 | J |
| 20 | 0.0088 | 0.158 | 1.32 | C |
| 21 | 0.0107 | 0.533 | 1.65 | C |
| 22 | 0.0021 | 4.784 | 1.32 | K |
| 23 | 0.2615 | — | 1.34 | K |
| 24 | 0.1758 | — | 1.34 | K |
| 25 | 1.9325 | — | 1.08 | K |
| 26 | 0.0804 | — | 1.04 | K |
| 27 | 1.8203 | — | 0.72 | K |
| 28 | 0.2252 | — | 1.52 | C |
| 29 | 0.6010 | — | 1.63 | C |
| 30 | 1.7214 | — | 1.71 | K |
| 31 | 1.0614 | — | 1.70 | K |
| 32 | 0.0620 | — | 5.38 | A |
| 33 | 0.264 | — | 1.40 | K |
| 34 | 0.0009 | 0.279 | 1.27 | K |
| 35 | 0.0026 | 1.648 | 9.75 | M |
| 36 | 0.0007 | 0.159 | 1.21 | K |
| 37 | 0.0034 | 0.586 | 1.31 | C |
| 38 | 0.0603 | — | 7.39 | B |
| 39 | 0.0159 | 0.078 | 7.97 | A |
| 40 | 0.0391 | — | 7.83 | I |
| 41 | 0.0422 | — | 11.36 | I |
| 42 | 0.2900 | — | 11.12 | I |
| 43 | 0.0162 | — | 6.08 | A |
| 44 | 0.0096 | 1.030 | 7.85 | A |
| 45 | 0.0700 | — | 1.07 | K |
| 46 | 0.0097 | 1.081 | 1.24 | C |
| 47 | 0.0781 | — | 1.36 | K |
| 48 | 0.0169 | 2.246 | 1.52 | K |
| 49 | 0.0291 | 2.018 | 1.35 | C |
| 50 | 0.0018 | 0.873 | 1.18 | K |
| 51 | 0.0031 | 0.399 | 6.89 | A |
| 52 | 0.0013 | — | 6.65 | A |
| 53 | 0.0049 | 5.569 | 1.22 | K |
| 54 | 0.0136 | 1.098 | 1.11 | K |
| 55 | 0.0153 | 0.879 | 6.15 | A |
| 56 | 0.0028 | 2.127 | 1.24 | K |
| 57 | 0.0097 | 1.460 | 9.41 | I |
| 58 | 0.0154 | 4.228 | 1.55 | K |
| 59 | 0.1124 | — | 1.52 | K |
| 60 | 0.3495 | — | 1.26 | N |
| 61 | 0.0944 | — | 1.28 | K |
| 62 | 0.0023 | 2.512 | 1.33 | L |
| 63 | 0.0022 | — | 1.39 | K |

What is claimed is:
1. A compound of Formula (I):

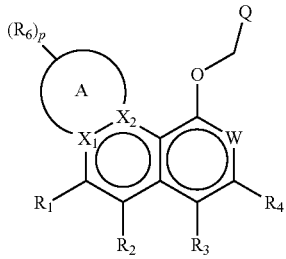
(I)

or a salt or prodrug thereof, wherein:
W is $CR_5$ or N;
$X_1$ and $X_2$ are independently C or N, provided that zero or one of $X_1$ and $X_2$ is N;
Ring A represented by the structure

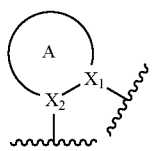

is:

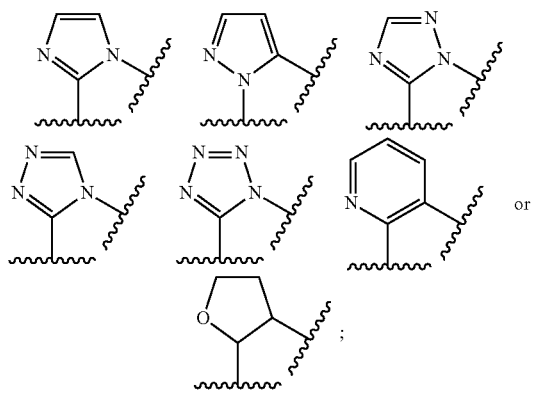
;

$R_1$ is —CN or —C(O)NH$_2$;
$R_2$ is hydrogen or —NH(CH$_3$);
$R_3$ is hydrogen or F
$R_4$ is hydrogen, F, or —CH$_3$;
$R_5$ is hydrogen;
each $R_6$ is independently —CH$_3$, —CF$_3$, or —C(CH$_3$)$_2$OH;
Q is

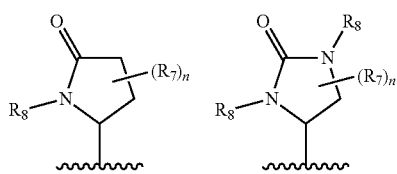

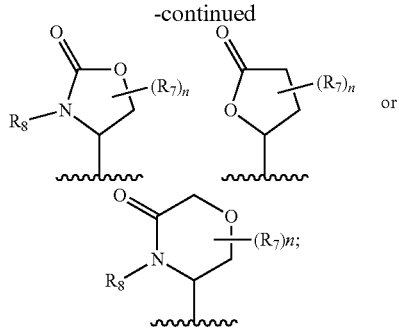
or each $R_7$ is F, $C_{1-3}$ alkyl, or $C_{1-2}$ fluoroalkyl;
each $R_8$ is independently hydrogen or —CH$_2$OH;
n is zero, 1, 2, or 3; and
p is zero, 1 or 2.

2. The compound according to claim 1 or a salt or prodrug thereof, wherein:
W is $CR_5$.

3. The compound according to claim 1 or a salt or prodrug thereof, wherein:
W is N.

4. The compound according to claim 1 or a salt or prodrug thereof, wherein one of $X_1$ and $X_2$ is $CR_5$ and the other of $X_1$ and $X_2$ is N.

5. The compound according to claim 1 having the structure of Formula (II)

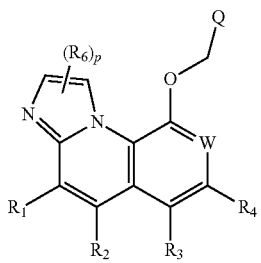
(II)

or a salt or prodrug thereof.

6. The compound according to claim 1 or a salt or prodrug thereof, wherein:
Ring A is:

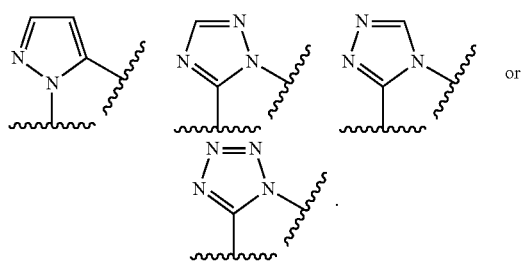

7. The compound according to claim 1 or a salt or prodrug thereof, wherein Ring A is:

8. The compound according to claim 1 or a salt or prodrug thereof, wherein Ring A is:

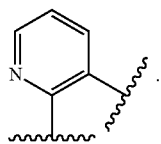 [SMILES: *c1cccnc1*]

9. The compound according to claim 1 or a salt or prodrug thereof, wherein:
Q is

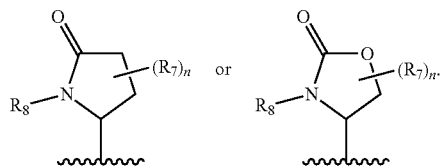

10. The compound according to claim 1 or a salt thereof, wherein said compound is selected from:
- (S)-9-((5-oxopyrrolidin-2-yl)methoxy)imidazo[1,2-a]quinoline-4-carboxamide (1);
- 9-(((2S,3R)-3-ethyl-5-oxopyrrolidin-2-yl)methoxy)imidazo[1,2-a]quinoline-4-carboxamide (2);
- 9-(((2S,3 S)-3-ethyl-5-oxopyrrolidin-2-yl)methoxy) imidazo[1,2-a]quinoline-4-carboxamide (3);
- 9-(((2S,3 S,4R)-3-ethyl-4-fluoro-5-oxopyrrolidin-2-yl)methoxy)imidazo[1,2-a]quinoline-4-carboxamide (4);
- 9-(((2S,3S,4S)-3-ethyl-4-fluoro-5-oxopyrrolidin-2-yl)methoxy)imidazo[1,2-a]quinoline-4-carboxamide (5);
- 9-(((2S,3 S,4S)-3-ethyl-4-fluoro-4-methyl-5-oxopyrrolidin-2-yl)methoxy) imidazo[1,2-a]quinoline-4-carboxamide (6);
- (R)-9-((5-oxomorpholin-3-yl)methoxy) imidazo[1,2-a]quinoline-4-carboxamide (7);
- 9-(((2S,3S)-3-ethyl-4,4-difluoro-5-oxopyrrolidin-2-yl)methoxy)imidazo[1,2-a]quinoline-4-carboxamide (10);
- 9-(((2S,3R)-3-ethyl-5-oxopyrrolidin-2-yl)methoxy)-2-methylimidazo[1,2-a]quinoline-4-carboxamide (11);
- 9-(((2S,3S,4S)-3-ethyl-4-fluoro-5-oxopyrrolidin-2-yl)methoxy)-2-methylimidazo[1,2-a]quinoline-4-carboxamide (12);
- 9-(((2S,3S,4S)-3-ethyl-4-fluoro-5-oxopyrrolidin-2-yl)methoxy)-2-(2-hydroxypropan-2-yl) imidazo[1,2-a]quinoline-4-carboxamide (13);
- 9-(((2S,3R)-3-ethyl-5-oxopyrrolidin-2-yl)methoxy)-6-fluoroimidazo[1,2-a]quinoline-4-carboxamide (14);
- 9-(((2S,3S,4S)-3-ethyl-4-fluoro-5-oxopyrrolidin-2-yl)methoxy)-6-fluoroimidazo[1,2-a]quinoline-4-carboxamide (15);
- 1-(((2S,3R)-3-ethyl-5-oxopyrrolidin-2-yl)methoxy)imidazo[1,2-a][1,7]naphthyridine-6-carboxamide (16);
- 1-(((2S,3S,4S)-3-ethyl-4-fluoro-5-oxopyrrolidin-2-yl)methoxy)imidazo[1,2-a][1,7]naphthyridine-6-carboxamide (17);
- 1-(((2S,3R)-3-ethyl-5-oxopyrrolidin-2-yl)methoxy)-8-methylimidazo[1,2-a][1,7]naphthyridine-6-carboxamide (18);
- 1-(((2S,3S,4S)-3-ethyl-4-fluoro-5-oxopyrrolidin-2-yl)methoxy)-8-methylimidazo[1,2-a][1,7]naphthyridine-6-carboxamide (19);
- 1-(((2S,3S)-3-ethyl-4,4-difluoro-5-oxopyrrolidin-2-yl)methoxy) imidazo[1,2-a][1,7]naphthyridine-6-carboxamide (20);
- 1-(((2S,3S)-3-ethyl-4,4-difluoro-5-oxopyrrolidin-2-yl)methoxy)-8-methylimidazo[1,2-a][1,7]naphthyridine-6-carboxamide (21);
- 1-(((4R,5S)-5-ethyl-2-oxooxazolidin-4-yl)methoxy)imidazo[1,2-a][1,7]naphthyridine-6-carboxamide (22);
- 1-(((4S,5R)-5-ethyl-2-oxooxazolidin-4-yl) methoxy)imidazo[1,2-a][1,7]naphthyridine-6-carboxamide (23);
- 1-(((4S,5S)-5-ethyl-2-oxooxazolidin-4-yl)methoxy)imidazo[1,2-a][1,7]naphthyridine-6-carboxamide (24);
- 1-(((2R,3S)-2-ethyl-5-oxomorpholin-3-yl)methoxy)imidazo[1,2-a][1,7]naphthyridine-6-carboxamide (25);
- 1-(((2S,3R)-2-ethyl-5-oxomorpholin-3-yl)methoxy)imidazo[1,2-a][1,7]naphthyridine-6-carboxamide (26);
- (S)-1-((2-oxoimidazolidin-4-yl)methoxy) imidazo[1,2-a][1,7]naphthyridine-6-carboxamide (27);
- 1-(((2S,3R)-3-ethyl-5-oxopyrrolidin-2-yl)methoxy)-3-methylimidazo[1,2-a][1,7]naphthyridine-6-carboxamide (28);
- 1-(((2S,3R)-3-ethyl-5-oxopyrrolidin-2-yl)methoxy)-3,8-dimethylimidazo[1,2-a][1,7]naphthyridine-6-carboxamide (29);
- 1-(((2S,3R)-3-ethyl-5-oxopyrrolidin-2-yl)methoxy)-8-(trifluoromethyl)imidazo[1,2-a][1,7]naphthyridine-6-carboxamide (30);
- 1-(((2S,3 S)-3-ethyl-5-oxopyrrolidin-2-yl) methoxy)-8-(trifluoromethyl)imidazo[1,2-a][1,7]naphthyridine-6-carboxamide (31);
- (1-(((2S,3S,4S)-3-ethyl-4-fluoro-1-(hydroxymethyl)-5-oxopyrrolidin-2-yl)methoxy) imidazo[1,2-a][1,7]naphthyridine-6-carboxamide (32);
- 1-((((3R)-3-ethyl-5-oxopyrrolidin-2-yl)methyl)amino) imidazo[1,2-a][1,7]naphthyridine-6-carboxamide (33);
- 10-(((2S,3S,4S)-3-ethyl-4-fluoro-5-oxopyrrolidin-2-yl)methoxy)pyrazolo[5,1-a]isoquinoline-5-carboxamide (34);
- 10-(((2S,3R)-3-ethyl-5-oxopyrrolidin-2-yl)methoxy) pyrazolo[5,1-a]isoquinoline-5-carboxamide (35);
- 1-(((2S,3S,4S)-3-ethyl-4-fluoro-5-oxopyrrolidin-2-yl)methoxy) pyrazolo[5,1-a][2,7]naphthyridine-6-carboxamide (36);
- 9-(((2S,3R)-3-ethyl-5-oxopyrrolidin-2-yl)methoxy)-[1,2,4]triazolo[1,5-a]quinoline-4-carboxamide (37);
- 9-(((2S,3S,4S)-3-ethyl-4-fluoro-5-oxopyrrolidin-2-yl)methoxy)-[1,2,4]triazolo[1,5-a]quinoline-4-carboxamide (38);
- 9-(((2S,3S)-3-ethyl-4,4-difluoro-5-oxopyrrolidin-2-yl)methoxy)-[1,2,4]triazolo[1,5-a]quinoline-4-carboxamide (39);
- 9-(((2S,3 S,4S)-3-ethyl-4-fluoro-5-oxopyrrolidin-2-yl)methoxy)-2-methyl-[1,2,4]triazolo[1,5-a]quinoline-4-carboxamide (40);
- 9-(((2S,3R)-3-ethyl-5-oxopyrrolidin-2-yl)methoxy)-[1,2,4]triazolo[4,3-a]quinoline-4-carboxamide (41);
- 9-(((2S,3S)-3-ethyl-5-oxopyrrolidin-2-yl) methoxy)-[1,2,4]triazolo[4,3-a]quinoline-4-carboxamide (42);
- 9-(((2S,3S,4S)-3-ethyl-4-fluoro-5-oxopyrrolidin-2-yl)methoxy)-[1,2,4]triazolo[4,3-a]quinoline-4-carboxamide (43);

9-(((2S,3R)-3-ethyl-5-oxopyrrolidin-2-yl)methoxy)tetrazolo[1,5-a]quinoline-4-carboxamide (44);

9-(((2S,3 S,4S)-3-ethyl-4-fluoro-5-oxopyrrolidin-2-yl) methoxy) tetrazolo[1,5-a]quinoline-4-carboxamide (45);

9-(((2S,3R)-3-ethyl-5-oxopyrrolidin-2-yl)methoxy)-[1,2,4]triazolo[1,5-a][1,7]naphthyridine-4-carboxamide (46);

9-(((2S,3S,4S)-3-ethyl-4-fluoro-5-oxopyrrolidin-2-yl) methoxy)-[1,2,4]triazolo[1,5-a][1,7]naphthyridine-4-carboxamide (47);

9-(((2S,3S)-3-ethyl-4,4-difluoro-5-oxopyrrolidin-2-yl) methoxy)-[1,2,4]triazolo[1,5-a][1,7]naphthyridine-4-carboxamide (48);

9-(((2S,3R)-3-ethyl-5-oxopyrrolidin-2-yl)methoxy)-2-methyl-[1,2,4]triazolo[1,5-a][1,7]naphthyridine-4-carboxamide (49);

1-(((2S,3S,4S)-3-ethyl-4-fluoro-5-oxotetrahydrofuran-2-yl)methoxy)-8-methyl-8,9-dihydrofuro[2,3-h]isoquinoline-6-carboxamide (50-52);

1-(((2S,3R)-3-ethyl-5-oxotetrahydrofuran-2-yl) methoxy)-8-methyl-8,9-dihydrofuro[2,3-h]isoquinoline-6-carboxamide (53);

1-(((2S,3R)-3-ethyl-5-oxopyrrolidin-2-yl)methoxy)-8,9-dihydrofuro[2,3-h]isoquinoline-6-carboxamide (54);

1-(((2S,3R)-3-ethyl-5-oxopyrrolidin-2-yl)methoxy)-2,7-phenanthroline-6-carboxamide (55);

1-(((2S,3S,4S)-3-ethyl-4-fluoro-5-oxopyrrolidin-2-yl) methoxy)-2,7-phenanthroline-6-carboxamide (56);

9-(((2S,3R)-3-ethyl-5-oxopyrrolidin-2-yl)methoxy)-7-fluoro-5a,9a-dihydroimidazo[1,2-a]quinoline-4-carboxamide (57);

9-(((2S,3S,4S)-3-ethyl-4-fluoro-5-oxopyrrolidin-2-yl) methoxy)-7-fluoro-5a,9a-dihydroimidazo[1,2-a]quinoline-4-carboxamide (58);

9-(((2S,3R)-3-ethyl-5-oxopyrrolidin-2-yl)methoxy)-8-fluoro-5a,9a-dihydroimidazo[1,2-a]quinoline-4-carboxamide (59);

9-(((2S,3R)-3-ethyl-5-oxopyrrolidin-2-yl)methoxy)-5a,9a-dihydroimidazo[1,2-a]quinoline-4-carbonitrile (60);

9-(((2S,3S,4S)-3-ethyl-4-fluoro-5-oxopyrrolidin-2-yl) methoxy)-5-(methylamino)-5a,9a-dihydroimidazo[1,2-a]quinoline-4-carboxamide (61);

10-(((2S,3S,4S)-3-ethyl-4-fluoro-5-oxopyrrolidin-2-yl) methoxy)-2-methyl-6a,10a-dihydropyrazolo[5,1-a]isoquinoline-5-carboxamide (62); and 1-(((2S,3S,4S)-3-ethyl-4-fluoro-5-oxopyrrolidin-2-yl) methoxy)-8,8-dimethyl-8,9-dihydrofuro[2,3-h]isoquinoline-6-carboxamide (63).

11. A pharmaceutical composition comprising a compound according to claim 1 or a pharmaceutically acceptable salt thereof; and a pharmaceutically acceptable carrier or diluent.

12. A method of treating a disease, comprising administering to a patient a therapeutically-effective amount of a compound according to claim 1 or a pharmaceutically acceptable salt thereof, wherein the disease is selected from Crohn's disease, ulcerative colitis, asthma, graft versus host disease, allograft rejection, chronic obstructive pulmonary disease, Graves' disease, rheumatoid arthritis, systemic lupus erythematosus, lupus nephritis, cutaneous lupus, psoriasis, cryopyrin-associated periodic syndromes, TNF receptor associated periodic syndrome, familial Mediterranean fever, adult onset stills, systemic onset juvenile idiopathic arthritis, multiple sclerosis, neuropathic pain, gout, and gouty arthritis.

\* \* \* \* \*

SEQUENCE LISTING

```
<160> NUMBER OF SEQ ID NOS: 1

<210> SEQ ID NO 1
<211> LENGTH: 16
<212> TYPE: PRT
<213> ORGANISM: Homo sapiens
<220> FEATURE:
<221> NAME/KEY: misc_feature
<223> OTHER INFORMATION: Flourescent tag attached to amino acid 1

<400> SEQUENCE: 1

Ile Pro Thr Ser Pro Ile Thr Thr Thr Tyr Phe Phe Phe Lys Lys Lys
1               5                   10                  15
```